United States Patent
Huang

(10) Patent No.: US 7,741,283 B2
(45) Date of Patent: Jun. 22, 2010

(54) COMPOSITIONS AND METHODS FOR INHIBITING CELL PROLIFERATION

(75) Inventor: Jung Huang, St. Louis, MO (US)

(73) Assignee: St. Louis University, St. Louis, MO (US)

( * ) Notice: Subject to any disclaimer, the term of this patent is extended or adjusted under 35 U.S.C. 154(b) by 1238 days.

(21) Appl. No.: 10/966,371

(22) Filed: Oct. 15, 2004

(65) Prior Publication Data

US 2005/0250692 A1 Nov. 10, 2005

Related U.S. Application Data

(60) Provisional application No. 60/512,516, filed on Oct. 17, 2003.

(51) Int. Cl.
*A61K 38/00* (2006.01)
(52) U.S. Cl. ........................................... 514/12
(58) Field of Classification Search ........................ None
See application file for complete search history.

(56) References Cited

OTHER PUBLICATIONS

Tanaka et al., Cancer Res. Aug. 1, 1996;56(15):3391-4.*
Huynh et al., Cell Growth & Diff. Mar. 2002;13:115-122.*
Ricort et al., J Biol Chem. May 31, 2002;277(22):19448-19454.*
Liu et al., J Biol Chem. Jul. 25, 1997;272(30):18891-18895.*
Rocha et al., Clin Can Res. Jan. 1997;3:103-109.*
Leal et al., J Biol Chem. Aug. 15, 1997;272(33):20572-20576.*
Juengst, BMJ Jun. 28, 2003;326(7404):1410-1.*

* cited by examiner

*Primary Examiner*—Cherie Woodward
(74) *Attorney, Agent, or Firm*—Elmore Patent Law Group, P.C.; Carolyn S. Elmore; Roy P. Issac

(57) ABSTRACT

Disclosed are compositions and methods useful in the regulation of cell proliferation. The invention provides TGF-β (transforming growth factor β) and IGFBP-3 (insulin like growth factor binding protein 3) as ligands that engage LRP (low density lipoprotein receptor-related protein), heretofore known as TβR-V (TGF-β receptor V) and IGFBP-3 receptor, to effect a change in the phosphorylation and activation status of IRS (insulin receptor substrate) proteins. Compositions comprising TGF-β or IGFBP-3 and LRP or IRS protein are useful in the inhibition of cell proliferation and in the treatment of various diseases associated with unregulated cell proliferation.

5 Claims, 18 Drawing Sheets

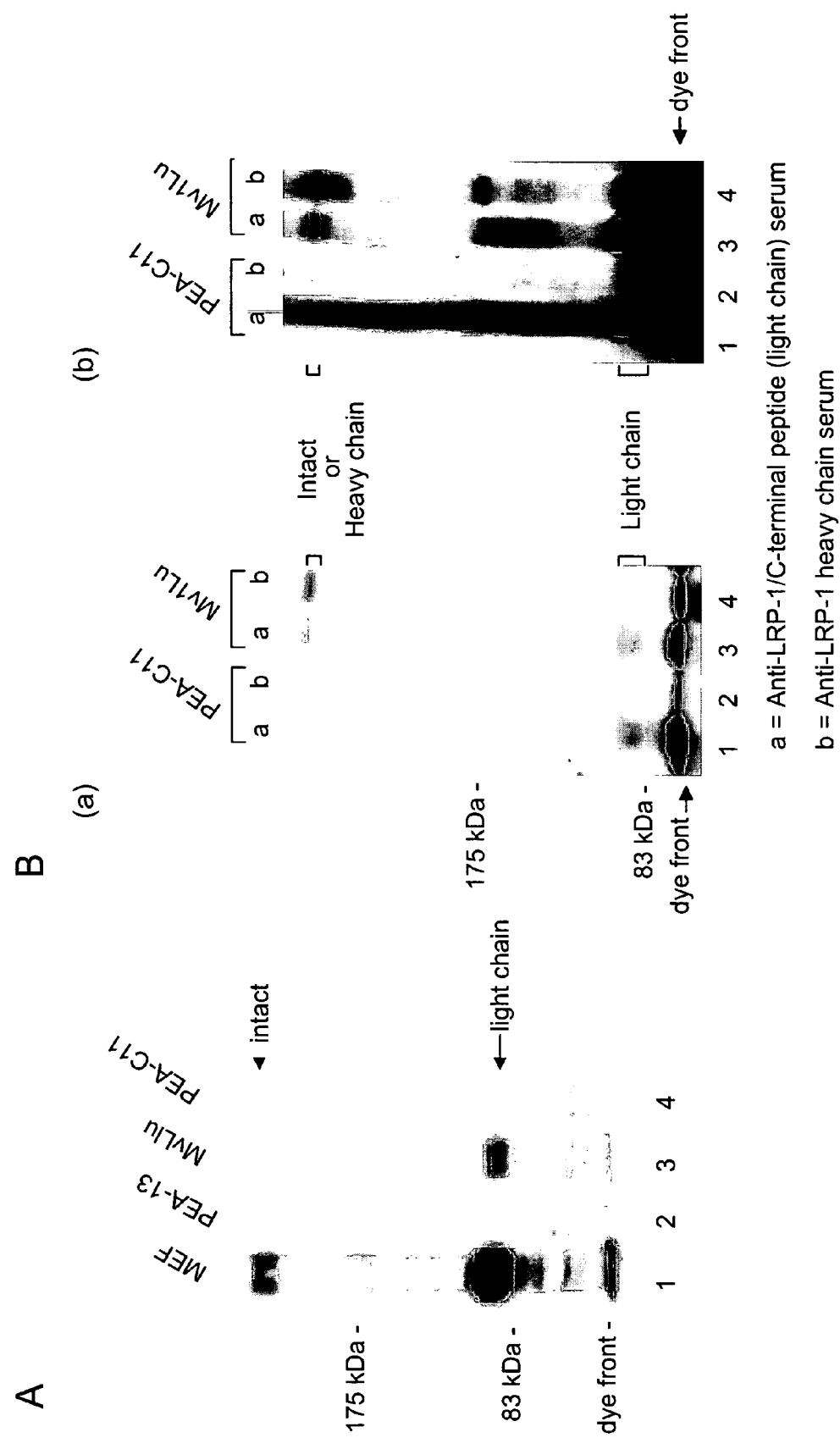
Fig 5 A and B

Fig 7
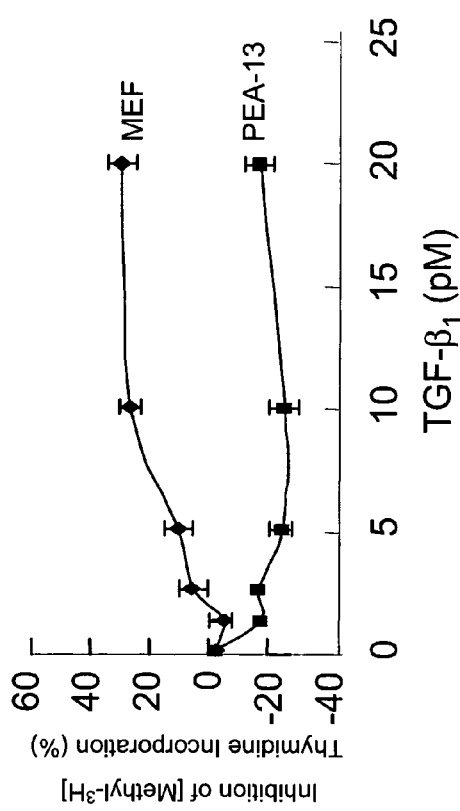
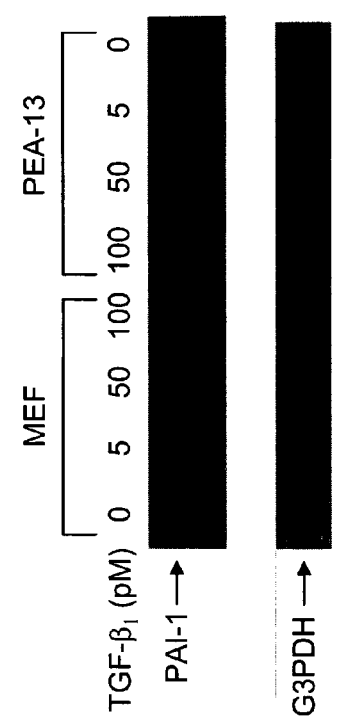
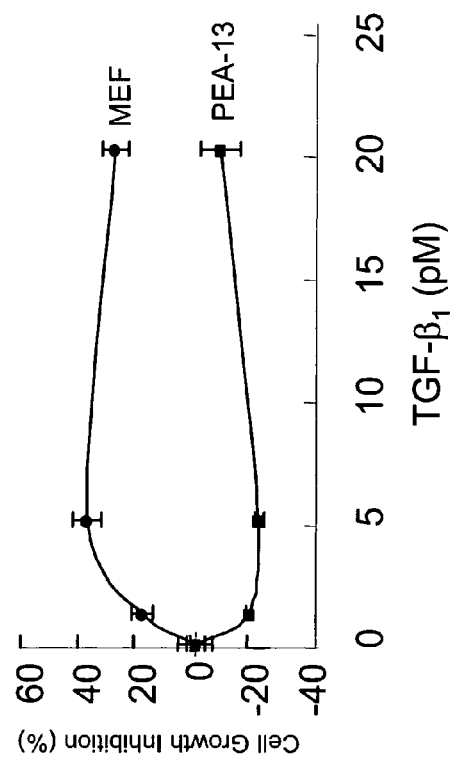

Fig 16
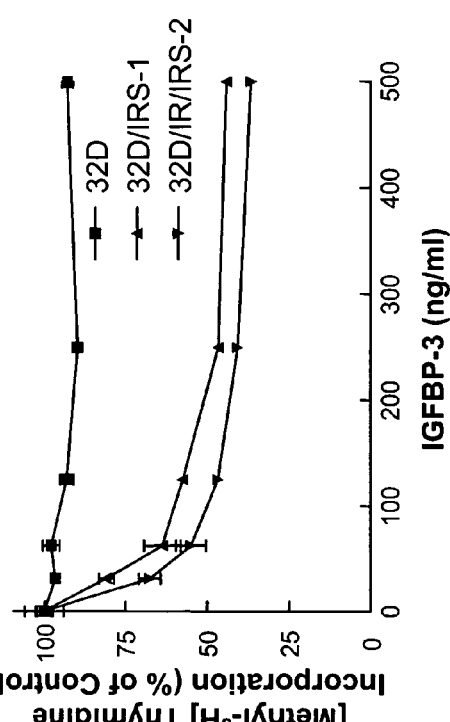
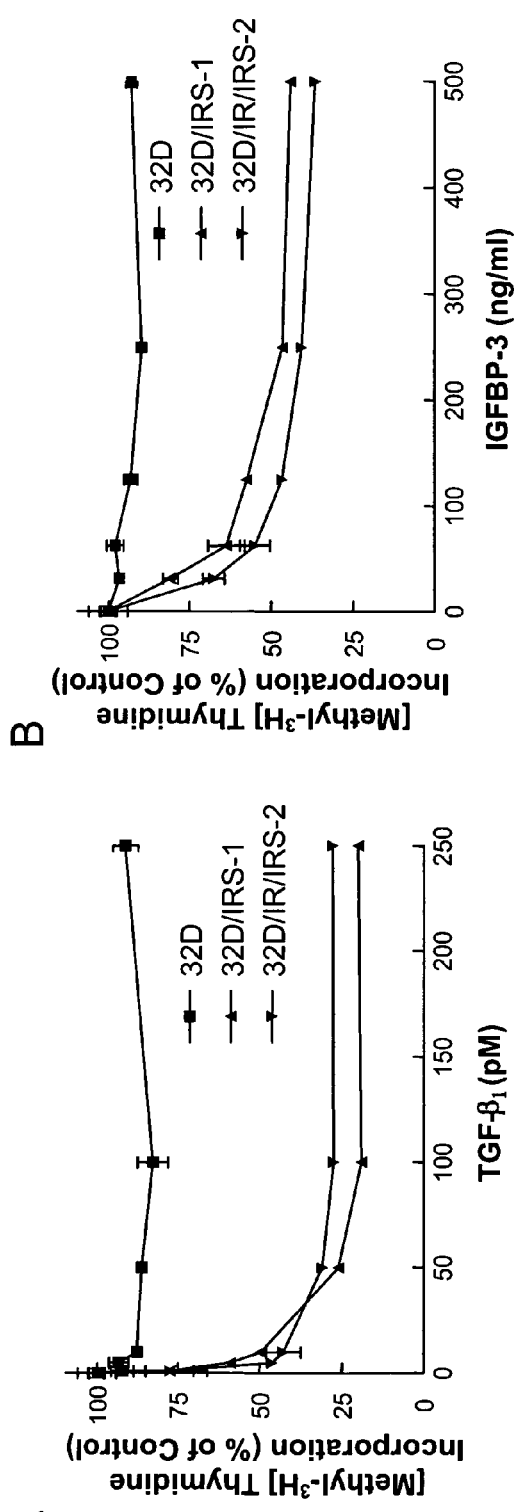
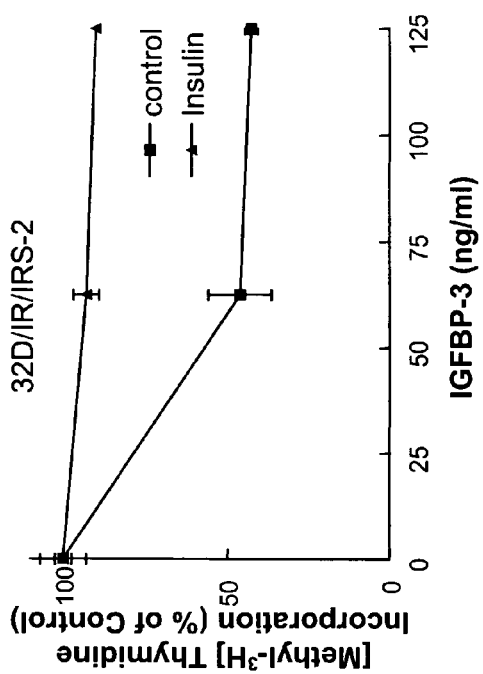
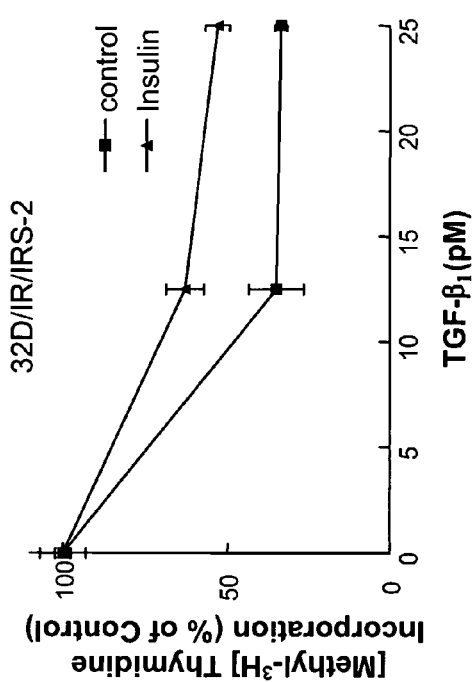

COMPOSITIONS AND METHODS FOR INHIBITING CELL PROLIFERATION

PARENT CASE TEXT

This application claims benefit of priority to U.S. Provisional Patent Application No. 60/512,516, which was filed on Oct. 17, 2003.

GOVERNMENT SUPPORT CLAUSE

This invention was made with government support under Grant No. CA 38808 awarded by The U.S. National Institutes of Health. The government has certain rights in the invention.

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION

1. Field of the invention

The invention relates generally to the regulation of cell growth and disease through TGF-β-receptor V signaling.

2. Summary of the Related Art

TβR-V

Transforming growth factor-β (TGF-β) is a family of structurally homologous dimeric proteins; three mammalian isoforms (TGF-$β_1$, TGF-$β_2$ and TGF-$β_3$) share approximately 70% sequence identity and exhibit distinct functions in vivo (1,2). All three TGF-β isoforms are physiologically important. Null mutations in a gene encoding any one of the TGF-β isoforms cannot be corrected by other family members (3). TGF-β isoforms regulate multiple biological processes, including proliferation, extracellular matrix synthesis, angiogenesis, immune response, apoptosis and differentiation (3). They have been implicated in the pathogenesis of tissue fibrosis, autoimmune diseases, cancer and other disorders (3).

The various biological activities of TGF-β isoforms (collectively referred to as TGF-β) are mediated by specific cell surface receptors in responsive cells. Multiple cell surface receptors of various sizes have been identified in cultured cells and tissues by cross-linking of $^{125}$I-labeled-TGF-β ($^{125}$I-TGF-β) to these molecules in the presence of bifunctional cross-linking reagents. These include type I (TβR-I, M.W. ~53,000), type II (TβR-II, M.W. ~70,000), type III (TβR-III, M.W. ~280,000-370,000), type IV (TβR-IV, M.W. ~60,000), type V (TβR-V, M.W. ~400,000) and type VI (TβR-VI, M.W. ~180,000) receptors as well as several membrane-associated binding proteins (M.W. ~38,000-190,000) (4,5). TβR-I and TβR-II are Ser/Thr-specific protein kinases and are believed to be primarily responsible for TGF-β-induced cellular responses (6,7). TβR-III is a proteoglycan-containing membrane glycoprotein which presents the ligand to other TGF-β receptor types and has recently been reported to regulate signaling mediated by the TβR-I/TβR-II heterocomplex (8-10). The identity of TβR-IV has not been confirmed by independent studies (11,12). TβR-V coexpresses with TβR-I, TβR-II and TβR-III in most cell types (13) and also serves as the insulin-like growth factor binding protein-3 (IGFBP-3) receptor mediating IGF-independent (TGF-β antagonist sensitive) growth inhibition upon IGFBP-3 stimulation (14-16). The TβR-VI and other membrane-associated TGF-β binding proteins are expressed only in specific cell types (4,5).

One prominent activity of TGF-β is transcriptional activation of genes coding for extracellular matrix proteins and their regulatory proteins (e.g., collagen, fibronectin and plasminogen activator inhibitor-1). Another activity is cellular growth regulation, wherein TGF-β inhibits the growth of most cell types including epithelial cells, endothelial cells, embryonic fibroblasts and hematopoietic cells, and stimulates growth of certain mesenchymal cells (e.g., fibroblasts) and other specific cell types. Accumulating evidence indicates that these two activities are uncoupled in some cell types under certain experimental conditions and are probably mediated by distinct signaling pathways (14,17-22).

The segregation of the activities cannot be easily interpreted with a simple model of TβR-I/TβR-II complex formation followed by Smad2/Smad3/Smad4 signaling (6,7).

The TβR-V is expressed in most cell types used to investigate the TGF-β-induced growth regulation and signaling via the TβR-I/TβR-II heterocomplex (6,7,23). The recent discovery that the TβR-V is identical to the IGFBP-3 receptor (14-16), which mediates IGF-independent growth inhibition induced by IGFBP-3, highlights the potential importance of TβR-V in TGF-β-induced growth regulation. A pivotal role of TβR-V in this important activity is also supported by the observation that cells expressing little or no TβR-V do not exhibit the growth inhibitory response to TGF-$β_1$ (14,24). Many human carcinoma cells express little or no TβR-V (13,16).

To elucidate the role of TβR-V in both TGF-β- and IGFBP-3-induced growth suppression, the inventor examined the structure and function of TβR-V purified and expressed in cultured cells. Unexpectedly, the studies disclosed herein demonstrated that TβR-V/IGFBP-3 receptor is identical to the low density lipoprotein receptor-related protein ("LRP") (25), providing evidence for a new and previously unreported function for LRP.

LRP

Low density lipoprotein receptor-related protein ("LRP") is known in the art as an endocytic receptor, which mediates the uptake, metabolism, degradation, plasma clearance or removal of approximately 30 structurally unrelated ligands (31,32,34). Those ligands include lipoproteins (i.e., e.g., apoE), proteinases, proteinase-inhibitor complexes, extracellular matrix (ECM) proteins, connective tissue growth factor ("CTGF"; see Segarini et al, U.S. Pat. No. 6,555,322, which is incorporated herein by reference), α2-macroglobulin, bacterial toxins, viruses, and intracellular proteins, such as receptor associated protein ("RAP"). LRP is known also as the α2-macroglobulin receptor. The cytoplasmic tail of LRP has been shown to interact with various intracellular adapter and scaffold proteins, suggesting a role for LRP in MAP kinase signaling, vesicle transport, neurotransmission, cytoskeletal organization, and amyloid precursor protein (APP) processing. However, no role for LRP has been suggested for TGF-β, IGFBP-3, insulin, or IGF-1 signal transduction. For a review of the state of the LRP art, see Herz and Strickland, "LRP: a multifunctional scavenger and signaling receptor," J. Clin. Invest. 108:779-784 (2001), which is incorporated herein by reference.

Signaling through IRS

As discussed above, TGF-β signaling occurs via type I, II, III, IV, V and VI receptors, as well as several membrane binding proteins. TβR-I/TβR-II heterocomplex-mediated signaling, which is generally believed to be primarily responsible for TGF-β-induced cellular responses, has been studied extensively (6,7,23). Following ligand binding, TβR-II and TβR-I form heterocomplexes resulting in activation of the cytoplasmic kinase activity of TβR-I in the heterocomplex. The activated TβR-I then phosphorylates and activates Smad2 and Smad3. The activated Smad2/Smad3 forms oligomers with Smad4, which translocate to the nucleus to regulate the expression of target genes. The expression of the target genes directs the cellular responses to TGF-β stimulation.

The growth inhibitory response to TGF-$β_1$ has been studied in a variety of in vitro cultured cell systems. It is generally thought that the TGF-β-activated Smad proteins target the promoters of the c-myc gene and cyclin-dependent kinases and repress its transcription in cooperation with nuclear co-repressors. The various Smad protein and transcriptional co-activator complexes are also thought to activate the transcription of three major cell cycle inhibitors, the cyclin-dependent kinase inhibitors (6,7,23,44). These inhibit cyclin-dependent kinase activities associated with the G1 to S phase progression, prevent phosphorylation of RB by cyclin-dependent kinases, and arrest cells in G1. Currently, the exact molecular bases of Smad protein co-repressor and co-activator complex formation are not well understood. (For a review of TGF-β signaling through Smad signaling, see Shi and Massague, "Mechanisms of TGF-β signaling from cell membrane to the nucleus," Cell 113:685-700 (2003), which is incorporated herein by reference).

An important question, which is addressed by the invention and which is herein disclosed, is how does TGF-β or IGFBP-3 signaling propagate through the TβR-V? The inventor herein discloses that TGF-β or IGFBP-3 stimulates changes in the serine-specific phosphorylation status of IRS proteins, presumably through TβR-V signaling, thereby mediating growth inhibition.

Insulin Receptor Substrate ("IRS") proteins are intracellular signal transduction molecules which are substrates of ligand activated receptor tyrosine kinases. IRS-dependent receptor tyrosine kinases include the receptors for insulin/IGF-1, growth hormone, IL-4, IL-9, IL-13, interferons and leukemia inhibitory factor. However, most cytokine receptors, including receptors for EGF and PDGF, do not utilize IRS proteins to propagate a signal through the cell. For example, when insulin binds its receptor, the cytoplasmic portion of the insulin receptor undergoes tyrosine phosphorylation. The pTyr residues bind to and activate the IRS proteins via tyrosine phosphorylation. Activated IRS proteins bind to and activate phosphatidylinositol 3' kinase ("PI3'K"), and stimulate mitogenesis, glucose transport and insulin-associated gene transcription.

In the absence of insulin, IRS proteins, which are considered to be in the "off" state, are strongly serine phosphorylated and weakly tyrosine phosphorylated. Insulin-binding stimulates an increase in serine, threonine and tyrosine phosphorylation. Serine phosphorylation of IRS-1 is postulated to decrease the association of IRS and insulin receptor. Thus, changing the IRS phosphorylation states serves to increase as well as attenuate signaling through the insulin/IGF-1 receptor tyrosine kinase. For a review of the role of IRS proteins in receptor tyrosine kinase signaling, see Myers and White, "Insulin signal transduction and the IRS proteins," Ann. Rev. Pharmacol. Toxicol. 36:615-658, 1996, which is incorporated herein by reference.

REFERENCES CITED

1. Roberts, A. B. and Sporn, M. B. (1990) The transforming growth factor-βs. In Sporn, M. B. and Roberts, A. B. (eds.), *Handbook of Experimental Pharmacology: Peptide Growth Factors and Their Receptors*, Springer-Verlag, New York, pp. 419-472.

2. Massagué, J. (1990) The transforming growth factor-β family. *Annu. Rev. Cell Biol.* 6, 597-641.

3. Roberts, A. B. (1998) Molecular and cell biology of TGF-β. *Min. Electrol. Metab.* 24, 111-119.

4. Massagué, J. (1992) Receptors for the TGF-β family. *Cell* 69, 1067-1070.

5. Yingling, J. M., Wang, X. F. and Bassing, C. H. (1995) Signaling by the transforming growth factor-β receptors. *Biochim. Biophys. Acta* 1242, 115-136.

6. Heldin, C. H., Miyazono, K. and ten Dijke, P. (1997) TGF-β signalling from cell membrane to nucleus through SMAD proteins. *Nature* 390, 465-471.

7. Massagué, J. (1998) TGF-β signal transduction. *Annu. Rev. Biochem.* 67, 753-791.

8. Blobe, G. C., Schiemann, W. P., Pepin, M. C., Beauchemin, M., Moustakas, A., Lodish, H. F. and O'Connor-McCourt, M. D. (2001) Functional roles for the cytoplasmic domain of the type III transforming growth factor β receptor in regulating transforming growth factor β signaling. *J. Biol. Chem.* 276, 24627-24637.

9. Blobe, G. C., Liu, X., Fang, S.J., How, T., and Lodish, H. F. (2001) A novel mechanism for regulating transforming growth factor β (TGF-β) signaling. Functional modulation of type III TGF-β receptor expression through interaction with the PDZ domain protein, GIPC. *J. Biol. Chem.* 276, 39608-39617.

10. Eickelberg, O., Centrella, M., Reiss, M., Kashgarian, M., and Wells, r. G. (2002) Betaglycan inhibits TGF-β signaling by preventing type I-type II receptor complex formation. Glycosaminoglycan modifications alter betaglycan function. *J. Biol. Chem.* 277, 823-829.

11. Moustakas, A., Takumi, T., Lin, H.-Y., and Lodish, H. F. (1995) GH3 pituitary tumor cells contain heteromeric type I and type II receptor complexes for transforming growth factor β and activin A. *J. Biol. Chem.* 270, 765-769.

12. Yamashita, H., Okadome, T., Franzen, P., ten Dijke, P., Heldin, C.-H., and Miyazono, K. (1995) A rat pituitary tumor cell line (GH3) expresses type I and type II receptors and cell surface binding protein(s) for transforming growth factor β. *J. Biol. Chem.* 270, 770-774.

13. O'Grady, P., Huang, S. S. and Huang, J. S. (1991) Expression of a new type high molecular weight receptor (type V receptor) of transforming growth factor β in normal and transformed cells. *Biochem. Biophys. Res. Comm.* 179, 378-385.

14. Leal, S. M., Liu, Q., Huang, S. S. and Huang, J. S. (1997) The type V transforming growth factor β receptor is the putative insulin-like growth factor-binding protein 3 receptor. *J. Biol. Chem.* 272, 20572-20576.

15. Leal, S. M., Huang, S. S. and Huang, J. S. (1999) Interactions of high affinity insulin-like growth factor-binding proteins with the type V transforming growth factor-β receptor in mink lung epithelial cells. *J. Biol. Chem.* 274, 6711-6717.

16. Wu, H. B., Kumar, A., Tsai, W. C., Mascarenhas, D., Healey, J. and Rechler, M. M. (2000) Characterization of the 17. Taipale, J. and Keski-Oja, J. (1996) Hepatocyte growth factor releases epithelial and endothelial cells from growth arrest induced by transforming growth factor-β1. *J. Biol. Chem.* 271, 4342-4348.

18. Wang, J., Han, W., Zborowska, E., Liang, J., Wang, X., Willson, J. K., Sun, L. and Brattain, M. G. (1996) Reduced expression of transforming growth factor β type I receptor contributes to the malignancy of human colon carcinoma cells. *J. Biol. Chem.* 271, 17366-17371.

19. Hocevar, B. A. and Howe, P. H. (1998) Mechanisms of TGF-β-induced cell cycle arrest. *Min. Electrol. Metab.* 24, 131-135.

20. Heldin, N.-E., Bergerstöm, D., Hermansson, A., Bergenstråhle, A., Nakao, A., Westermark, B. and ten Dijke, P. (1999) Lack of responsiveness of TGF-$β_1$ in a thyroid carcinoma cell line with functional type I and type II TGF-β receptors and Smade proteins, suggests a novel mechanism for TGF-β insensitivity in carcinoma cells. *Molecular. Cell. Edocrinol.* 153, 79-90.

21. Petritsch, C., Beug, H., Balmain, A. and Oft, M. (2000) TGF-β inhibits p70 S6 kinase via protein phosphatase 2A to induce G(1) arrest. *Genes Dev.* 14, 3093-3101.

22. Fink, S. P., Swinler, S. E., Lutterbaugh, J. D., Massagué, J., Thiagalingam, S., Kinzler, K. W., Vogelstein, B., Willson, J. K. and Markowitz, S. (2001) Transforming growth factor-β-induced growth inhibition in a Smad4 mutant colon adenoma cell line. *Cancer Res.* 61, 256-260.

23. Moustakas, A., Pardali, K., Gaal, A. and Heldin, C. H. (2002) Mechanisms of TGF-β signaling in regulation of cell growth and differentiation. *Immunol. Letts.* 82, 85-91.

24. Liu, Q., Huang, S. S. and Huang, J. S. (1997) Function of the type V transforming growth factor β receptor in transforming growth factor β-induced growth inhibition of mink lung epithelial cells. *J. Biol. Chem.* 272, 18891-18895.

25. Herz, J., Hamann, U., Rogne, S., Myklebost, O., Gausepohl, H. and Stanley, K. K. (1988) Surface location and high affinity for calcium of a 500-kd liver membrane protein closely related to the LDL-receptor suggest a physiological role as lipoprotein receptor. *EMBO J.* 7, 4119-4127.

26. Boensch, C., Huang, S. S., Connolly, D. T. and Huang, J. S. (1999) Cell surface retention sequence binding protein-1 interacts with the v-sis gene product and platelet-derived growth factor β-type receptor in simian sarcoma virus-transformed cells. *J. Biol. Chem.* 274, 10582-10589.

27. O'Grady, P., Kuo, M. D., Baldassare, J. J., Huang, S. S. and Huang, J. S. (1991) Purification of a new type high molecular weight receptor (type V receptor) of transforming growth factor β (TGF-β) from bovine liver. Identification of the type V TGF-β receptor in cultured cells. *J. Biol. Chem.* 266, 8583-8589.

28. Huang, S. S., Liu, Q., Johnson, F. E., Konish, Y. and Huang, J. S. (1997) Transforming growth factor β peptide antagonists and their conversion to partial agonists. *J. Biol. Chem.* 272, 27155-27159.

29. FitzGerald, D. J., Fryling, C. M., Zdanovsky, A., Saelinger, C. B., Kounnas, M., Winkles, J. A., Strickland, D. and Leppla, S. (1995) Pseudomonas exotoxin-mediated selection yields cells with altered expression of low-density lipoprotein receptor-related protein. *J. Cell Biol.* 129, 1533-1541.

30. O'Grady, P., Liu, Q., Huang, S. S. and Huang, J. S. (1992) Transforming growth factor β (TGF-β) type V receptor has a TGF-β-stimulated serine/threonine-specific autophosphorylation activity. *J. Biol. Chem.* 267, 21033-21037.

31. Strickland, D. K., Ashcom, J. D., Williams, S., Burgess, W. H., Migliorini, M. and Argraves, W. S. (1990) Sequence identity between the $α_2$-macroglobulin receptor and low density lipoprotein receptor-related protein suggests that this molecule is a multifunctional receptor. *J. Biol. Chem.* 265, 17401-17404.

32. Herz, J. and Strickland, D. K. (2001) LRP: a multifunctional scavenger and signaling receptor. *J. Clin. Invest* 108, 779-784.

33. Herz, J., Goldstein, J. L., Strickland, D. K., Ho, Y. K. and Brown, M. S. (1991) 39-kDa protein modulates binding of ligands to low density lipoprotein receptor-related protein/$α_2$-macroglobulin receptor. *J. Biol. Chem.* 266, 21232-21238.

34. Gliemann, J., Nykjaer, A., Petersen, C. M., Jorgensen, K. E., Nielsen, M., Andreasen, P. A., Christensen, E. I., Lookene, A., Olivecrona, G. and Moestrup, S. K. (1994) The multiligand $α_2$-macroglobulin receptor/low density lipoprotein receptor-related protein ($α_2$MR/LRP). Binding and endocytosis of fluid phase and membrane-associated ligands. *Ann. N. Y. Acad. Sci.* 737, 20-38.

35. Krieger, M. and Herz, J. (1994) Structures and functions of multiligand lipoprotein receptors: macrophage scavenger receptors and LDL receptor-related protein (LRP). *Annu. Rev. Biochem.* 63, 601-637.

36. Strickland, D. K., Gonias, S. L. and Argraves, W. S. (2002) Diverse roles for the LDL receptor family. *Trends Endocrinol. Metab.* 13, 66-74.

37. Huang, S. S., O'Grady, P. and Huang, J. S. (1988) Human transforming growth factor β. $α_2$-macroglobulin complex is a latent form of transforming growth factor β. *J. Biol. Chem.* 263, 1535-1541.

38. Ziere, G. J., van der Kaaden, M. E., Vogelezang, C. J., Boers, W., Bihain, B. E., Kuiper, J., Kruijt, J. K. and van Berkel, T. J. (1996) Blockade of the $α_2$-macroglobulin receptor/low-density-lipoprotein-receptor-related protein on rat liver parenchymal cells by the 39-kDa receptor-associated protein leaves the interaction of β-migrating very-low-density lipoprotein with the lipoprotein remnant receptor unaffected. *Eur. J. Biochem.* 242, 703-711.

39. Willnow, T. E. and Herz, J. (1994) Genetic deficiency in low density lipoprotein receptor-related protein confers cellular resistance to Pseudomonas exotoxin A. Evidence that this protein is required for uptake and degradation of multiple ligands. *J. Cell Sci.* 107 (Pt 3), 719-726.

40. Laiho, M., Weis, M. B. and Massague, J. (1990) Concomitant loss of transforming growth factor (TGF)-β receptor types I and II in TGF-β-resistant cell mutants implicates both receptor types in signal transduction. *J. Biol. Chem.* 265, 18518-18524.

41. Howell, B. W., and Herz, J. (2001) The LDL receptor gene family: signaling functions during development. *Curr. Opin. Neurobiol.* 11, 74-81.

42. Lutz, C., Nimpf, J., Jenny, M., Boecklinger, K., Enzinger, C., Utermann, G., Baier-Bitterlich, G. and Bair, G. (2002) Evidence of functionaal modulation of the MEKKK/JNK/cjun signaling cascade by the low density lipoprotein receptor-related protein (LRP). *J. Biol. Chem.* 277, 43143-43151.

43. Penheiter, S. G., Mitchell, H., Garamszegi, N., Edens, M., Dore, J. J., Jr. and Leof, E. B. (2002) Intemalization-dependent and -independent requirements for transforming growth factor β receptor signaling via the Smad pathway. *Mol. Cell. Biol.* 22, 4750-4759.

44. Ravitz, M. J. and Wenner, C. E. (1997) Cyclin-dependent kinase regulation during $G_1$ phase and cell cycle regulation by TGF-β. *Adv. Cancer Res.* 71, 165-207.

45. Derrynck, R., Akhurst, R. J. and Balmain, A. (2001) TGF-β signaling in tumor supression and cancer progression. *Nat. Genet.* 29, 117-129.

46. Wakefield, L. M. and Roberts, A. B. (2002) TGF-β signaling: positive and negative effects on tumorigenesis. *Cur. Opin. Genet. Dev.* 12, 22-29.

47. Santner, S. J., Dawson, P. J., Tait, L., Soule, H. D., Eliason, J., Mohamed, A. N., Wolman, S. R., Heppner, G. H. and Miller, F. R. (2001) Malignant MCF10CA1 cell lines derived from premalignant human breast epithelial MCF10AT cells. *Breast Cancer Res. Treat.* 65, 101-110.

48. Tang, B., Yu, M., Booker, T., Anver, M. R., Santner, S. J., Miller, F. R., Wakefield, L. M. (2003) Transforming growth factor-β (TGF-β) switches from tumor suppressor to prometastatic factor in late-stage breast cancer. AACR Special Conference "The TGF-β Superfamily: Roles in the pathogenesis of cancer and other diseases." Conference Proceedings.

49. Van Leuven, F., Cassiman, J. J. and Van Den, B. H. (1979) Demonstration of an $\alpha_2$-macroglobulin receptor in human fibroblasts, absent in tumor-derived cell lines. *J. Biol. Chem.* 254, 5155-5160.

50. Gonias, S. L., LaMarre, J., Crookston, K. P., Webb, D. J., Wolf, B. B., Lopes, M. B., Moses, H. L. and Hayes, M. A. (1994) $\alpha_2$-macroglobulin and the $\alpha_2$-macroglobulin receptor/LRP. A growth regulatory axis. *Ann. N. Y. Acad. Sci.* 737, 273-290.

51. Li, Y., Wood, N., Parsons, P. G., Yellowlees, D. and Donnelly, P. K. (1997) Expression of $\alpha_2$-macroglobulin receptor/low density lipoprotein receptor-related protein on surfaces of tumour cells: a study using flow cytometry. *Cancer Letts.* 111, 199-205.

52. Yamamoto, M., Ikeda, K., Ohshima, K., Tsugu, H., Kimura, H. and Tomonaga, M. (1997) Increased expression of low density lipoprotein receptor-related protein/$\alpha_2$-macroglobulin receptor in human malignant astrocytomas. *Cancer Res.* 57, 2799-2805.

53. Koong, A. C., Denko, N. C., Hudson, K. M., Schindler, C., Swiersz, L., Koch, C., Evans, S., Ibrahim, H., Le, Q. T., Terris, D. J. and Giaccia, A. J. (2000) Candidate genes for the hypoxic tumor phenotype. *Cancer Res.* 60, 883-887.

54. Massague, J. (1990) *Annu. Rev. Cell Biol.* 6, 597-641.

55. Roberts, A. B. a. S., M.B. (1990) in *Handbook of experimental Pharmacology: Peptide Growth Factors and Their Receptors*, M. B. Sporn and A. B. Roberts, eds(New York: Springer-Verlag), 419-472.

56. Roberts, A. B., and Sporn, M. B. (1993) *Growth Factors* 8, 1-9.

57. Roberts, A. B. (1998) *Miner. Electrolyte Metab.* 24, 111-119.

58. Wang, J., Han, W., Zborowska, E., Liang, J., Wang, X., Willson, J. K., Sun, L., and Brattain, M. G. (1996) *J. Biol. Chem.* 271, 17366-17371.

59. Leal, S. M., Liu, Q., Huang, S. S., and Huang, J. S. (1997) *J. Biol. Chem.* 272, 20572-20576.

60. Taipale, J., and Keski-Oja, J. (1996) *J. Biol. Chem.* 271, 4342-4348.

61. Chakrabarty, S., Rajagopal, S., and Moskal, T. L. (1998) *Lab. Invest.* 78, 413-421.

62. Heldin, N. E., Bergstrom, D., Hermansson, A., Bergenstrahle, A., Nakao, A., Westermark, B., and ten Dijke, P. (1999) *Mol. Cell. Endocrinol.* 153, 79-90.

63. Donovan, J. C., Rothenstein, J. M., and Slingerland, J. M. (2002) *J. Biol. Chem.* 277, 41686-41692.

64. Heldin, C. H., Miyazono, K., and ten Dijke, P. (1997) *Nature.* 390, 465-471.

65. Massague, J. (1998) *Annu. Rev. Biochem.* 67, 753-791.

66. Howe, P. H., Bascom, C. C., Cunningham, M. R., and Leof, E. B. (1989) *Cancer Res.* 49, 6024-6031.

67. Howe, P. H., Cuningham, M. R., and Leof, E. B. (1990) *Biochem. J.* 266, 537-543.

68. Hocevar, B. A., and Howe, P. H. (1998) *Miner. Electrolyte Metab.* 24, 131-135.

69. Petritsch, C., Beug, H., Balmain, A., and Oft, M. (2000) *Genes Dev.* 14, 3093-3101.

70. Massagué, J. (1992) *Cell* 69, 1067-1070.

71. Yingling, J. M., Wang, X.-F., and Bassing, C. H. (1995) *Biochem. Biophys. Acta.* 242, 168-136.

72. Blobe, G. C., Liu, X., Fang, S. J., How, T., and Lodish, H. F. (2001) *J. Biol. Chem.* 276, 39608-39617.

73. Blobe, G. C., Schiemann, W. P., Pepin, M. C., Beauchemin, M., Moustakas, A., Lodish, H. F., and O'Connor-McCourt, M. D. (2001) *J. Biol. Chem.* 276, 24627-24637.

74. Eickelber, O., Centrella, M., Reiss, M., Kashgarian, M., and Wells, R. G. (2002) *J. Biol. Chem.* 277, 823-829.

75. Yamashita, H., Okadome, T., Franzen, P., ten Dijke, P., Heldin, C. H., and Miyazono, K. (1995) *J. Biol. Chem.* 270, 770-774.

76. Moustakas, A., Takumi, T., Lin, H. Y., and Lodish, H. F. (1995) *J. Biol. Chem.* 270, 765-769.

77. O'Grady, P., Kuo, M.-D., Baldassare, J. J., Huang, S. S., and Huang, J. S. (1991) *J. Biol. Chem.* 266, 8583-8589.

78. O'Grady, P., Huang, S. S., and Huang, J. S. (1991) *Biochem. Biophys. Res. Comm.* 179, 378-385.

79. Liu, Q., Huang, S. S., and Huang, J. S. (1994) *J. Biol. Chem.* 269, 9221-9226.

80. Leal, S. M., Huang, S. S., and Huang, J. S. (1999) *J. Biol. Chem.* 274, 6711-6717.

81. Wu, H. B., Kumar, A., Tsai, W. C., Mascarenhas, D., Healey, J., and Rechler, M. M. (2000) *J. Cell. Biochem.* 77, 288-297.

82. Huang, S. S., Ling, T.-Y., Tseng, W.-F., Huang, Y.-H., Yen, H.-Y., Leal, S. M., and Huang, J. S. (2003) Submitted for publication.

83. Herz, J., and Strickland, D. K. (2001) *J. Clin. Invest.* 108, 779-784.

84. Strickland, D. K., Gonias, S. L., and Argraves, W. S. (2002) *Trends Endocrinol. Metab.* 13, 66-74.

85. Huang, S. S., Liu, Q., Johnson, F. E., Konish, Y., and Huang, J. S. (1997) *J. Biol. Chem.* 272, 27685-27689.

86. Clemmons, D. R. (1992) *Growth Regul.* 2, 80-87.

87. Oh, Y., Gargosky, S. E., Lehmbecher, T., Hintz, R. L., and Rosenfeld, R. G. (1993) *J. Clin. Endocrinol. Metab.* 77, 1113-1119.

88. Valentinis, B., Bhala, A., DeAngelis, T., Baserga, R., and Cohen, P. (1995) *Mol. Endocrinol.* 9, 361-367.

89. Cascieri, M. A., Hayes, N. S., and Bayne, M. L. (1989) *J. Cell. Physiol.* 139, 181-188.

90. Gagnon, A. M., Chabot, J., Pardasani, D., and Sorisky, A. (1998) *J. Cell. Physiol.* 175, 370-378.

91. Ayaki, M., Mukai, M., Imamura, F., Iwasaki, T., Mammoto, T., Shinkai, K., Nakamura, H., and Akedo, H. (2000) *Biochim. Biophys. Acta* 1495, 40-50.

92. White, M. F. (2002) *Am. J. Physiol.* 283, E413-422.

93. Myers, M. G., Jr., and White, M. F. (1996) *Annu. Rev. Pharmacol. Toxicol.* 36, 668-658.

94. Saudan, P., Vlach, J., and Beard, P. (2000) *EMBO J.* 19, 4351-4361.

95. Joung, I., Kim, T., Stolz, L. A., Payne, G., Winkler, D. G., Wash, C. T., Strominger, J. L., and Shin, J. (1995) *Proc. Natl. Acad. Sci. USA* 92, 5778-5782.

96. Leal, S. M. (1999) Ph.D. Dissertation, St. Louis University.

97. McCluskey, A., Sim, A. T., and Sakoff, J. A. (2002) *J. Med. Chem.* 45, 1681-1175.

98. Laiho, M., Weis, F. M. B., and Massagué, J. (1990) *J. Biol. Chem.* 265, 18518-18524.

99. Dore, J. J., Jr., Edens, M., Garamszegi, N., and Leof, E. B. (1998) *J. Biol. Chem.* 273, 31770-31777.

100. Ricort, J. M., and Binoux, M. (2002) *J. Biol. Chem.* 277, 19448-19454.

101. Khan, M. N., Baquiran, G., Brule, C., Burgess, J., Foster, B., Bergeron, J. J., and Posner, B. I. (1989) *J. Biol. Chem.* 264, 12931-12940.

102. Ricort, J. M., Tanti, J. F., Van Obberghen, E., and Le Marchand-Brustel, Y. (1995) *Diabetologia* 38, 1148-1686.

103. Kroder, G., Bossenmaier, B., Kellerer, M., Capp, E., Stoyanov, B., Muhlhofer, A., Berti, L., Horikoshi, H., Ullrich, A., and Haring, H. (1996) *J. Clin. Invest.* 97, 1471-1477.

104. Haystead, T. A., Weiel, J. E., Litchfield, D. W., Tsukitani, Y., Fischer, E. H., and Krebs, E. G. (1990) *J. Biol. Chem.* 265, 16571-16580.

105. Qiao, L. Y., Zhande, R., Jetton, T. L., Zhou, G., and Sun, X. J. (2002) *J. Biol. Chem.* 277, 26530-26539.

106. Peraldi, P., Hotamisligil G S., Buurman, W A., White, M F., Spiegelman, B M. (1996) *J. Biol. Chem.*271, 13081-13022.

107. Huang, S. S., and Huang, J. S. unplished result.

108. Piek, E., and Roberts, A. B. (2001) *Adv. Cancer Res.* 83, 1-54.

109. Baxter, R. C., and Martin, J. L. (1989) *Prog. Growth Factor Res.* 1, 49-68.

110. Conover, A., Hintz, R. L., and Rosenfeld, R. G. (1989) *Horm. Metab. Res.* 21, 59-63.

111. Clemmons, D. R., Dehoff, M. L., Busby, W. H., Bayne, M. L., and Cascieri, M. A. (1992) *Endocrinology* 131, 890-895.

112. Oh, Y., Gucev, Z., Ng, L., Muller, H. L., and Rosenfeld, R. G. (1995) *Prog. Growth Factor Res.* 6, 503-512.

113. Kelley, K. M., Oh, Y., Gargosky, S. E., Gucev, Z., Matsumoto, T., Hwa, V., Ng, L., Simpson, D. M., and Rosenfeld, R. G. (1996) *Int. J. Biochem. Cell Biol.* 28, 619-637.

114. Li, J., DeFea, K., and Roth, R. A. (1999)*J. Biol. Chem.* 274, 9351-9356.

115. Paz, K., Liu, Y. F., Shorer, H., Hemi, R., LeRoith, D., Quan, M., Kanety, H., Seger, R., and Zick, Y. (1999) *J. Biol. Chem.* 274, 28816-28822.

116. Liu, Q., Huang, S. S., and Huang, J. S. (1997) *J. Biol. Chem.* 272, 18891-18895.

SUMMARY OF THE INVENTION

The inventor has made the surprising discovery that the type V TGF-β receptor ("TβR-V"), which is a receptor for transforming growth factor β ("TGF-β") and insulin like growth factor binding protein ("IGFBP"), is the same as the low density lipoprotein receptor-related protein ("LRP"), revealing for the first time the true and complete molecular structure of TβR-V. To date there have been no reports in the art that TGF-β or IGFBP can bind to LRP. It is known in the art that growth inhibitory effects of IGFBP and TGFβ are mediated through TβR-V signaling, thus it is disclosed for the first time that LRP mediates growth inhibitory effects of TGF-β and IGFBP.

The inventor has also discovered that LRP minichromosomes (mLRP-I, mLRP-II, mLRP-III, mLRP-IV; see Bu and Rennke, *J. Biol. Chem.* 271:22218-22224 (1996) for a description of SLRPs, which are equivalent to the instant disclosed mLRPs), which are soluble subunits of the LRP heavy chain, function as dominant negative LRP molecules. The mLRPs I-IV effectively inhibit transduction of the TGF-β- or IGFBP-mediated inhibition of cell proliferation through LRP.

The inventor has also discovered that LRP has a high-density acidic pH binding site for TGF-β (as well as $α_2M^*$). This binding site also mediates annexin-VI binding and subsequent internalization and degradation of TGF-β. Furthermore, it was discovered that the drugs trifluoperazine and fluphenazine (et alia, infra) inhibit ligand binding to the acidic site and block internalization and subsequent degredation of surface bound TGF-β.

The inventor has also made the surprising discovery that an insulin receptor substrate protein ("IRS-1", "IRS-2") can mediate the growth inhibitory response of cells to TGF-β or IGFBP, in part through the LRP/TβR-V signaling pathway. Heretofore, the IRS proteins were known only to mediate the mitogenic effects of insulin, IGF-1, and a few other cytokines, in part by activating the phosphatidylinositol 3' kinase pathway.

The discovery of these important drugs, agents, and molecular components of the TGF-β/IGFBP cell growth inhibitory response signaling pathway now enables one skilled in the art to alter or control the growth response of cells to LRP ligands. This discovery also enables the identification of small molecules, biological molecules or other agents that mimic, agonize, antagonize or otherwise affect cell growth signaling through the LRP/TβR-V pathway.

Methods of Inhibiting Cell Proliferation

Therefore, an object of the invention is a method of inhibiting cell proliferation, preferably (but not limited to) cells that are recalcitrant to the growth inhibitory effects of TGF-β or IGFBP (such as certain types of cancer cells), by contacting the cell with a LRP ligand and a LRP polypeptide or a LRP polynucleotide. In another embodiment, the invention is drawn to compositions comprising an isolated LRP ligand and an isolated LRP polypeptide or LRP polynucleotide. A preferred LRP polypeptide has a sequence set forth as accession number NP_002323 in the publicly available GenBank database. A preferred LRP polynucleotide has a sequence set forth in GenBank as accession number NM_002332. Other LRP molecules may be used in the practice of this invention. Preferred LRP ligands include TGF-β (more preferably TGF-β1) and IGFBP (more preferably IGFBP-3).

In another embodiment, the method comprises contacting a cell with an agent which inhibits endocytotic trafficking of TGF-β, IGFBP or other LRP ligand. Preferred agents include phenothiozine-related compounds (e.g., trifluoperazine, fluphenazine, promethazine, and derivatives thereof), transglutaminase inhibitors (e.g., monodansylcardaverine), calmodulin antagonists (e.g., W-7) and substances that interfere with annexin VI expression (e.g., anti-annexin VI antibodies or Fabs).

In yet another embodiment, the method comprises contacting the cell with a LRP ligand and a receptor substrate. In another embodiment, the invention is drawn to compositions comprising an isolated LRP ligand and an isolated receptor substrate. Preferred receptor substrates are insulin receptor substrates 1 and 2 ("IRS-1" and "IRS-2") or polynucleotides that encode IRS-1 and IRS2. Preferred LRP ligands include TGF-β (more preferably TGF-β1) and IGFBP (more preferably IGFBP-3).

Since some cell types, such as mesenchymal-cell-derived cancers, like glioma, respond to TGF-β or IGFBP by proliferating, another object of the invention is a method of inhibiting cell proliferation by contacting the cell with a LRP associated protein ("RAP") polypeptide or a RAP polynucleotide. A preferred RAP polypeptide has a sequence set forth under accession number NP_002328. A preferred RAP polynucleotide has a sequence set forth under accession number NM_002337. Other RAP molecules may be used in the practice of this invention.

Methods of Promoting Cell Proliferation

Another object of the invention is a method of promoting cell proliferation by interfering with LRP-mediated inhibition of cell proliferation. In one embodiment, a cell is contacted with a LRP associated protein ("RAP") polypeptide or a RAP polynucleotide. A preferred RAP polypeptide has a sequence set forth under accession number NP_002328. A preferred RAP polynucleotide has a sequence set forth under accession number NM_002337. Other RAP molecules may be used in the practice of this invention.

In another embodiment, the method comprises contacting a cell with an integrin antagonist and an insulin receptor ligand. Preferred integrin antagonists include cyclic RGD and cycloGRGDSPA. Preferred insulin receptor ligands include insulin, IGF-1 and $(Q^3A^4Y^{15}L^{16})$ IGF-1.

In yet another embodiment, the method comprises contacting a cell with a LRP dominant negative molecule. Preferred LRP dominant negative molecules include LRP-1 heavy chain "minireceptors" and polynucleotides encoding same. Preferred minireceptors include mLRP-I (~120 kDa mass), mLRP-II (~160 kDa mass), mLRP-III (~200 kDa mass), mLRP-IV (~160 kDa mass), and their encoding polynucleotides.

Methods of Treatment

Another object of the invention is a method of treating cancer, comprising administering to a patient a therapeutically effective amount of a composition comprising (a) a TGF-β (or polynucleotide encoding same) and a LRP (or polynucleotide encoding same), (b) an IGFBP (or polynucleotide encoding same) and a LRP (or polynucleotide encoding same), (c) a TGF-β (or polynucleotide encoding same) and an anti-annexin VI antibody (or fragment thereof), (d) an IGFBP (or polynucleotide encoding same) and an annexin VI antibody (or fragment thereof), (e) an annexin VI antibody or fragment thereof, (f) a TGF-β (or polynucleotide encoding same) and an agent which inhibits endocytotic trafficking of TGF-β, IGFBP or other LRP ligand (supra), (g) an IGFBP (or polynucleotide encoding same) and an agent which inhibits endocytotic trafficking of TGF-β, IGFBP or other LRP ligand (supra), (h) a RAP molecule (polypeptide or encoding polynucleotide), (i) a LRP dominant negative molecule (e.g., LRP minireceptor [mLRPI, -II, -III, -IV] or encoding polynucleotide), or (j) an insulin-receptor agonist (e.g., insulin or IGF-1) and an integrin antagonist, such that cancer cell proliferation is inhibited.

Another object of the invention is a method of treating insulin-mediated diseases such as diabetes and obesity, TGF-β-mediated diseases such as fibroses and cancer or a combination of insulin-mediated and TGF-β-mediated diseases such as abnormal wound healing associated with diabetes. Compositions useful in treating those diseases may comprise any one or more of TGF-β, IGFBP-3, RAP, IRS-1, IRS-2, insulin, IGF-1, $(Q^3A^4Y^{15}L^{16})$ IGF-1, integrin, RGD, cyclic RGD, cycloGRGDSPA, an agent which inhibits TGF-β binding to LRP (supra), or a LRP dominant negative molecule (supra).

Other Objects

Another object of the invention is a method of modulating the phosphorylation state of IRS proteins (e.g., IRS-1, IRS-2). In one embodiment, serine dephosphorylation of an IRS protein is promoted by contacting a cell with IGFBP or similar LRP agonist. In another embodiment, serine phosphorylation of an IRS protein is promoted by contacting a cell with TGF-β or similar LRP agonist. The modulation of the phosphorylation status of IRS protein is useful in manipulating cellular responses to TGF-β or insulin/IGF-1 and of treating insulin-mediated diseases such as type 1 and type 2 diabetes.

Another object of the invention is a method and kit useful for the identification of an agent that modulates the cell growth signal transduction activity of LRP. In one embodiment, the method or kit comprises (a) combining a LRP ligand (preferred ligands are TGF-β, IGFBP or fragments thereof) with a candidate agent (the agent may be any substance; preferred agents are small organic molecules, biological molecules, pharmaceutical compounds or the like) and a LRP molecule (in a preferred embodiment, the LRP molecule is expressed on the surface of a cell) together in a sample, (b) detecting the level of LRP activity (preferred LRP activities include modulation of cell proliferation, modulation of DNA synthesis, modulation of IRS protein phosphorylation state, ligand binding—competitive—to LRP) in the sample, and (c) comparing the level of LRP activity in the sample to a standard level of LRP activity (a preferred standard would be similar to the sample, but without either the candidate agent or the LRP ligand). Those agents found to be effective in modulating LRP activity may be useful in the treatment of those insulin/IGF-1-mediated or TGF-β-mediated diseases.

Another object of the invention is an epithelial cell comprising a mutation which reduces the LRP activity or expression. A preferred cell includes a PEA-C11 cell (infra) or CHO-LRP-1 cell (infra).

BRIEF DESCRIPTION OF THE DRAWINGS

FIG. 7 depicts the effect of TGF-$\beta_1$ on DNA synthesis (A), cell growth (B) and PAI-1 expression (C) in MEF and PEA-13 cells. (A) Cells were treated with various concentrations of TGF-$\beta_1$ as indicated. DNA synthesis was determined by measuring [methyl-$^3$H] thymidine incorporation into cellular DNA. The [methyl-$^3$H] thymidine incorporation in cells treated without TGF-$\beta_1$ (100,861±3,720 and 103,262±6,722 cpm/well for MEF and PEA-13 cells, respectively) was taken as 0% inhibition. The negative values of inhibition indicate mitogenic activity. For example, −20% inhibition means 20% higher [methyl-$^3$H] thymidine incorporation than that in the control cells (treated without TGF-$\beta_1$). Each datapoint is the mean±S.D. of quadruplicate determinations. The DNA synthesis inhibition in PEA-C11 cells was significantly different at all data points (except 0 concentration of TGF-$\beta_1$) when compared with MEF cells (Student's t test, p<0.001). Data are representative of six similar experiments. (B) Cells were treated with various concentrations of TGF-$\beta_1$ as indicated. The cell number was counted after a 4 day incubation. The cell numbers in cells treated without TGF-$\beta_1$ (13±2 and 9±2×

$10^4$ cells for MEF and PEA-13 cells, respectively) were taken as 0% inhibition. The negative values of the inhibition indicate the growth stimulatory activity. Each datapoint is the mean±S.D. of quadruplicate determinations. The DNA synthesis inhibition in PEA-C11 cells was significantly different at all data points (except 0 concentration of TGF-$\beta_1$) when compared with MEF cells (Student's t test, p<0.001). Data are representative of four similar experiments. (C) Cells were treated with various concentrations of TGF-$\beta_1$ as indicated. The PAI-1 expression in these cells was determined by Northern blot analysis. The expression of G3PDH was used as control. The relative levels of the transcripts were quantified by a PhosphoImager. Data are representative of four similar experiments.

Figure 8:
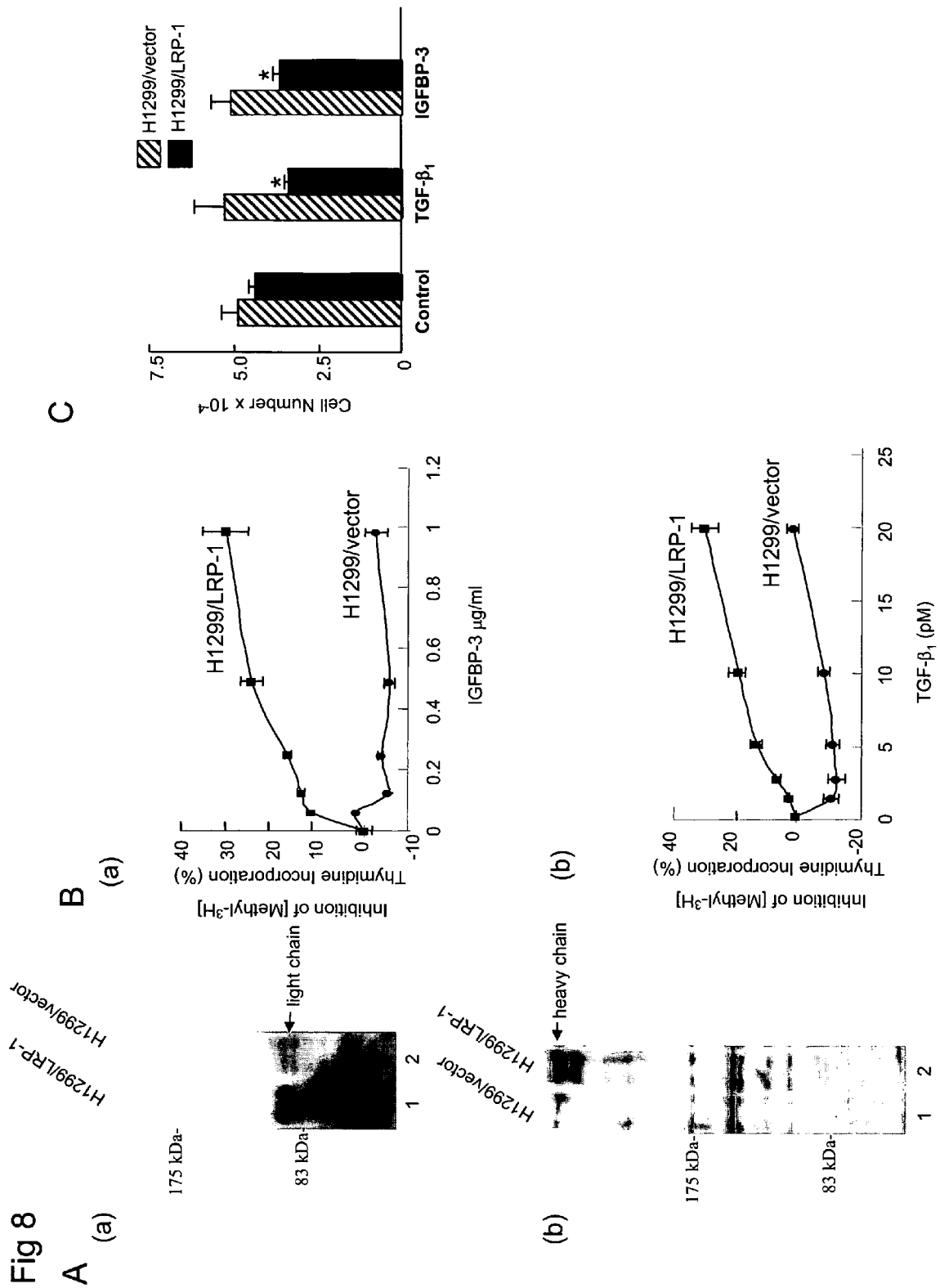

FIG. 8 depicts a Western blot analysis of LRP-1 (A) and effects of IGFBP-3 and TGF-$\beta_1$ on DNA synthesis (B) and cell growth (C) in H1299LRP-1 and H1299/vector cells. (A) Equal amounts of protein from the cell lysates of H1299/LRP-1 and H1299/vector cells were subjected to Western blot analysis using antisera to LRP-1 light chain (a) and heavy chain (b) following 7.5 and 5% SDS-PAGE under non-reducing conditions and electrophoretic transblot. The relative intensities of the LRP-1 light chain and heavy chain were quantitated by densitometry. Data are representative of four similar experiments. (B,C) Cells were incubated with various concentrations of IGFBP-3 and TGF-$\beta_1$ as indicated. The DNA synthesis of these cells was determined by estimating [methyl-$^3$H] thymidine incorporation into cellular DNA (B). The [methyl-$^3$H] thymidine incorporation into DNA in cells treated without IGFBP-3 (a) and TGF-$\beta_1$ (b) (137,541±2,537 and 81,787±696 cpm/well for H1299/vector and H1299/LRP-1 cells, respectively) was taken as 0% inhibition. For cell growth assay, cells were plated at a cell density of $1\times10^4$ cells/dish containing 1% fetal calf serum with or without TGF-$\beta_1$ (20 pM) or IGFBP-3 (1 µg/ml). The cell number was counted after a 3-day incubation (C). The bars represent the mean±S.D. of quadruplicate determinations. Data from H1299/LRP-1 cells were compared with data from H1299/vector cells by Student's t test. The asterisk (*) indicates p<0.01. Data are representative of four to eight similar experiments.

Figure 9:
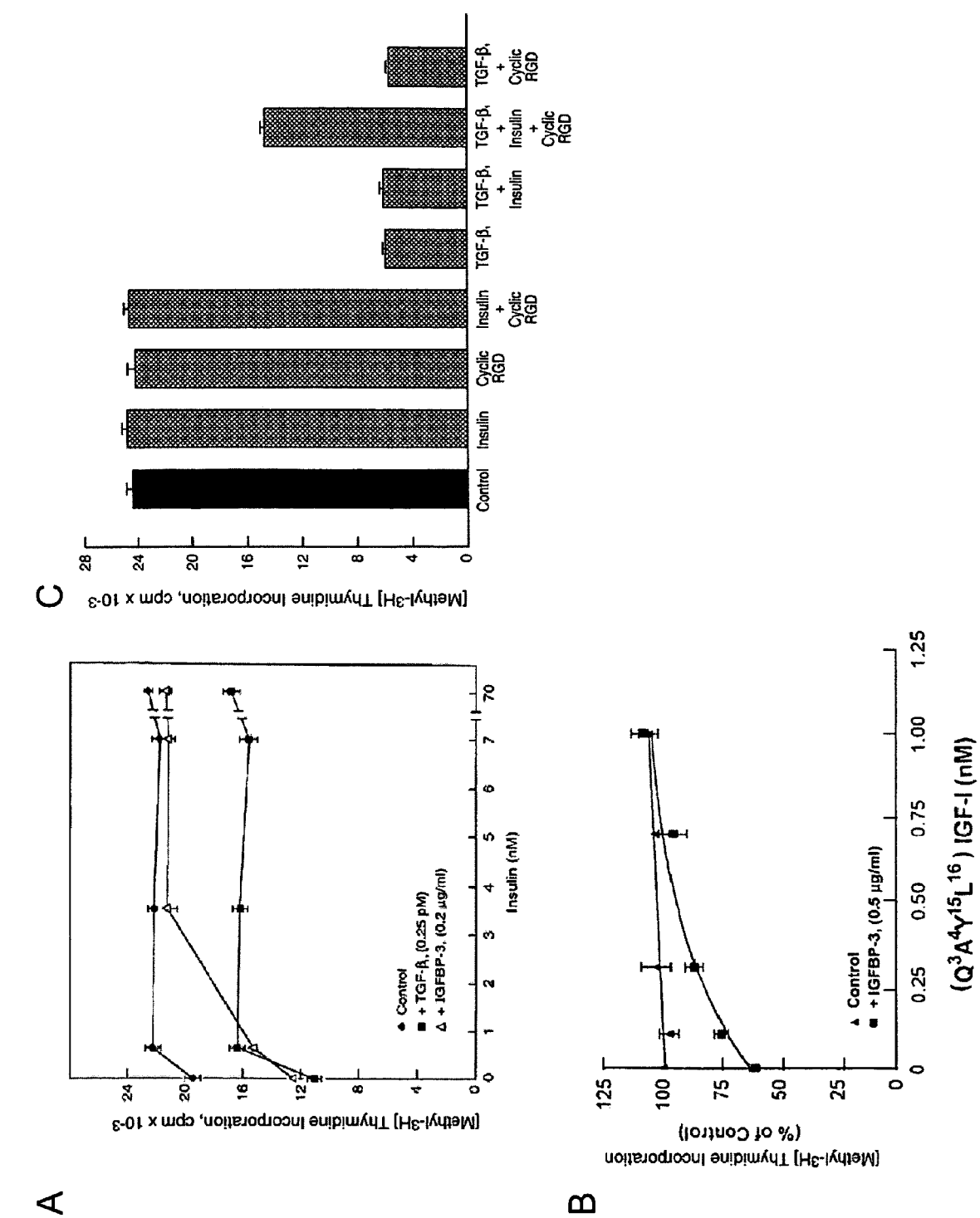

FIG. 9 depicts the effects of insulin and $(Q^3A^4Y^{15}L^{16})$ IGF-I on DNA synthesis in Mv1Lu cells treated with IGFBP-3 or TGF-$\beta_1$ in the absence (A,B) and presence (C) of a cyclic RGD peptide. (A,B) Cells were treated with 0.2 (A) or 0.5 g/ml (B) of IGFBP-3 in the presence of various concentrations (as indicated) of insulin or $(Q^3A^4Y^{15}L^{16})$ IGF-I. After 18 hr at 37EC, DNA synthesis was determined by measuring [methyl-$^3$H] thymidine incorporation into cellular DNA. The [methyl-$^3$H] thymidine incorporation in cells treated with insulin or $(Q^3A^4Y^{15}L^{16})$ IGF-I in the absence of IGFBP-3 was taken as 100% of DNA synthesis. Each data point is the mean±S.D. of quadruplicate determinations in four independent experiments. (C) Cells were treated with and without TGF-$\beta_1$ (0.5 pM)±insulin (10 nM)±a cyclic RGD peptide (Cyclo GRGDSPA, 0.01 µg/ml) for 18 hr at 37° C. The [methyl-$^3$H] thymidine incorporation into cellular DNA was determined. The bars represent the mean±S.D. of triplicate determinations in four independent experiments.

Figure 10:

FIG. 10 depicts IGFBP-3-induced increased electrophoretic mobility (A,B) and phosphoamino acid analysis (C) of $^{85}$P-labeled IRS-1 and IRS-2 in Mv1Lu cells. (A,B) Cells metabolically labeled with $^{85}$P-orthophosphate were treated with or without 1:g/ml of IGFBP-3 at 147 EC for 14 hr. The $^{85}$P-labeled cell lysates were immunoprecipitated with anti-IRS-1 (A) or anti-IRS-2 (B) IgG. The immunoprecipitates were analyzed by 7.5% SDS-PAGE and autoradiography. The closed and open arrows indicate the location of the 160-kDa $^{85}$P-labeled IRS-1 or 170-kDa $^{85}$P-labeled IRS-2 and their faster-migrating forms, respectively. (C) $^{85}$P-labeled IRS-2 from cells treated with or without IGFBP-3 was excised from the SDS-polyacrylamide gel shown in (B) and subjected to acid hydrolysis and phosphoamino acid analysis using one dimensional thin-layer cellulose electrophoresis. The arrow indicates the locations of $^{85}$P-orthophosphate and standard phosphoserine (P-Ser), phosphothreonine (P-Thr) and phosphotyrosine (P-Tyr). The asterisk indicates the locations of partially hydrolyzed peptides.

Figure 11:
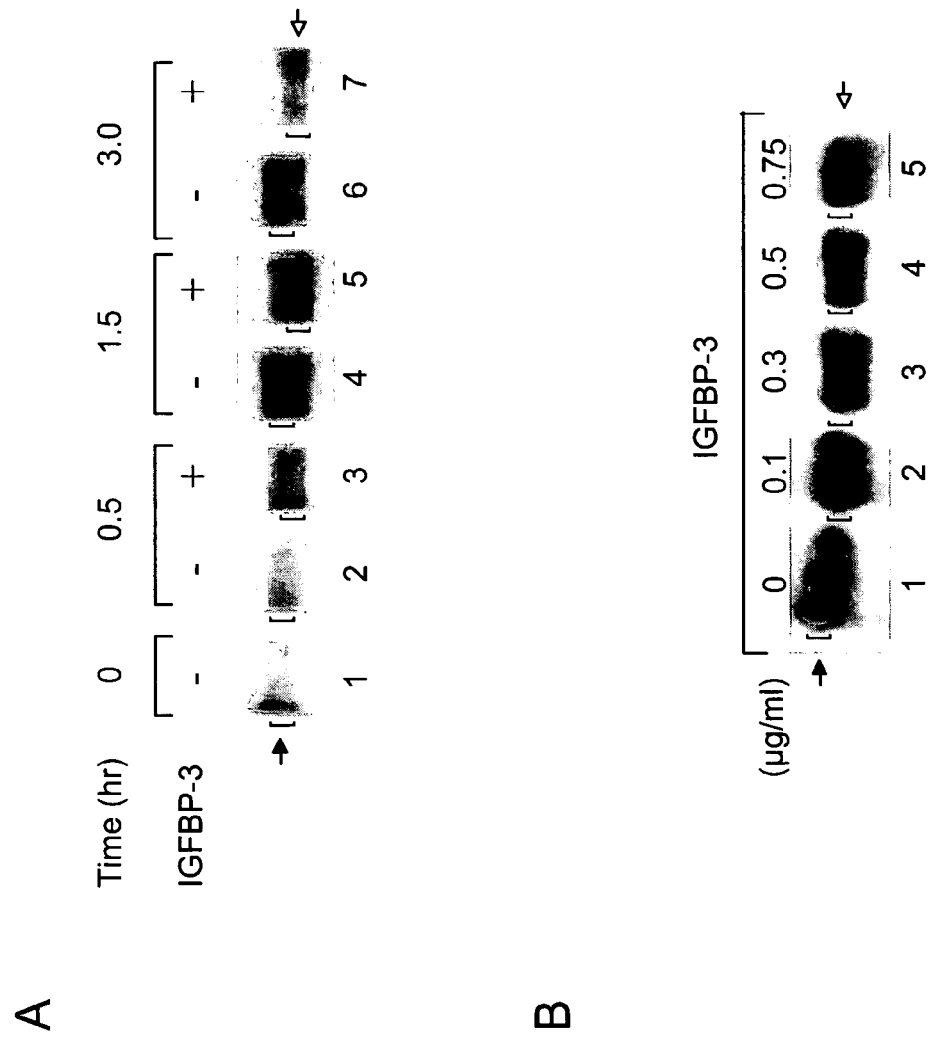

FIG. 11 depicts the kinetics (A) and concentration dependence (B) of IGFBP-3-induced increased electrophoretic mobility of $^{85}$P-labeled IRS-2 in Mv1Lu cells. (A) Cells metabolically labeled with $^{85}$P-orthophosphate were treated with IGFBP-3 (1 µg/ml) for different time periods as indicated. $^{85}$P-labeled cell lysates were immunoprecipitated with anti-IRS-2 IgG. The immunoprecipitates were analyzed by SDS-PAGE under reducing conditions and autoradiography. The closed and open arrows indicate the locations of 85P-labeled IRS-2 and its faster-migrating form, respectively. The relative intensity of $^{85}$P-labeled IRS-2 was quantitated with a PhosphoImager. (B) Cells metabolically labeled with 85P-orthophosphate were treated with various concentrations of IGFBP-3 as indicated. After 14 hr at 37° C., the $^{85}$P-labeled IRS-2 in the cell lysates was immunoprecipitated with anti-IRS-2 IgG. The immunoprecipitates were analyzed by 7.5% SDS-PAGE under reducing conditions and autoradiography. The closed and open arrows indicate the locations of $^{85}$P-labeled IRS-2 and its faster-migrating form, respectively.

Figure 12:
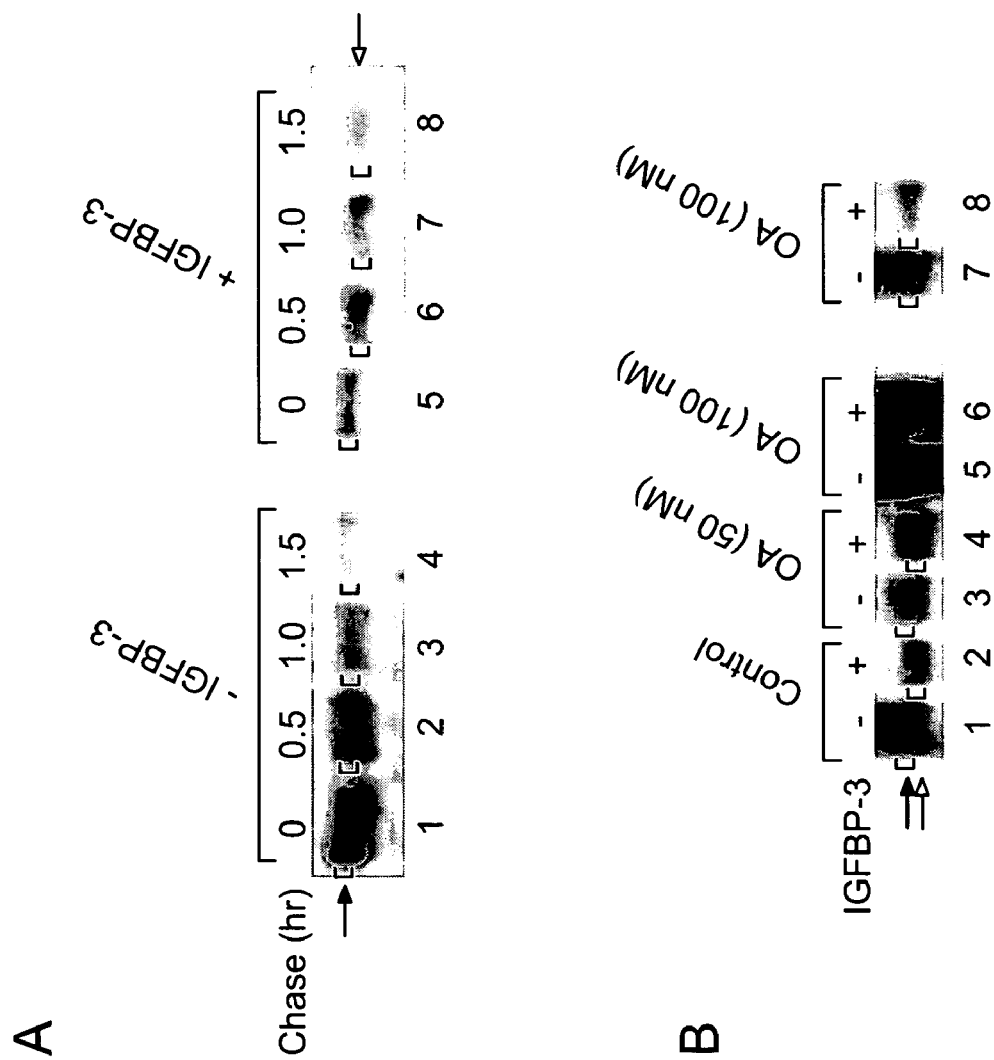

FIG. 12 depicts kinetic (A) and okaidic acid sensitivity (B) of specific dephosphorylation of 85P-labeled IRS-2 in Mv1Lu cells treated with IGFBP-3. (A) Cells were pulse-labeled with $^{85}$P-orthophosphate for 14 hr and chased with unlabeled orthophosphate in the presence and absence of IGFBP-3 (1 µg/ml) for different time periods as indicated. At each time period, the $^{85}$P-labeled IRS-2 was immunoprecipitated and analyzed by 7.5% SDS-PAGE under reducing conditions and autoradiography. The closed and open arrows indicate the locations of $^{85}$P-labeled IRS-2 and its fast-migrating form, respectively. (B) Cells metabolically labeled with 85P-orthophosphate were treated with IGFBP-3 (1 µg/ml) in the presence of various concentrations (50 and 100 nM) of okaidic acid (OA) (lanes 1-6). After 14 hr at 37° C., the 85P-labeled IRS-2 was immunoprecipitated and analyzed by 7.5% SDS-PAGE under reducing conditions and autoradiography. The closed and open arrows indicate the locations of $^{85}$P-labeled IRS-2 and its faster-migrating form, respectively. Lanes 7 and 8 (treated with 100 nM OA) are the same autoradiogram of lanes 5 and 6 but with less exposure time.

Figure 13:
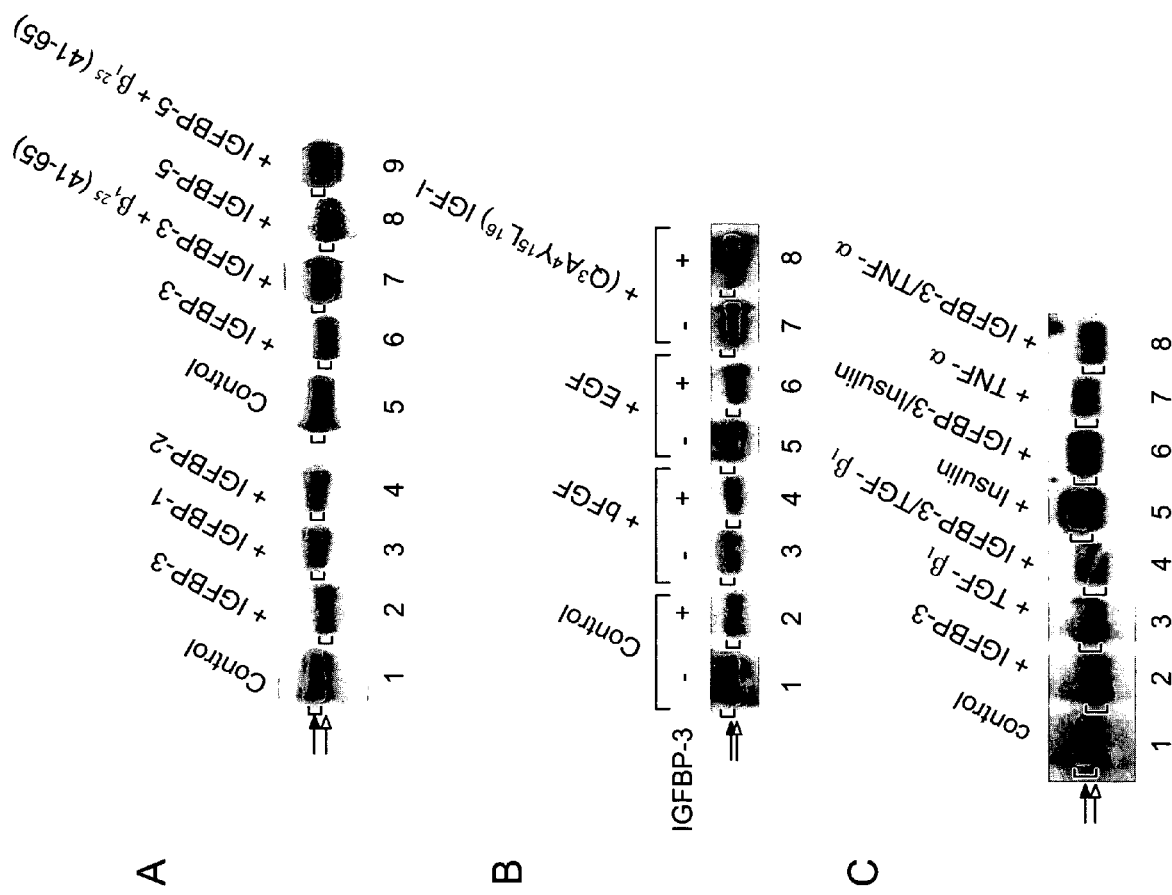

FIG. 13 depicts the inability of IGFBP-1 and IGFBP-2 (A) to induce specific dephosphorylation of IRS-2 and effects of insulin, $(Q^3A^4Y^{15}L^{16})$ IGF-I and other growth factors/cytokines (B,C,D) on IGFBP-3-induced specific dephosphorylation of 85P-labeled IRS-2 in Mv1Lu cells. (A) Cells metabolically labeled with $^{85}$P-orthophosphate were treated with 1 µg/ml of IGFBP-1 or IGFBP-2 for 14 hr at 37° C. The 85P-labeled IRS-2 was immunoprecipitated and analyzed by 7.5% SDS-PAGE under reducing conditions and autoradiography. The closed and open arrows indicate the locations of $^{85}$P-labeled IRS-2 and its faster-migrating form, respectively. (B,C,D) Cells metabolically labeled with 85P-orthophosphate were treated with or without IGFBP-3 (1 µg/ml) for 2.5 hr at 37° C. and then treated with insulin (10 nM), $(Q^3A^4Y^{15}L^{16})$ IGF-I (10 nm), EGF (10 nm), bFGF (10 nM), TGF-$\beta_1$ (20 pM) or TNFα (10 nM) for 0.5 hr. The $^{85}$P-labeled IRS-2 was immunoprecipitated and analyzed by 7.5% SDS- PAGE under reducing conditions and autoradiography. The closed and open arrows indicate the locations of $^{85}$P-labeled IRS-2 and its faster-migrating form.

Figure 14:
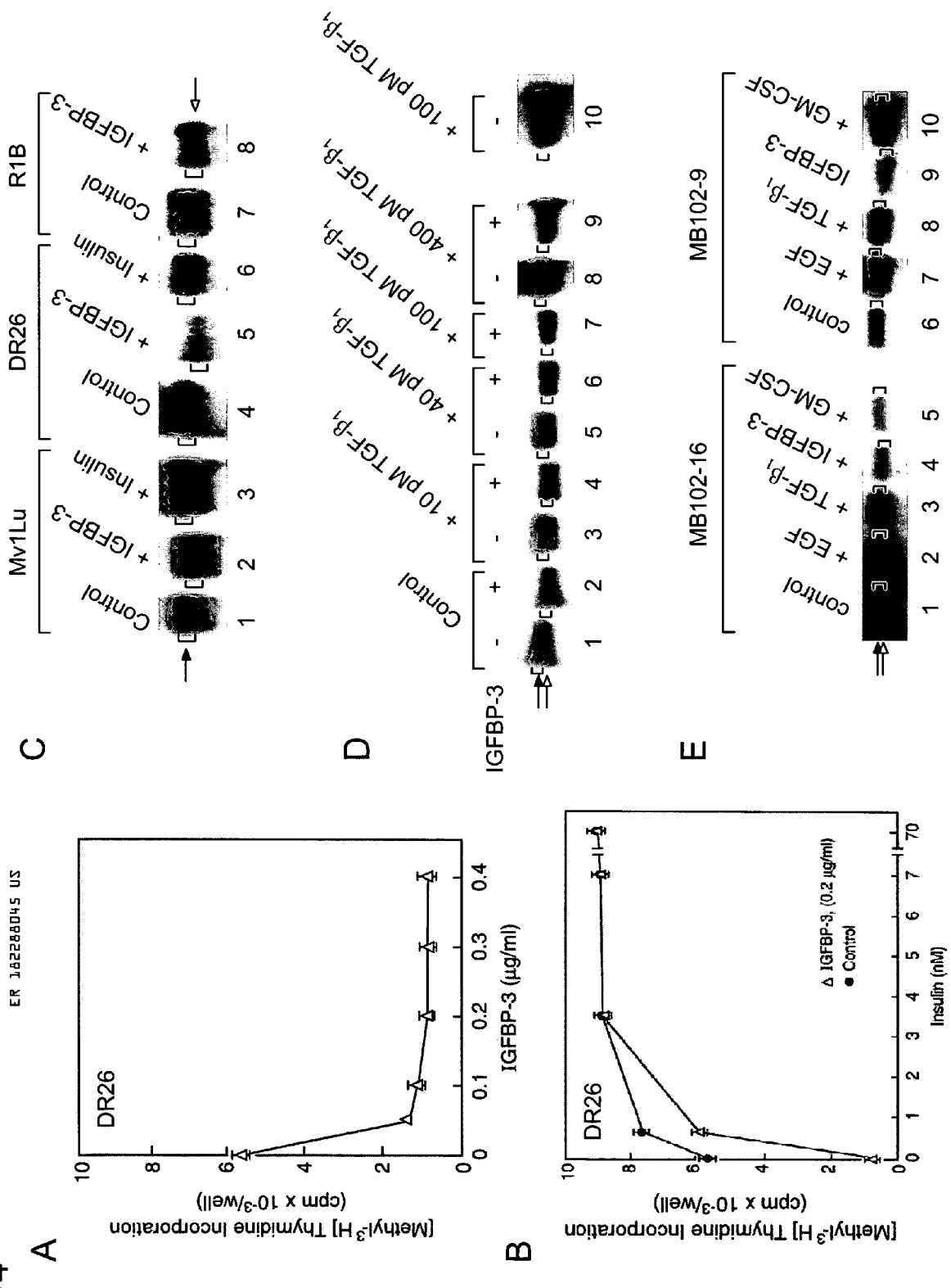

FIG. 14 depicts IGFBP-3-induced insulin-reversible growth inhibition in DR26 cells (A,B) and IGFBP-3-induced specific dephosphorylation of IRS-2 in Mv1Lu/DR26/R1B cells (C), DR26 cells (D) and MB102-16 or MB102-9 cells (E). (A,B) DR26 cells were incubated with various concentrations as indicated of IGFBP-3 in the absence (A) and presence (B) of various concentrations of insulin. After 18 hr at 37° C., the [methyl-$^3$H] thymidine incorporation into cellular DNA was determined. (C,D,E) Mv1Lu, DR26 and R1B cells metabolically labeled with $^{85}$P-orthophosphate for 2 hr were treated with IGFBP-3 (1:g/ml) or insulin (10 nM) (C). DR26 cells metabolically labeled with $^{85}$P-orthophosphate for 2 hr were treated with or without IGFBP-3 (1 μg/ml) in the presence of various concentrations of TGF-$\beta_1$ as indicated (D). Mv1Lu cells expressing αIβI and αIβII chimeric receptors (MB102-16 and MB102-9 cells, respectively) metabolically labeled with $^{85}$P-orthophosphate for 2 hr were treated with or without IGFBP-3 (1 μg/ml) or GM-CSF (1 nM) (E). After 2 hr at 37° C. (in the absence of 85P-orthophosphate in the medium), the $^{85}$P-labeled IRS-2 was immunoprecipitated and analyzed by 7.5% SDS-PAGE and autoradiography. The brace indicates the location of $^{85}$P-labeled IRS-2. The closed and open arrows indicate the locations of the slow and faster migrating forms of $^{85}$P-labeled IRS-2.

Figure 15:
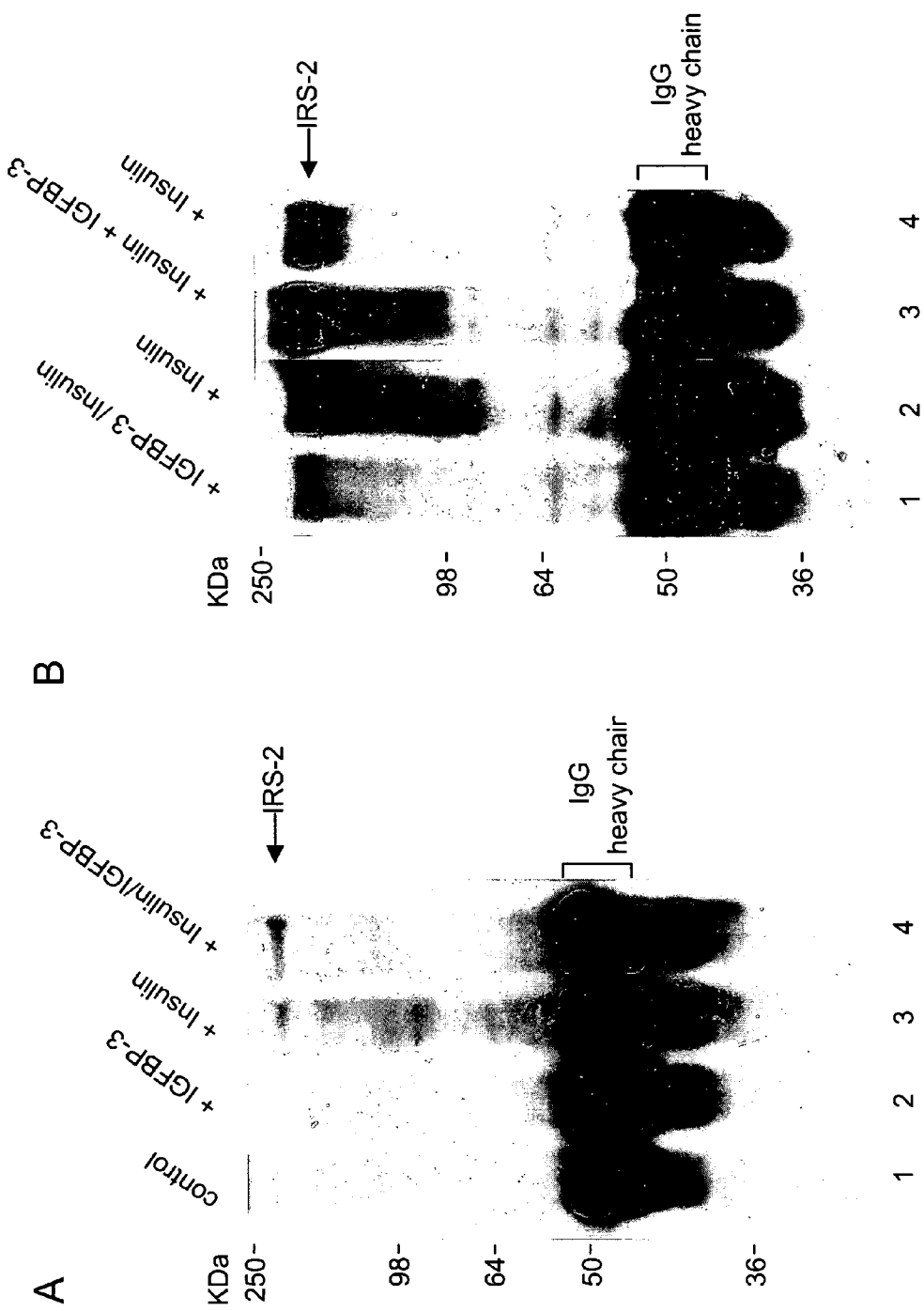

FIG. 15 depicts tyrosine phosphorylation of IRS-2 in Mv1Lu cells treated with IGFBP-3 and insulin. Cells were stimulated with or without insulin (10 nM) for 10 min and then treated with or without IGFBP-3 (1 μg/ml) for 1 hr (A). On the other hand, cells pretreated with or without IGFBP-3 (1 μg/ml) for 2 hr and then stimulated with insulin (10 nM) for 10 min (B, lane 1 and lane 2, respectively). In a parallel experiment, cells were treated with insulin (10 nM) in the presence and absence of IGFBP-3 (1 μg/ml) for 2 hr (B, lane 3 and lane 4, respectively). The cell lysates were immunoprecipitated by anti-IRS-2 IgG followed by 7.5% SDS-PAGE under reducing conditions and Western blot analysis using anti-phosphotyrosine IgG. The arrow indicates the location of tyrosine-phosphorylated IRS-2.

FIG. 16 depicts the effects of IGFBP-3 and TGF-$\beta_1$ without (A,B) and with (C,D) insulin on DNA synthesis in 85D/vector, 85D/IRS-1 and 85D/IRS2/IR cells. Cells were treated with various concentrations of IGFBP-3 (A,C) or TGF-$\beta_1$ (B,D) in the presence and absence of insulin (10 nM). After 18 hr at 37° C., DNA synthesis was determined by measuring [methyl-$^3$H] thymidine incorporation into cellular DNA. The [methyl-$^3$H] thymidine incorporation in cells treated without IGFBP-3 and TGF-$\beta_1$ was taken as 100% of DNA synthesis. Each data point is the mean±S.D. of quadruplicate determinations in four independent experiments.

Figure 17:
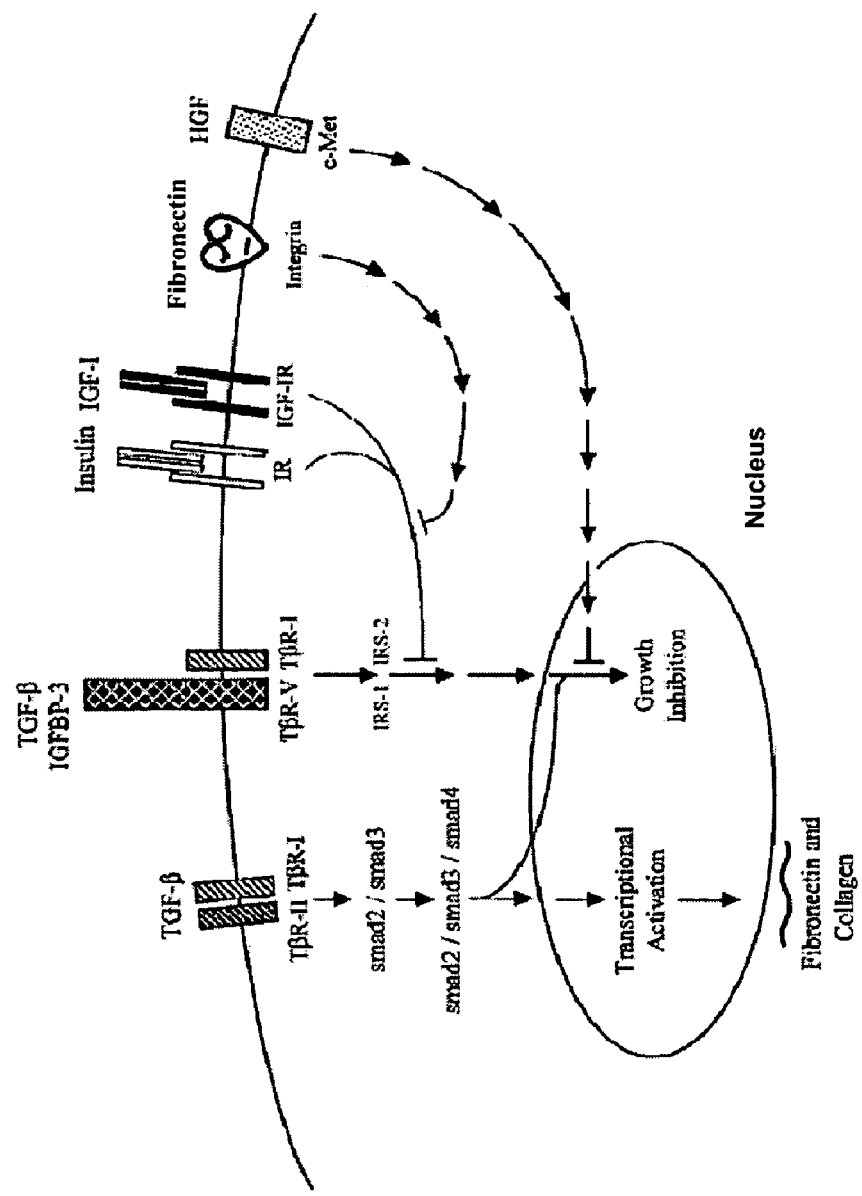

FIG. 17 depicts a proposed model for the blocking of IGFBP-3 and TGF-β growth inhibition by insulin or IGF-I and cross talk of the TβR-I/TβR-II, TβR-V (or TβR-V/TβR-I), insulin receptor, IGF-I receptor, integrin and c-Met signaling cascades.

DESCRIPTION OF THE INVENTION

It is understood that this invention is not limited to the particular methodologies, protocols, cell lines, vectors, and reagents described, as these may vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meanings as commonly understood by one of ordinary skill in the art to which this invention belongs. The preferred methods, devices, and materials are now described, although any methods and materials similar or equivalent to those described herein can be used in the practice or testing of the present invention. All publications mentioned herein are incorporated by reference herein for the purpose of describing and disclosing the cell lines, vectors, and methodologies reported in the publications, which might be used in connection with the invention. Nothing herein is to be construed as an admission that the invention is not entitled to antedate such disclosure by virtue of prior invention. Each reference cited herein is incorporated by reference herein in its entirety.

Definitions

The term "cell proliferation" means a relative increase in cell number, whether by cell division or by inhibition of cell death (e.g., necrosis, apoptosis). A cell that is actively traversing the cell cycle is said to be proliferating. The term "mitogenic" or mitogenesis is equivalent to the term "cell proliferation."

The term "TβR-V," "LRP", or "IGFBP receptor" refers to a polypeptide or protein having any one of several amino acid sequences of substantially purified low density lipoprotein (LDL) receptor related protein obtained from any species, particularly a mammalian species, including bovine, porcine, murine, and, preferably, the human species, and from any source, natural, synthetic, or recombinant. "TβR-V," "LRP", or "IGFBP receptor" as used herein also encompasses any LRP derivative or any LRP-like compound and specifically includes any fragment or subunit of LRP having at least one structural or functional characteristic of LRP. A non-limiting example of LRP has an amino acid sequence set forth in GenBank accession number NP_002323. Example LRP polypeptides and encoding polynucleotides are provided in table 1.

TABLE 1

| GenBank Accession Numbers of LRP Polypeptides and Polynucleotides | | |
|---|---|---|
| ORGANISM | POLYPEPTIDE | POLYNUCLEOTIDE |
| Homo sapiens | NP 02323 | NM 002332 |
| Mus musculus | NP 032538 | NM 008512 |
| Rattus norvegicus | XP 243524 | XM 243524 |
| Gallus gallus | CAA52870 | X74904 |
| Drosophila melanogaster | NP 788284 | NM 176104 |

"LRP activity" as used herein refers to the ability of LRP to bind TGF-β or IGFBP, to modulate (increase or decrease) the inhibition of cell proliferation, to modulate DNA synthesis or to modulate serine phosphorylation of an IRS protein.

The phrase "LRP polynucleotide" or "polynucleotide encoding a LRP" refers to the polynucleotide sequence encoding LRP or fragments or subunits thereof. A non-limiting example of a LRP polynucleotide has a nucleotide sequence set forth in GenBank accession number NM_002332. See table 1 for non-limiting examples of LRP encoding polynucleotides.

The term "mLRP" refers to LRP minireceptors, also known as SLRPs (see Bu and Rennke, *The Journal of Biological Chemistry*, 271:22218-22224 (1996), which is incorporated herein by reference, for a description of how to make and use SLRPs), which are soluble fragments of the extracellular domain (heavy chain) of LRP. "mLRP-I" has a relative molecular mass of 120 kDa and is functionally equivalent to SLRP1 of Bu and Rennke (amino acids 6-171). "mLRP-II" has a relative molecular mass of 160 kDa and is functionally equivalent to SLRP2 of Bu and Rennke (amino acids 787-1244). "mLRP-III" has a relative molecular mass of 200 kDa and is functionally equivalent to SLRP3 of Bu and Rennke (amino acids 2462-3004). "mLRP-IV" has a relative molecular mass of 160 kDa and is functionally equivalent to SLRP4 of Bu and Rennke (amino acids 3274-3843). It is herein shown that mLRPs have LRP "dominant negative" activity, which means that LRP-mediated inhibiton of cell proliferation is inhibited or reduced in the presence of a mLRP. mLRPs useful in the practice of this invention may be derived from any LRP sequence (see table 1 for examples).

The term "receptor ligand" means any substance that can bind to a receptor molecule. The receptor molecule may be substantially purified or isolated, in a cell, in a cell membrane, on the surface of a cell, in vivo, ex vivo, or in vitro. Preferred ligands are biological molecules such as TGF-β, IGFBP, IGFBP-3, insulin, IGF-1, $(Q^3A^4Y^{15}L^{16})$ IGF-1, and the like, which bind to the extracellular portion of a receptor. (Some receptors are cytoplasmic, such as steroid receptors, which do not have an extracellular portion. Nonetheless, ligands can bind cytoplasmic receptors at the ligand binding site.) Receptor ligands may be a mimic, an analogue, an agonist or an antagonist, which affects the transduction or propagation of a signal through the receptor.

The term "TGF-β" refers to any protein member of the transforming growth factor β superfamily, or fragment thereof. Preferred TGF-β include TGF-$β_1$, TGF-$β_2$ and TGF-$β_3$. The most preferred TGF-β is a TGF-$β_1$. A non-limiting example of TGF-$β_1$ has an amino acid sequence set forth in GenBank accession number NP_035707 (murine version for purpose of example). See Table 2 for examples of TGF-βs.

TABLE 2

GenBank Accession Numbers of TGF-β Polypeptides and Polynucleotides

| ORGANISM | POLYPEPTIDE | POLYNUCLEOTIDE |
|---|---|---|
| Human | AAA50405 | M19154 |
| Human | WFHU2 | |
| Rat | S10219 | |
| Mouse | WFMS2 | |
| Pig | A27512 | |

The term "IGFBP" means any insulin-like growth factor binding protein(such as IGFBP-1, -2, -3, -4, -5, and -6), which is capable of binding to LRP or effecting a cell growth inhibitory signal in a cell that expresses LRP. A non-limiting example of IGFBP-3 has an amino acid sequence set forth in GenBank accession number NP_776981 (bovine version for purpose of example). See Table 3 for examples of IGFBP.

TABLE 3

GenBank Accession Numbers of IGFBP Polypeptides and Polynucleotides

| ORGANISM | POLYPEPTIDE | POLYNUCLEOTIDE |
|---|---|---|
| Bos Taurus | NP 776981 | NM 174556 |
| Homo sapiens | NP 000589 | NM 000598 |
| Sus scrofa domestica | P16611 | J05228 |
| Mus musculus | NP 032369 | NM 008343 |
| Rattus norvegicus | NP 036720 | NM 012588 |

The term "agonist" refers to a molecule which, when bound to receptor, increases or prolongs the duration of the effect of receptor-mediated signaling. Agonists may include proteins, nucleic acids, carbohydrates, or any other substances or molecules which bind to and modulate the effects of receptor-mediated signaling. An agonist may be a receptor ligand mimic or analogue.

The term "antagonist" refers to a molecule which, when bound to a receptor, decreases the extent or duration of the effect of the activity of the receptor. Antagonists may include proteins, nudeic acids, carbohydrates, antibodies, or any other substances or molecules which decrease the effect of receptor-mediated signaling. An antagonist may be a receptor ligand mimic or analogue.

The term "substrate" or "receptor substrate" means any substance that can bind to a receptor molecule outside of a ligand binding site, usually the cytoplasmic portion of a receptor (e.g., LRP light chain cytoplasmic domain). Receptor substrate may also be a substance that does not directly bind to a receptor, but is indirectly affected by activity of the receptor. For example, IRS proteins, which directly associate with the cytoplasmic portion of the insulin receptor, and phosphatidylinositol 3' kinase, which does not directly associate with the insulin receptor, but which is nonetheless affected by insulin receptor activity, are "receptor substrates" for the insulin receptor. An example of a receptor substrate for LRP is RAP. Receptor substrates may facilitate or block the propagation of a signal through a cell.

The term "insulin receptor substrate", "IRS" or "IRS protein" refers to a polypeptide that is able to associate with a phosphotyrosine residue of the insulin receptor. IRS includes IRS-1, IRS-2 and fragments thereof. An exemplary but not limiting IRS protein has an amino acid sequence as set forth in GenBank accession number NP_061330. The polynucleotide that encodes that IRS protein has a nucleotide sequence as set forth in NM_018842.

The term "propagation" refers generally to the propagation of a signal, an effect, or a partial signal or partial effect through a cell, such as signal transduction. A block in propagation is equivalent to any inhibition or block along a signal transduction pathway. An example signal transduction pathway is the insulin-insulin receptor-IRS-phosphatidylinositol 3' phosphate pathway which utilizes substrate phosphorylation to effect a change in cell proliferation.

The term "cancer" as used herein means a disease of unregulated cell proliferation. A "cancer cell" is a cell that is abnormal in its ability to exhibit uncontrolled growth or unregulated proliferation.

The term "RAP", "RAP protein", "$α_2$MRAP", or "receptor associated protein" refers to a protein that associates with the cytoplasmic portion of LRP. By way of example, a human RAP has an amino acid sequence set forth as GenBank accession number NP_002328. A polynucleotide encoding that RAP has a sequence set forth as GenBank accession number NM_002337.

The term "integrin antagonist" refers to any agent that binds to integrin and blocks integrin from propagating a signal or binding to an extracellular protein. Preferred integrin antagonists are peptides or peptide analogues that comprise a RGD sequence.

As used herein, the term "patient" means any human or animal who suffers from a disease or disorder. The terms "disorder" and "disease" are used inclusively and refer to any condition deviating from normal.

The term "insulin-associated disorders" as used herein refers to conditions and diseases associated with energy regulation, such as but not limited to diabetes and obesity. Also are diseases associated with diabetes and obesity such as but not limited to heart disease and abnormal wound healing.

As used herein, the term "extracellular matrix" refers broadly to non-cellular matrix, typically composed of proteins, glycoproteins, complex carbohydrates, and other macromolecules. Extracellular matrix components include, for example, collagens, such as collagen types I and IV, fibronectin, laminin, and thrombospondin.

The term "fibrosis" (pl. fibroses) refers to abnormal processing of fibrous tissue, or fibroid or fibrous degeneration. Fibrosis can result from various injuries or diseases. Fibrosis typically involves the abnormal production, accumulation, or deposition of extracellular matrix components, including overproduction and increased deposition of, for example, collagen and fibronectin. "Fibrosis" is used herein in its broadest sense referring to any excess production or deposition of extracellular matrix proteins. There are numerous examples of fibrosis, including the formation of scar tissue following a heart attack, which impairs the ability of the heart to pump. Diabetes frequently causes damage/scarring in the kidneys which leads to a progressive loss of kidney function. Even after surgery, scar tissue can form between internal organs causing contracture, pain, and in some cases, infertility. Major organs such as the heart, kidney, liver, eye, and skin are prone to chronic scarring, commonly associated with other diseases. Hypertrophic scars (non-malignant tissue bulk) are common form of fibrosis caused by burns and other trauma. In addition, there are a number of other fibroproliferative disorders, including scleroderma, keloids, and atherosclerosis, which are associated respectively with general tissue scarring, tumor-like growths in the skin, or sustained scarring of blood vessels which impairs blood carrying ability.

The term "nucleic acid", "polynucleotide" or "polynucleotide sequence" as used herein refers to an oligonucleotide or nucleotide sequence and to any fragments thereof. These terms also refer to DNA or RNA of genomic or synthetic origin which may be single-stranded or double-stranded and may represent a sense or antisense strand, to peptide nucleic acid (PNA), or to any DNA-like or RNA-like material, natural, recombinant, or synthetic in origin. The skilled artisan readily understands that species specific and organellar specific codon usage, as well as the degeneracy of the genetic code, allows for a myriad different polynucleotides that encode a specific polypeptide.

As used herein, the term "peptide", "polypeptide" or "protein" means a polymer of at least four (4) amino acids linked together via peptide bonds. Said peptide, polypeptide or protein may be covalently modified, wherein the modifications may be any of the art recognized posttranslational modifications, which include for example, methylation, myristoylation, palmitylation, geranylgeranylation or any other lipidation, O-linked glycosylation, N-linked glycosylation or any other glycosylation, glycosylphosphatidylinositol ("GPI") linkage, hydroxylation, phophorylation, polyethylene glycol linkage ("pegylation"), linkage to an albumin molecule ("albumination"), acetylation and ubiquination, among other modifications.

The term "sample" is used herein in its broadest sense. Samples may be derived from any source, for example, from bodily fluids, secretions, tissues, cells, or cells in culture including, but not limited to, saliva, blood, urine, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. A sample can be in solution or can be, for example, fixed or bound to a substrate. A sample can refer to any material suitable for testing for the presence of TGF-$\beta$, IGFBP, insulin, IRS, RAP or LRP or suitable for screening for agents that bind to LRP, IRS or fragments or subunits thereof (e.g., minireceptors). Methods for obtaining such samples are within the level of skill in the art.

The Invention

Several lines of evidence, which are herein disclosed, demonstrate that T$\beta$R-V is identical with LRP. Such evidence includes: 1) The molecular masses of 23 tryptic peptides of T$\beta$R-V are identical with those of the corresponding tryptic peptides of human LRP. 2) The LRP antagonist RAP inhibits binding of $^{125}$I-IGFBP-3 and $^{125}$I-TGF-$\beta_1$ to T$\beta$R-V purified from bovine liver plasma membranes and in Mv1Lu cells as determined by affinity labeling. 3) $^{125}$I-IGFBP-3-affinity labeled T$\beta$R-V in Mv1Lu cells is immunoprecipitated by antisera to LRP and T$\beta$R-V. 4) RAP blocks IGFBP-3-induced inhibition of DNA synthesis in Mv1Lu cells. 5) Mutagenized Mv1Lu cells selected for reduced expression of LRP show attenuated expression of T$\beta$R-V as determined by $^{125}$I-TGF-$\beta_1$-affinity labeling. 6) Cells lacking T$\beta$R-V or expressing low levels of T$\beta$R-V also lack or express little LRP, as demonstrated by Western blot analysis and by $^{125}$I-IGFBP-3 affinity labeling. 7) Stable transfection of H1299 cells with LRP cDNA confers sensitivity to growth inhibition by TGF-$\beta_1$ and IGFBP-3. 8) Cells that express mLRP minireceptors (i.e., heavy chain domains mLRP-I, mLRP-II, mLRP-III, or mLRP-IV), which have LRP dominant negative activity, show reduced sensitivity to TGF-$\beta$ or IGFBP-mediated inhibition of cell proliferation.

Knowing the full and true molecular structure of T$\beta$R-V enables the development of methods and kits for identifying agents that impinge upon the TGF-$\beta$/IGFBP-3/T$\beta$R-V-mediated inhibition of cell proliferation pathway. LRP may now be employed in vitro or cell based assays to identify those agents that antagonize or agonize said pathway. Furthermore, given that many cancer cell types do not express T$\beta$R-V and are unresponsive to the growth inhibitory effects of TGF-$\beta$ or IGFBP, the instant discovery that LRP is an important receptor that mediates the cell proliferation inhibitory effects of TGF-$\beta$ or IGFBP has enabled the development of compositions and methods useful in conferring TGF-$\beta$ or IGFBP sensitivity to those cancer cell types.

It was also discovered that insulin, IGF-1 and ($Q^3A^4Y^{15}L^{16}$) IGF-I are capable of blocking IGFBP-induced growth inhibition and partially reverse TGF-$\beta$-induced growth inhibition in the presence of an integrin antagonist (e.g., cyclic RGD peptide) in Mv1Lu cells. These results imply that the insulin/IGF-I receptor signaling pathways cross-talk with the LRP/T$\beta$R-V/IGFBP receptor signaling, T$\beta$R-I/T$\beta$R-II signaling pathways and possibly others such as the integrin signaling pathway (90). Several lines of evidence presented herein indicate that IRS proteins are important for TGF-$\beta_1$ and IGFBP-3 growth inhibition. These include: 1) Insulin and ($Q^3A^4Y^{15}L^{16}$) IGF-I, but not EGF, aFGF and bFGF, block IGFBP-induced growth inhibition and partially reverse TGF-$\beta$-mediated growth inhibition in the presence of a cyclic RGD peptide in Mv1Lu cells. 2) IGFBP induced a specific dephosphorylation of IRS-2 in Mv1Lu cells. Such dephosphorylation appears to correlate with the IGFBP-induced growth inhibition in Mv1Lu cells and their mutant cells. 3) Insulin and IGF-I, but not other growth factors, block the IGFBP-3-induced specific dephosphorylation of IRSs in Mv1Lu cells. 4) TGF-$\beta$ and IGFBP induce DNA synthesis inhibition of 32D cells expressing either IRS-1 or IRS-2 but not 32D cells stably expressing vector control. 5) Insulin blocks IGFBP-induced DNA synthesis inhibition in 32D cells expressing IRS-2 and the insulin receptor and partially reverses TGF-β inhibition of DNA synthesis in these cells.

It was also discovered that the internalization and endosomal trafficking of TGF-β or IGFBP through LRP is in part pH dependent and relies in part on the annexin VI molecule (infra). Agents that inhibit the internalization of LRP ligands are envisioned to increase the signaling of those ligands. That is, TGF-β and IGFBP signaling are expected to be enhanced upon treatment of a cell with an agent that inhibits the internalization of the ligands. It is disclosed herein that phenothiozine-related compounds (e.g., trifluoperazine, fluphenazine, promethazine, and derivatives thereof), transglutaminase inhibitors (e.g., monodansylcardaverine), calmodulin antagonists (e.g., W-7) and substances that interfere with annexin VI expression (e.g., anti-annexin VI antibodies or Fabs) are effective in blocking or reducing the internalization of a LRP ligand.

In view of these discoveries, the invention is drawn to compositions and methods useful to inhibit cell proliferation. Preferably, the cells are cells which are insensitive to the inhibitory effects of TGF-β or IGFBP on cell proliferation. Certain types of cancer cells, especially those cancer cells with reduced expression of active LRP, are insensitive to TGF-β or IGFBP. Therefore, the invention is also drawn to compositions and methods for treating a cancer cell, wherein the cancer cell may be in a patient. One embodiment of the invention is drawn to the observations that TGF-β or IGFBP insensitive cells lack a functional LRP, which mediates the cell proliferation signals of TGF-β and IGFBP, and by supplying a functional copy of the LRP, preferably as a polynucleotide that encodes a functional LRP, to those cells, those cells become competent to respond to TGF-β or IGFBP. Thus, those compositions, which are useful also in the practice of the instant methods, include (a) a TGF-β (preferably a polypeptide) or an IGFBP (preferably a polypeptide), and a LRP (preferably via a polynucleotide encoding a LRP), or (b) a TGF-β (preferably a polypeptide) or an IGFBP (preferably a polypeptide), and a IRS protein (preferably via a polynucleotide encoding a IRS-1 or -2).

Furthermore, in view of the observation that agents, which affect endosomal trafficking, are able to inhibit TGF-β or IGFBP internalization, the invention is also drawn to compositions comprising those agents and methods comprising the use of those agents to affect cell proliferation. Preferred agents include phenothiozine-related compounds (e.g., trifluoperazine, fluphenazine, promethazine, and derivatives thereof), transglutaminase inhibitors (e.g., monodansylcardaverine), calmodulin antagonists (e.g., W-7) and substances that interfere with annexin VI expression (e.g., anti-annexin VI antibodies or Fabs). It is envisioned that these agents, preferably used in conjunction with a LRP ligand, such as TGF-β or IGFBP, inhibit the endocytosis of the ligand, thereby allowing the ligands to contact the cell longer and having a greater effect on the cell.

In the converse, TGF-β (and likewise IGFBP signaling) promote cell proliferation in some cells types—e.g., gliomas, mesodermal-derived cancers, and cells that contribute to the formation of fibroses. Therefore, the invention is drawn to compositions useful for and methods of inhibiting TGF-β or IGFBP activity. As mentioned above, the inventor has discovered that (a) dominant negative LRPs, e.g., mLRPI-IV, are capable of interfering with TGF-β or IGFBP signaling through LRP, (b) RAP attenuates LRP signaling and likewise TGF-β or IGFBP signaling, and (c) a combination of an insulin receptor agonist (e.g., insulin, IGF-1, analogues thereof) and integrin antagonist (e.g., cyclic RGD [Arg-Gly-Asp] and other RGD containing molecules) can override the cell proliferation inhibition properties of TGF-β or IGFBP, purportedly by affecting the phosphorylation status of IRS protein.

Thus, in one embodiment of the invention, the composition comprises a dominant negative mLRP minichromosome or a polynucleotide encoding same, and the method comprises contacting a cell or its immediate environment with a mLRP minichromosome or a polynucleotide encoding a mLRP minichromosome. In another embodiment of the invention, the composition comprises a RAP protein or a polynucleotide encoding same, and the method comprises contacting a cell or its immediate environment with a RAP protein or a polynucleotide encoding a RAP protein. In another embodiment of the invention, the composition comprises an insulin receptor ligand, e.g., insulin, IGF-1, $(Q^3A^4Y^{15}L^{16})$ IGF-1, and the like) and an integrin antagonist, e.g., cyclic RGD and cycloGRGDSPA. The correlated method comprises contacting a cell with the composition comprising an insulin receptor ligand, e.g., insulin, IGF-1, $(Q^3A^4Y^{15}L^{16})$ IGF-1, and the like) and an integrin antagonist, e.g., cyclic RGD and cycloGRGDSPA. In yet another embodiment, the present invention is drawn to methods of inhibiting TGF-β or IGFBP cell proliferation signaling through LRP by administering to a cell an antisense or RNAi molecule, which is specific to LRP, to attenuate LRP activity in the cell. This provides for a therapeutic approach, which effects LRP expression and activity by interfering with the expression of the LRP.

Therapeutics

The expression of TGF-β (or TGF-β-mediated signaling) is associated with the onset and extent of various fibrotic and proliferative disorders. In addition, inhibition of TGF-β activity has been shown to accelerate wound healing, and reduce scarring (Huang et al., *FASEB* 16:1269-1270 (2002) and copending U.S. patent application Ser. No. 09/095,637, both of which are incorporated herein by reference). Therefore, LRP, IRS and insulin-receptor, in addition to TGF-β or IGFBP, may be important therapeutic targets in TGF-β associated disorders, such as fibroses and cancer.

In one aspect, the present invention provides methods for treating TGF-β-associated disorders arising from the overproduction or over-expression of connective tissue and extracellular matrix. Such diseases, disorders, or conditions include excessive scarring resulting from acute or repetitive traumas; systemic or acute fibrosis of organs such as the kidney, lungs, liver, eyes, heart, and skin, including scleroderma, keloids, and hypertrophic scarring, general tissue scarring, and tumor-like growths in the skin; sustained scarring of blood vessels, leading to impaired blood-carrying ability, hypertension, hypertrophy, etc.; diseases caused by vascular endothelial cell proliferation or migration, such as cancer, including dermatofibromas, conditions related to abnormal endothelial cell expression, breast carcinoma desmoplasis, angiolipoma, and angioleiomyoma; atherosclerosis and systemic sclerosis, including atherosclerotic plaques, inflammatory bowel disease, and Crohn's disease; angiogenesis, including angiogenesis-related disorders involving, growth of blood vessels associated with tumor formation, as well as other proliferative processes which play central roles in atherosclerosis, arthritis, cancer, and other disease states; neovascularization involved in glaucoma; inflammation due to disease or injury, including joint inflammation; tumor growth metastasis; interstitial disease; dermatological diseases; arthritis, including chronic rheumatoid arthritis; arteriosclerosis; diabetes, including diabetic nephropathy, retinopathy, hypertension, and other kidney disorders; and fibrosis resulting from chemotherapy, radiation treatment, dialysis, and allograft and transplant rejection.

Compositions and Therapeutic Methods

Thus, the present invention also provides compositions and methods of treatment to inhibit tumor cell growth or the formation of scar tissue in patients in need thereof. The method comprises administering to the patient a composition of the invention herein described (supra).

It is believed that the patients in these methods can be any vertebrate animal. Since the known molecular structures of LRP, TGF-$\beta$, IGFBP, RAP, IRS, annexin VI, integrin, insulin and IGF-1 are very well conserved across vertebrates, the skilled artisan would reasonably expect those proteins or polypeptides to have very similar biochemical properties among vertebrates and that vertebrate homologues or conserved variants of LRP, TGF-$\beta$, IGFBP, RAP, IRS, annexin VI, integrin, insulin and IGF-1 may be used interchangeably. Preferred patients in these methods are mammals; most preferred patients are humans having cancer, at risk for cancer, having diabetes or suffering from one or myriad fibroses. Nonetheless, the utility of the methods with any vertebrate or with any combination of homologues can be determined without undue experimentation by administering the composition to a cultured cancer cell, epithelial cell, fibroblast or other relevant cell-type specific to the vertebrate in question and performing a simple DNA synthesis assay or cell proliferation assay as herein described in the examples.

These therapeutically useful compositions may be administered to a patient by any suitable route known in the art including, for example, intravenous, subcutaneous, intramuscular, transdermal, intrathecal, or intracerebral. Administration can be either rapid as by injection or over a period of time as by slow infusion or administration of a slow release formulation.

It is contemplated that the instant compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is also contemplated that certain formulations comprising the instant compositions are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic and nucleic acid degradation and/or substances that promote absorption such as, for example, surface active agents.

The instant composition is administered to vertebrates in an amount effective to decrease the growth rate of cancer cells or scar forming tissue within the patient. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in thrombosis assays. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

The instant compositions may be administered topically to a surface of the body, such as blood vessel intima (via a catheter), skin (direct application as a crème, gel, salve or ointment), and visceral membranes (parenteral injection or upon exposure of the visceral membranes).

Expression of Polynucleotides and Polypeptides

Nucleic acid sequences encoding any and all of the instant polypeptides useful in the practice of this invention (e.g., LRP, mLRP minichromosome, TGF-$\beta$, IGFBP, RAP, IRS, annexin VI, integrin, insulin and IGF-1) can be expressed in vitro by nucleic acid transfer into a suitable host cell.

In order to express a LRP, TGF-$\beta$, IGFBP, RAP, IRS, annexin VI, integrin, insulin and IGF-1, fragment, variant or subunit thereof, the polynucleotide sequence encoding the polypeptide, variant or subunit, may be inserted into an appropriate expression vector, i.e., a vector which contains the necessary elements for the transcription and translation of the inserted coding sequence.

Methods well-known to those skilled in the art can be used to construct expression vectors containing the instant polynucleotides and polynucleotides that encode the instant polypeptides and appropriate transcriptional and translational control signals. These methods can include in vitro and in vivo recombinant technologies and synthetic techniques. (See, e.g., Maniatis et al. (1989) Molecular Cloning: A Laboratory Manual, Chapters 4, 8, 16, and 17, Cold Spring Harbor Press, Plainview, N.Y.; and Ausubel, F. M. et al. (1995) Current Protocols in Molecular Biology, Chapters 9, 13, and 16, John Wiley and Sons, New York, N.Y.)

A variety of expression vector/host systems well-known in the art may be utilized to express sequences encoding the instant polypeptides. These systems include, but are not limited to, microorganisms such as bacteria transformed with recombinant bacteriophage, plasmid, or cosmid DNA expression vectors; yeast transformed with recombinant yeast expression vectors; insect cell systems transformed with recombinant virus expression vectors (e.g., baculovirus); plant cell systems transformed with recombinant virus expression vectors (e.g., cauliflower mosaic virus (CaMV), tobacco mosaic virus (TMV), etc.) or bacterial expression vectors (e.g., Ti or BR322 plasmids); filamentous fungi transformed with fungal vectors; animal cell systems, preferably mammalian systems, including those transformed with recombinant virus expression vectors (e.g., adenovirus, vaccinia virus) human tumor and other cells (including HT-1080 and CHO cells). Methods for expressing recombinant polypeptides or proteins are well known in the art and can be found in (2003) Current Protocols in Protein Science, John Wiley and Sons, New York, N.Y., which is herein incorporated in its entirety by reference.

Diagnostics

Another aspect of the present invention provides methods for diagnosing TGF-$\beta$ or IGFBP-associated disorders, including fibrotic and sclerotic disorders, angiogenesis, and cancer, and other proliferative disorders. In one embodiment of the present invention, a biopsied cell can be screened for the presence of LRP, by any one of several methods that are well known in the art, including for example, immunodetection of LRP (RIA, ELISA, Western, immunoprecipitation, immunofluorescence microscopy), IGFBP -or- TGF-$\beta$ binding to the cell via LRP, a change in IRS protein phosphorylation status, a change in DNA synthesis activity, and a change in cell proliferation activity.

Preferably, in the diagnostic methods of the present invention, normal or standard values for LRP activity or expression, or for normal levels of ligand/LRP binding are established in order to provide a basis for the diagnosis of the existence of a TGF-$\beta$ -or- IGFBP-associated disorder. In one of the methods of the present invention, this is accomplished by combining cell or other samples taken from normal subjects with antibody to LRP under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified LRP or fragments or subunits thereof. Standard values obtained from normal samples may be compared, for example, in a specific embodiment, with values obtained from samples from subjects suspected of having a TGF-$\beta$- or IGFBP-associated disorder, or having a predisposition to a TGF-$\beta$- or IGFBP-associated disorder. Deviation between standard and subject values establishes the presence of or predisposition to the disease state. Antibody detection (immuno-) assays are well praticed and well-known in the art. These assays are described in detail in Using Antibodies: A Laboratory Manual, ed. Harlow and Lane, Cold Spring Harbor Laboratory Press (1999), which is herein incorporated by reference.

Polynucleotide sequences encoding LRP or fragments or subunits thereof can be used for the diagnosis of conditions or diseases associated with altered or abnormal levels of LRP expression and activity. For example, polynucleotide sequences encoding LRP may be used in hybridization or PCR assays of fluids or tissues from biopsies to detect LRP expression and activity. The form of such qualitative or quantitative methods may include Southern or northern analysis, dot blot or other membrane-based technologies; PCR technologies, such as quantitative RT-PCR; dip stick, pin, chip, microarray and ELISA technologies. All of these techniques are well known in the art and readily available commercially.

Diagnostic Kits

The present invention provides kits for detecting LRP in samples, in particular, in cells or tissues. In a particular embodiment, this kit comprises at least one substance that binds to LRP, such as TGF-$\beta$, IGFBP, or monoclonal antibody specific for LRP or fragments or subunits thereof. The kit further comprises reagents for detecting the substance that binds to the LRP. The detection may be of phosphotyrosine, as TGF-$\beta$ and IGFBP are shown to block activation of IRS proteins via tyrosine phosphorylation changes. The detection may be counts of radiolabeled TGF-$\beta$, IGFBP or antibody bound to the sample (or membrane fragment, which comprises LRP). In another embodiment, the detection may be any immunoassay. In another embodiment, the diagnostic kit of the present invention comprises elements useful in the detection of LRP in tissue samples, using immunohistochemical techniques.

In yet another embodiment provides a diagnostic kit for detecting and measuring levels of LRP mRNA in tissue samples. In one embodiment, the kit comprises reagents used to reverse transcribe LRP mRNA to DNA. The kit can further comprise reagents necessary to amplify LRP-specific DNA, including primers complementary to polynucleotides encoding LRP or fragments or subunits thereof.

In a preferred embodiment, the diagnostic kit of the present invention is packaged and labeled, for example, in a box or container which includes the necessary elements of the kit, and includes directions and instructions on the use of the diagnostic kit.

Methods for Screening

The present invention additionally contemplates methods for screening for compounds or agents that modulate the TGF-$\beta$ or IGFBP signaling through LRP. The methods of the claimed invention also include the use of LRP or fragments or subunits thereof to screen for or otherwise identify useful ligands, including agonists or antagonists, which can specifically bind to LRP or fragments or subunits thereof, or otherwise affect LRP signaling as it relates to cell proliferation or IRS phosphorylation status. Compounds that bind to or are bound by LRP may activate (agonist), inhibit (antagonist), or otherwise enhance or inhibit such LRP activities. The compounds can include, for example, antibodies and fragments thereof, small molecules, polypeptides (synthetic, natural, or enzymatically- or recombinantly-produced), minichromosomes (e.g., soluble, ligand-binding LRP heavy chain fragments) and aptamers.

The screening methods of the present invention can directly test for the binding of a compound to LRP. Alternatively, screening assays can test for binding of a candidate compound in the presence of a labeled competitor, such as $^{125}$I-TGF-$\beta$ or $^{125}$I-IGFBP. Binding can be detected by a number of methods available in the art, including, for example, fluorophores, enzyme conjugates, radioisotopes, or any detectable label.

In one embodiment, screening assays of the present invention include contacting the LRP or fragments or subunits thereof with a candidate agent, detecting a level of LRP-signaling activity or LRP-binding, for example, by detecting the presence of TGF-$\beta$ or IGFBP/LRP complexes and comparing that level of activity or binding to a standard level obtained by methods known in the art. These methods could involve LRP or agents to be screened affixed to solid supports, cell-free preparations, or natural or synthetic product mixtures. Assays such as ELISA, can be designed in which antibodies, monoclonal or polyclonal, bind directly or indirectly to LRP or compete with LRP for binding to TGF-$\beta$ or IGFBP.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Cellular Growth Inhibition by IGFBP-3 and TGF-β1 Requires LRP.

Summary

The type V TGF-β receptor (TβR-V), which proved to be identical to the IGFBP-3 receptor, mediates the IGF-independent growth inhibition induced by IGFBP-3. Many human carcinoma cells lack or express very low levels of TβR-V. Growth of these cells is not inhibited by TGF-$β_1$ or IGFBP-3, suggesting that TβR-V may play a role in the malignant phenotype of these cells. It is herein demonstrated that TβR-V is actually identical to the low-density lipoprotein receptor-related protein (LRP) as shown by MALDI-TOF analysis of tryptic peptides of TβR-V purified from bovine liver. In addition, $^{125}$I-IGFBP-3-affinity labeled TβR-V in mink lung epithelial cells (Mv1Lu cells) is immunoprecipitated by antibodies to LRP and TβR-V. The receptor-associated protein (RAP), an LRP antagonist, inhibits binding of $^{125}$I-TGF-$β_1$ and $^{125}$I-IGFBP-3 to TβR-V and diminishes IGFBP-3-induced growth inhibition in Mv1Lu cells. Mutagenized Mv1Lu cells selected for reduced expression of LRP have an attenuated growth inhibitory response to TGF-$β_1$ and IGFBP-3. LRP-null mouse embryonic fibroblasts lack a growth inhibitory response to TGF-$β_1$ and IGFBP-3. On the other hand, stable transfection of a human lung carcinoma cell line (H1299) with LRP cDNA restores the growth inhibitory response to TGF-$β_1$ and IGFBP-3. These results suggest to the skilled artisan that LRP/TβR-V is required for the growth inhibitory response to IGFBP-3- and TGF-$β_1$.

Experimental Procedure-Materials

Na$^{125}$I (17 C/mg), Trans $^{35}$S-label (71,00 Ci/mole), [methyl-$^3$H] thymidine (67 Ci/mmole) were purchased from ICN Biochemicals (Irvine, Calif.). Molecular mass protein standards (myosin, 205 kDa, β-galactosidase, 116 kDa; phosphorylase b, 97 kDa; bovine serum albumin, 68 kDa; ovalbumin 43 kDa; carbonic anhydrase, 29 kDa; β-lactoglobulin, 18 kDa), chloramine T and Triton X-100 were obtained from Sigma (St. Louis, Mo.). Precision protein standards and protein molecular weight markers were obtained from Bio-Rad (Hercules, Calif.) and Life Tech, respectively. $^{125}$I-TGF-$β_1$ and $^{125}$I-IGFBP-3 (1-4×10$^5$ cpm/ng) were prepared as described previously (13,14). Anti-TβR-V serum and anti-human LRP light chain serum (C-terminal 15-residue peptide) were raised in rabbits according to published procedures (14,26). Anti-human LRP IgG and anti-human LRP serum and human receptor-associated protein (RAP) were kindly provided by Drs. Guejun Bu, Joachim Herz and Dudley Strickland. GST-RAP (a fusion protein of glutathione S-transferase and RAP) was expressed in E. Coli using pGEX-KG-RAP (6.4 kb) plasmid and purified according to the procedure of Herz et al. (33). pGEX-KG-RAP, pcDNA 3.1(−)neo and pcDNA 3.1(−)neoLRP plasmids were kindly provided by Dr. Joachim Herz. Wheat germ lectin-Sepharose 4B was prepared as described previously (27). Protein A-sepharose was obtained from Pharmacia LKB Biotech (Piscataway, N.J.). $β_1^{25}$(41-65), a specific TGF-β peptide antagonist, was prepared as described previously (28). Disuccinimidyl suberate (DSS) was obtained from Pierce. Human TGF-$β_1$ was purchased from Austral Biologicals (Santa Clara, Calif.) and R & D Systems (Minneapolis, Minn.). Human IGFBP-3 (expressed in E. Coli, M.W. ~35,000) was obtained from Upstate (Charlottesville, Va.). Mink lung epithelial cells (Mv1Lu cells), mouse embryonic fibroblasts (MEF), LRP-null mouse embryonic fibroblasts (PEA-13 cells), human colorectal carcinoma cells (HCT116 and RII37 cells), human lung carcinoma cells (H1299 cells), human hepatocarcinoma cells (HepG2 and H3B cells) and human osteosarcoma cells were maintained in Dulbecco's modified Eagle's medium (DMEM) containing 10% fetal calf serum. MEF and PEA-13 cells were obtained from American Type Culture Collection (Rockville, Md.). Human bone marrow-derived mesenchymal stem cells (HBMC) were kindly provided by Dr. Su-Li Cheng.

Experimental Procedures-Purification of TβR-V

The TβR-V was purified by DEAE-cellulose column chromatography after Triton X-100 extraction of bovine liver plasma membranes and wheat germ lectin-Sepharose 4B affinity column chromatography as described previously (27). $^{125}$I-TGF-$β_1$ affinity labeling was used to locate TβR-V in the chromatographic functions. The TβR-V was clearly identified as a ~400-kDa Coomassie blue-stained protein band on SDS-PAGE in the N-acetylglucosamine eluents of wheat germ lectin-Sepharose 4B affinity column chromatography and in the NaCl eluents of DEAE-cellulose column chromatography.

Experimental Procedures-MALDI-TOF Analysis

The TβR-V purified from the DEAE-cellulose chromatography or wheat germ lectin-Sepharose 4B was subjected to 5% SDS-PAGE under reducing conditions, stained with Coomassie blue and digested with trypsin. MALDI-TOF analysis of the trytpic digests was carried out at Applied Biosystems, CA and the Biotechnology Resource Laboratory, HHMI Biopolymer Laboratory/M. Keck Foundation, Yale Cancer Center Mass Spectrometry Resource, New Haven, Conn. The results provided by the two institutions appeared to be the same.

Experimental Procedures-Western Blot Analysis

Equal amounts of protein from each cell type were subjected to 5% or 7.5% SDS-PAGE under non-reducing conditions (for using antisera or antibodies to LRP heavy chain) or reducing conditions followed by electrophoretic transblotting onto nitrocellulose membranes. The antigens on the nitrocellulose membranes were reacted with antisera or antibodies to LRP heavy chain and light chain followed by incubation with the second antibody-conjugated with horse radish peroxidase and visualized using the ECL system (Santa Cruz).

Experimental Procedures-Northern Blot Analysis

The RNA analysis of plasminogen activator inhibitor-1 (PAI-1), glyceraldehyde-3-phosphate dehydrogenase (G3PDH) and LRP was carried out as described previously (28). The relative levels were estimated based on the ratio of PAI-1 mRNA and G3PDH mRNA levels or of LRP mRNA and ribosomal RNA levels. The relative intensities of the mRNAs on the autoradiograms were quantified by a PhosphoImager.

Experimental Procedures—[methyl-$^3$H] Thymidine Incorporation Assay

Cells were plated on 24-well clustered dishes and incubated with various concentrations of TGF-$\beta_1$ or IGFBP-3. After incubation at 37° C. for 16 hr, the cells were pulse-labeled with 1 µCi of [methyl-$^3$H]thymidine at 37° C. for 4 hr (14). The cells were then washed with 1 ml of 10% trichloroacetic acid twice and 0.5 ml of ethanol:ether (2:1, v/v) once and dissolved in 0.2 N NaOH for scintillation counting. To examine the effect of GST-RAP on IGFBP-3-induced inhibition of DNA synthesis, cells were incubated with various concentrations of IGFBP-3 and GST-RAP (100 µg/ml). During incubation, GST-RAP (100 µg/ml) or the solvent vehicle was added to the medium hourly for 8 hr. The assays were performed in quadruplicate.

Experimental Procedures-Mutagenesis of Mv1Lu Cells

The mutagenesis and Pseudomonas exotoxin selection of Mv1Lu cells were performed according to Fitzgerald et al. (29). Briefly, Mv1Lu cells were grown in DMEM containing 10% fetal calf serum and treated with 5 mM ethylmethane sulfonate in the DMEM medium. After 21 hr, the cells were split at a ratio of 1:50 in 10-cm Petri dishes and grown for 4 days. Cells were then treated with Pseudomonas toxin (100 ng/ml) for one week. The clones were selected and grouped into two classes—one expressed very low levels of LRP (a representative clone was PEA-C11) and the other expressed LRP levels comparable to those of parent cells (a representative clone was PEA-B1 cells). These were found to have alterations in post-LRP events.

Experimental Procedures-Stable Transfection of H1299 Cells with LRP cDNA

Cells were plated at a cell density of $7\times10^5$/10-cm plate. Twelve hr later, the cells were transfected with pcDNA3.1(–)neoLRP, pcDNA3.1(–)neo vector using the calcium phosphate method. Briefly, 20 µg of pcDNA 3.1(–)neoLRP or of pCDNA 3.1(–)neo vector was mixed with 417.5 µl $H_2O$. $CaCl_2$ (2 M in $H_2O$, 62.5 µl) was then slowly added to the DNA solution. This $CaCl_2$ and DNA solution was then slowly added to 0.5 ml of 2×HEPES buffer (50 mM HEPES, pH 7.05, 280 mM NaCl, 10 mM KCl, 1.5 mM $Na_2HPO_4$ and 1.2 mM glucose). After 15-30 min at room temperature, the solution was added to the medium of each 10-cm Petri dish. After 12 hr at 37° C. The cells were washed with phosphate-buffered saline and incubated with fresh medium. Twenty-four hr later, the cells were split at a ratio of 1:10 and plated on 6-well clustered plates containing 2 ml medium. After incubation at 37° C. for 24 hr, the cells were selected with 800 µg/ml of G418. After approximately 14 days, the cells expressing LRP and vector only were selected and named H1299/LRP and H1299/vector cells, respectively. The expression of the transfected LRP cDNA was determined by Western blot analysis.

Experimental Procedures-$^{125}$I-Labeling of Cell Surface LRP

Cell surface LRP was labeled with $^{125}$I using the lactoperoxidase method as described previously (26). The cell surface $^{125}$I-labeled LRP in the cell lysates was immunoprecipitated with antisera to LRP heavy chain or light chain (2-5 µg) and analyzed by 5 or 7.5% SDS-PAGE under reducing conditions. Both the LRP heavy chain or intact LRP and LRP light chain were labeled with $^{125}$I.

Experimental Procedures-$^{125}$I-TGF-$\beta_1$- and $^{125}$I-IGFBP-3-Affinity Labeling Purified T$\beta$R-V and cells were affinity-labeled with $^{125}$I-TGF-$\beta_1$ or $^{125}$I-IGFBP-3 according to the published procedures (14,15,24). The $^{125}$I-IGFBP-3-affinity labeled T$\beta$R-V was immunoprecipitated with anti-LRP serum, anti-LRP IgG, anti-T$\beta$R-V serum or non-immune serum (2-10 µg) as described previously (24).

Experimental Procedures-Cell Growth

Cells were plated at a density of $1$-$2\times10^4$ cells/dish in DMEM containing 1% fetal calf serum. The cell number was counted every day or after a 3-day incubation using a hematocytometer. The assays were performed in quadruplicate.

Results

The T$\beta$R-V is a high molecular weight non-proteoglycan membrane glycoprotein. It was previously reported to be a serine-specific kinase (30), but it was recently found that the kinase activity is not intrinsic to the T$\beta$R-V but is due to a casein kinase II-like kinase associated with it. To determine its structure, T$\beta$R-V was first purified from bovine liver plasma membranes as described previously (27). The purified T$\beta$R-V migrated as a single band on 5% SDS-polyacrylamide gel electrophoresis (SDS-PAGE). The Coomassie Blue-stained band was excised and subjected to MALDI-TOF analysis after trypsin digestion. As shown in Table 4, the MALDI-TOF analysis revealed that the molecular masses of 23 tryptic peptides of bovine T$\beta$R-V were identical with those of the corresponding tryptic peptides of human LRP (25). This result suggests that bovine T$\beta$R-V is the homolog of human LRP.

TABLE 4

Mass spectroscopic sequence analysis of trypsin-generated peptide fragments of the T$\beta$R-V purified from bovine liver plasma membranes

| Peptide Number | Measured Mol. Mass | Peptide amino acid sequence of human LRP (calculated molecular mass) | Amino acid position within human LRP | SEQ ID NO. |
|---|---|---|---|---|
| 1 | 886.5 | ILWIDAR (886.5) | 1448-1454 | SEQ ID NO: 1 |
| 2 | 924.4 | VYWSDVR (924.4) | 1629-1635 | SEQ ID NO: 2 |

TABLE 4-continued

Mass spectroscopic sequence analysis of trypsin-generated peptide fragments of the TβR-V purified from bovine liver plasma membranes

| Peptide Number | Measured Mol. Mass | Peptide amino acid sequence of human LRP (calculated molecular mass) | Amino acid position within human LRP | SEQ ID NO. |
|---|---|---|---|---|
| 3 | 1181.6 | NVIALAFDYR (1181.6) | 2235-2244 | SEQ ID NO: 3 |
| 4 | 1243.6 | SERPPIFEIR (1243.6) | 784-793 | SEQ ID NO: 4 |
| 5 | 1308.6 | SLPPAAPPTTSNR (1308.6) | 3928-3940 | SEQ ID NO: 5 |
| 6 | 1313.7 | TVLVSSGLREPR (1313.7) | 3137-3148 | SEQ ID NO: 6 |
| 7 | 1322.7 | TTLLAGDIEHPR (1322.7) | 1379-1390 | SEQ ID NO: 7 |
| 8 | 1363.6 | EYAGYLLYSER (1363.6) | 2196-2206 | SEQ ID NO: 8 |
| 9 | 1374.7 | YVVISQGLDKPR (1374.7) | 2000-2011 | SEQ ID NO: 9 |
| 10 | 1457.6 | ETVITMSGDDHPR (1459.7) | 2323-2335 | SEQ ID NO: 10 |
| 11 | 1459.7 | KPEHELFLVYGK (1459.7) | 521-532 | SEQ ID NO: 11 |
| 12 | 1488.7 | DVIEVAQMKGENR (1488.7) | 3980-3992 | SEQ ID NO: 12 |
| 13 | 1493.7 | VDKGGALHIYHQR (1493.7) | 456-468 | SEQ ID NO: 13 |
| 14 | 1566.9 | IVFPHGITLDLVSR (1566.9) | 366-379 | SEQ ID NO: 14 |
| 15 | 1621.8 | AVTDEEPFLIFANR (1621.8) | 3023-3036 | SEQ ID NO: 15 |
| 16 | 1680.9 | SLDPFKPFIIFSNR (1680.9) | 1263-1276 | SEQ ID NO: 16 |
| 17 | 1702.8 | GYLFWTEWGQYPR (1702.8) | 2020-2032 | SEQ ID NO: 17 |
| 18 | 1708.9 | TVLWPNGLSLDIPAGR (1708.9) | 697-712 | SEQ ID NO: 18 |
| 19 | 1749.9 | ILWIDARSDAIYSAR (1749.8) | 1448-1462 | SEQ ID NO: 19 |
| 20 | 2127.0 | SDAIYSARYDGSGHMEVLR (2127.0) | 1455-1473 | SEQ ID NO: 20 |
| 21 | 2489.2 | NSTTLVMHMKVYDESIQLDHK (2489.2) | 1825-1845 | SEQ ID NO: 21 |
| 22 | 2491.1 | IYWADAREDYIEFASLDGSNR (2491.1) | 3203-3223 | SEQ ID NO: 22 |
| 23 | 2493.1 | GFQHQRMTNGAMNVEIGNPTYK (2493.1) | 4453-4472 | SEQ ID NO: 23 |

Figure 1:
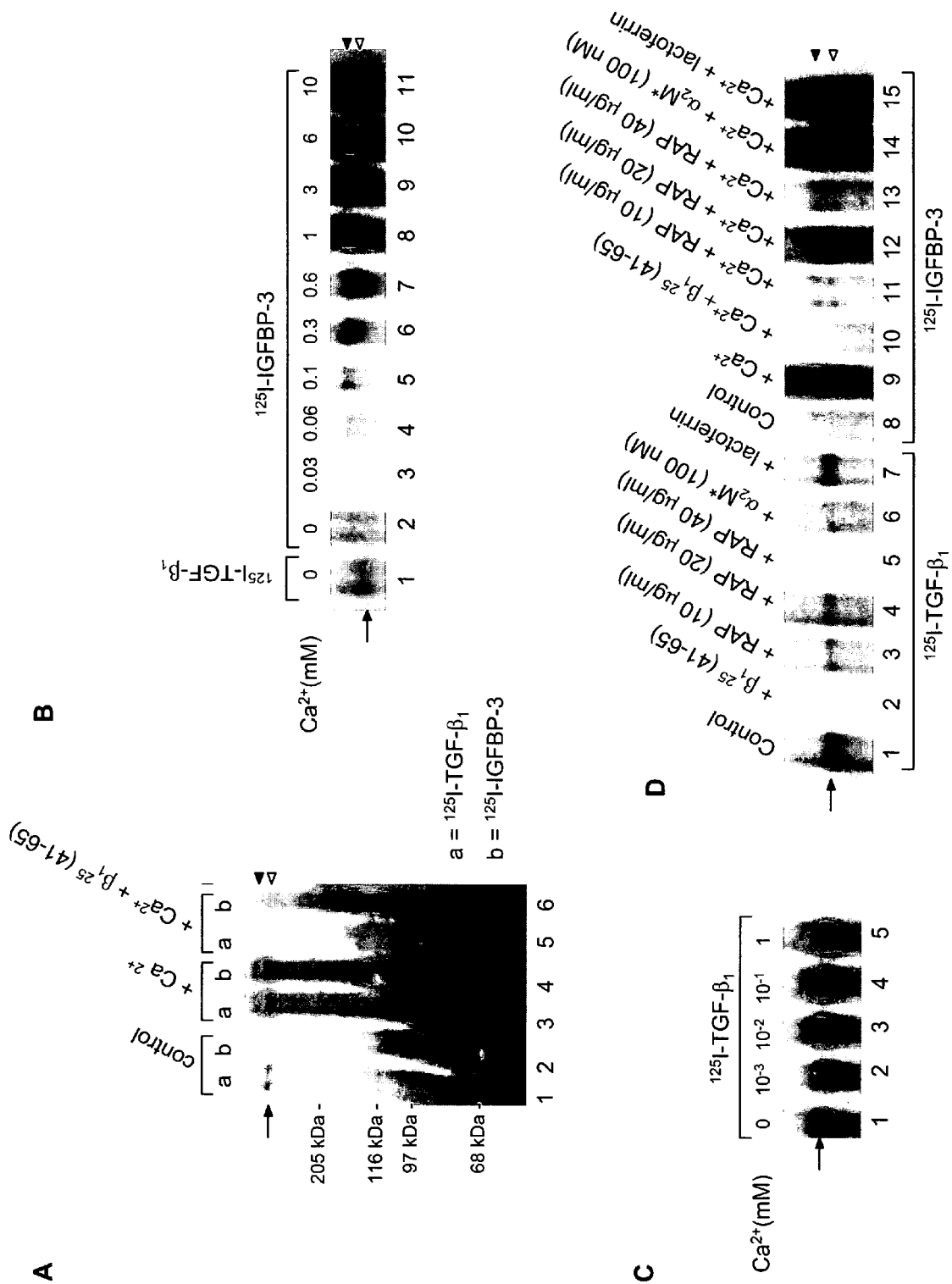
FIG. 1 depicts the effects of $Ca^{2+}$, LRP ligands and RAP on $^{125}$I-IGFBP-3 and $^{125}$I-TGF-$\beta_1$ binding to the TβR-V purified from bovine liver plasma membranes. The TβR-V purified from bovine liver plasma membranes was incubated with 10 nM 1 $^{125}$I-IGFBP-3 or 0.1 nM $^{125}$I-TGF-β1 in the presence and absence of 1 mM Ca2+ and 20 µM TGF-$\beta_1$ peptide antagonist $[\beta_1{}^{25}(41\text{-}65)]$ (A), in the presence of various concentrations as indicated of $Ca^{2+}$ (B,C) and in the presence and absence of 20 µM $\beta_1{}^{25}(41\text{-}65)$, RAP (10, 20 and 40 µg/ml), α2M* (100 nM), and lactoferrin (100 nM) with and without 1 mM Ca2+ (D). After 2.5 hr at 0° C., the $^{125}$I-IGFBP-3- or $^{125}$I-TGF-β1-TβR-V complex was cross-linked by DSS and analyzed by 5% SDS-PAGE under reducing conditions and autoradiography. The relative intensity of the $^{125}$I-IGFBP-3-TβR-V or $^{125}$I-TGF-β1-TβR-V complex band on the dried gel was quantified by a PhosphoImager. The arrow indicates the location of the $^{125}$I-TGF-β1-TβR-V complex. The closed and open arrow heads indicate the locations of the $^{125}$I-IGFBP-3 dimer-TβR-V and $^{125}$I-IGFBP-3 monomer-TβR-V complexes, respectively. The radioactivity near the 68-kDa marker represents the cross-linked $^{125}$I-IGFBP-3 dimer (15) (A, lanes 2, 4 and 6)

Finding that bovine TβR-V and human LRP are homologous prompted the inventor to examine the effects of $Ca^{2+}$ and LRP ligands [activated $\alpha_2$-macroglobulin ($\alpha_2M^*$), lactoferrin] (31,32) and an antagonist (receptor-associated protein, RAP) (33) on $^{125}$I-IGFBP-3 and $^{125}$I-TGF-$\beta_1$ binding to TβR-V. TβR-V was purified from bovine liver plasma membranes and ligand-affinity labeled (27). Both the $^{125}$I-IGFBP-3-TβR-V complex and the $^{125}$I-TGF-$\beta_1$-TβR-V complex were cross-linked by the bifunctional reagent DSS after the binding of $^{125}$I-IGFBP-3 or $^{125}$I-TGF-$\beta_1$ to purified TβR-V had been carried out in the presence and absence of $Ca^{2+}$ and of RAP. $Ca^{2+}$ is known to be required for the ligand binding activity of LRP. RAP is an LRP antagonist which blocks binding of all known ligands to LRP (33-36). As shown in FIG. 1A, binding of $^{125}$I-IGFBP-3 to purified TβR-V required the presence of $Ca^{2+}$, whereas $Ca^{2+}$ was not required for (but did enhance) binding of $^{125}$I-TGF-$\beta_1$ to TβR-V (lanes 4 versus 2 and lanes 3 versus 1, respectively). The binding of both $^{125}$I-IGFBP-3 and $^{125}$I-TGF-$\beta_1$ to purified TβR-V was blocked by a TGF-$\beta_1$ peptide antagonist, $\beta_1{}^{25}$(41-65) (28) (lanes 5 and 6). As shown in FIG. 1B, $^{125}$I-IGFBP-3 bound to TβR-V in a $Ca^{2+}$ concentration-dependent manner. $Ca^{2+}$ also enhanced $^{125}$I-TGF-$\beta_1$ binding to TβR-V in a concentration-dependent manner (FIG. 1C). Maximal binding of $^{125}$I-IGFBP-3 and $^{125}$I-TGF-$\beta_1$ occurred at 1-6 mM concentrations of $Ca^{2+}$. The two bands of the $^{125}$I-IGFBP-3-TβR-V complex on the SDS-polyacrylamide gel represent $^{125}$I-IGFBP-3 dimer and monomer complexes (15) (FIG. 1B, lane 10). The LRP antagonist, RAP, appeared to inhibit $^{125}$I-IGFBP-3 and $^{125}$I-TGF-$\beta_1$ binding to TβR-V (FIG. 1D, lanes 11-13 and lanes 3-5, respectively). Lactoferrin did not have a significant effect on either 125I-IGFBP-3 or $^{125}$I-TGF-$\beta_1$ binding to TβR-V (FIG. 1D, lanes 15 and 7, respectively). $\alpha_2M^*$ did not inhibit $^{125}$I-IGFBP-3 binding to TβR-V but blocked binding of 125I-TGF-$\beta_1$ to TβR-V (FIG. 1D, lanes 14 and 6, respectively). This inhibition was due to the fact that $\alpha_2M^*$ itself forms complexes with $^{125}$I-TGF-$\beta_1$ (37). These results indicate that, like LRP, TβR-V requires the presence of $Ca^{2+}$ for optimal ligand binding and that this ligand binding is sensitive to RAP inhibition.

It was demonstrated in the following experiments that RAP inhibits binding of IGFBP-3 and TGF-$\beta_1$ to cell surface receptors and blocks IGFBP-3-induced growth inhibition.

Figure 2:
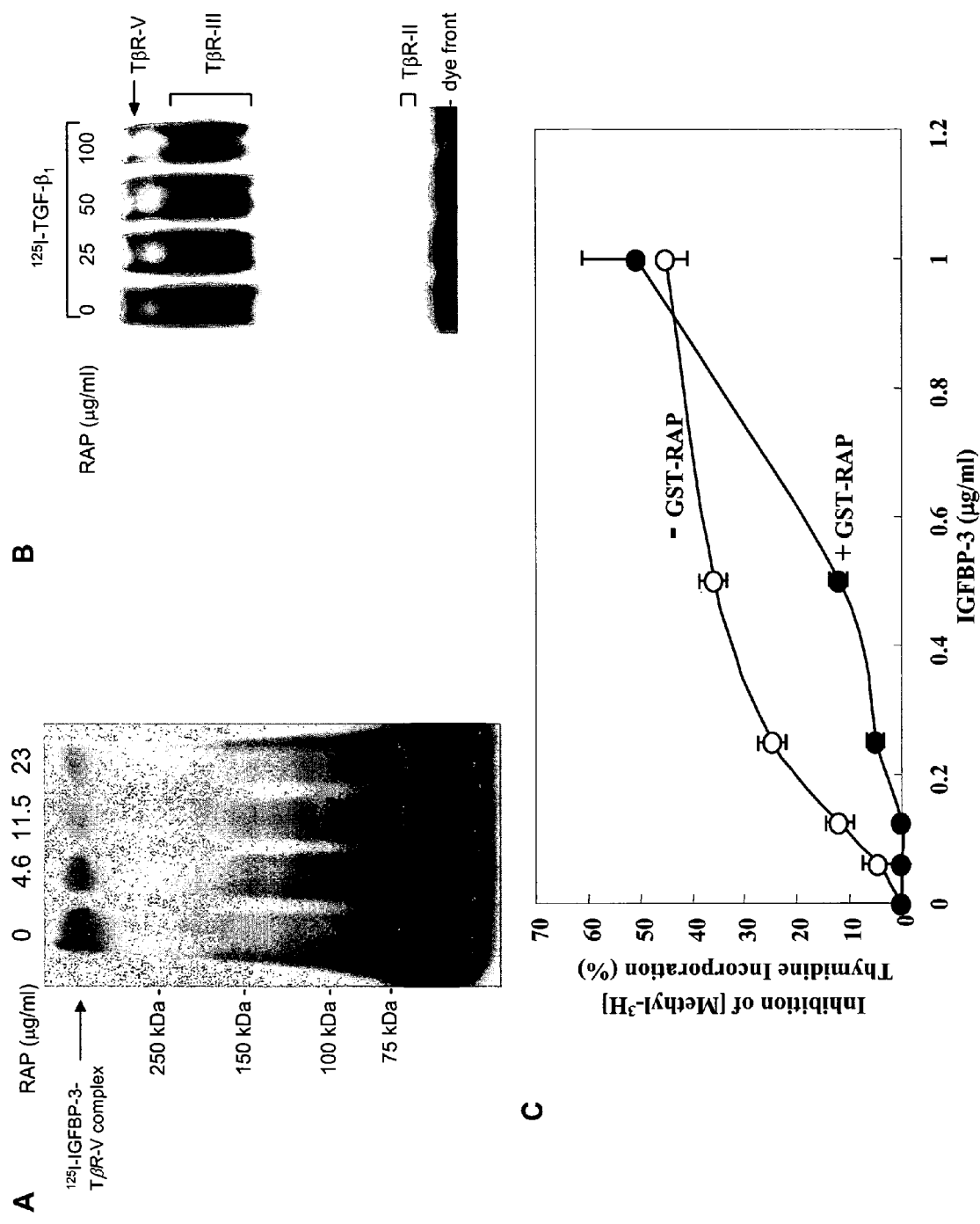
FIG. 2 depicts the effects of RAP on $^{125}$I-IGFBP-3 (A) and $^{125}$I-TGF-β1 binding (B) to TβR-V and on IGFBP-3-induced inhibition of DNA synthesis (C) in Mv1Lu cells. (A,B) Cells were incubated with $^{125}$I-IGFBP-3 (10 nM) or $^{125}$I-TGF-$\beta_1$ (0.1 nM) in the presence of various concentrations of RAP as indicated. After 2.5 hr at 0° C., the $^{125}$I-IGFBP-3-TβR-V complex or $^{125}$I-TGF-$\beta_1$-TGF-β receptor complexes were cross-linked by DSS and analyzed by autoradiography. The relative intensity of the $^{125}$I-IGFBP-3-TβR-V complex or $^{125}$I-TGF-$\beta_1$-TGF-β receptor complex on the dried gel was quantified by a PhosphoImager. The arrow indicates the location of the $^{125}$I-TGF-β-TβR-V complex or the $^{125}$I-IGFBP-3-TβR-V complex. The bracket indicates the locations of the $^{125}$I-TGF-$\beta_1$-TβR-III and -TβR-II complexes. The $^{125}$I-TGF- $\beta_1$-T$\beta$R-I complex co-migrated with the dye front. The $^{125}$I-TGF-$\beta_1$-T$\beta$R-II complex can be seen upon longer time exposure of the autoradiogram. (C) Cells were incubated with various concentrations, as indicated, of IGFBP-3 and GST-RAP (100 μg/ml). During incubation, GST-RAP (100 μg/ml) or the solvent vehicle was repeatedly added to the medium hourly for 8 hr. After further incubation for 10 hr, the DNA synthesis of cells was determined by measuring [methyl-$^3$H] thymidine incorporation into cellular DNA. The [methyl-$^3$H] thymidine incorporation in cells treated without IGFBP-3 (35,219±2,670 cpm/well) was taken as 0% inhibition. Each data point is the mean±S.D. of quadruplicate determinations. The DNA synthesis inhibition in cells treated with GST-RAP and various concentrations of IGFBP-3 (0.125, 0.25 and 0.5 μg/ml) was significantly less than cells treated without GST-RAP but with the same concentrations of IGFBP-3 (Student's t test, p<0.001). Data are representative of four similar experiments.

Mv1Lu cells are a well-established model system for investigating TGF-$\beta$ activities and receptor functions. Therefore, the effect of RAP on $^{125}$I-IGFBP-3 and $^{125}$I-TGF-$\beta_1$ binding to T$\beta$R-V was studied in Mv1Lu cells using affinity labeling (binding and cross-linking). As shown in FIG. 2, RAP inhibited $^{125}$I-IGFBP-3 binding to T$\beta$R-V in a concentration-dependent manner with an IC$_{50}$ of ~5 µg/ml (FIG. 2A), whereas RAP only partially inhibited $^{125}$I-TGF-$\beta_1$ binding to T$\beta$R-V and T$\beta$R-III in Mv1Lu cells (FIG. 2B). Since RAP strongly inhibited 125I-IGFBP-3 binding to T$\beta$R-V in Mv1Lu cells, it was anticipated that RAP would block IGFBP-3-induced growth suppression in these cells. Therefore the effect of repeated doses of GST-RAP (a fusion protein of glutathione S-transferase and RAP) on DNA synthesis of Mv1Lu cells was examined. It was found that a single dose (100 µg/ml) of GST-RAP was unable to block DNA synthesis of Mv1Lu cells during an 18 hr incubation. This was consistent with a report that RAP was no longer effective in blocking $\alpha_2$M* association and degradation in cells after a >1 hr incubation time, presumably due to efficient cellular binding and degradation of RAP under culture conditions (38). For this reason, Mv1Lu cells were incubated with various concentrations of IGFBP-3 and GST-RAP (100 µg/ml) or the solvent vehicle, each (GST-RAP or the solvent vehicle) added to the culture medium hourly for 8 hr. After further incubation for 10 hr, DNA synthesis of the cells was determined. As shown in FIG. 2C, the repeated doses of GST-RAP effectively blocked growth suppression induced by 0.5 µg/ml IGFBP-3 in these epithelial cells. RAP was also used for the same experiment and yielded similar results (data not shown). Since RAP is a well-known LRP antagonist, these results support the notion that T$\beta$R-V is functionally identical to LRP.

It was demonstrated in the following experiments that $^{125}$I-IGFBP-3-affinity labeled T$\beta$R-V is immunoprecipitated by antibodies to LRP.

Figure 3:
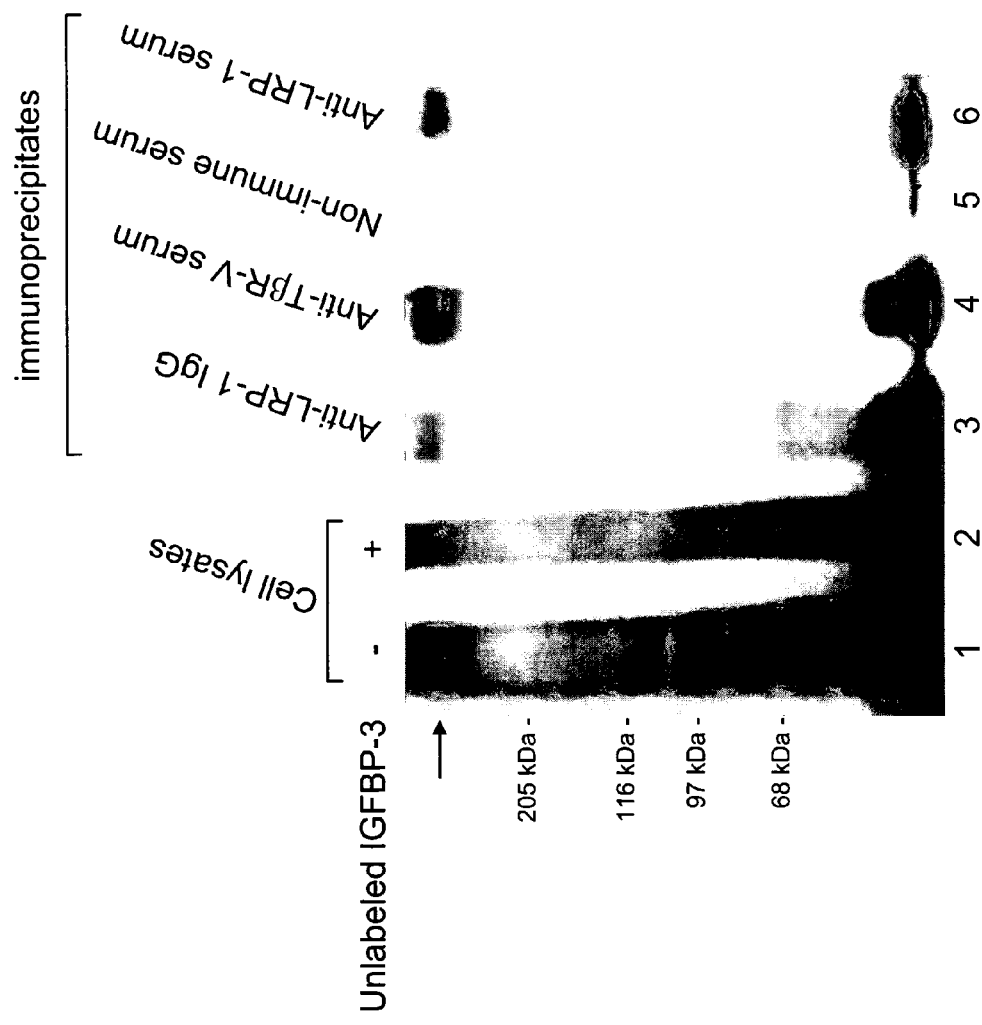
FIG. 3 depicts the immunoprecipitation of the $^{125}$I-IGFBP-3-affinity labeled T$\beta$R-V in Mv1Lu cells by antibodies to LRP and T$\beta$R-V. Cells were incubated with 10 nM $^{125}$I-IGFBP-3 in the presence or absence of 100-fold excess of unlabeled IGFBP-3. After 2.5 hr at 0° C., the $^{125}$I-IGFBP-3-T$\beta$R-V complex was cross-linked by DSS and directly analyzed by 5% SDS-PAGE under reducing conditions and auto-radiography (lanes 1 and 2) or subjected to immunoprecipitation using anti-LRP IgG (lane 3), anti-T$\beta$R-V serum (lane 4), anti-LRP serum (lane 6) and non-immune serum (lane 5). The immunoprecipitates were analyzed by 5% SDS-PAGE under reducing conditions and autoradiography. The arrow indicates the location of the $^{125}$I-IGFBP-3-affinity labeled T$\beta$R-V.

Previously, the inventor had shown that $^{125}$I-IGFBP-3-affinity labeled T$\beta$R-V could be immunoprecipitated by antiserum to T$\beta$R-V (14). If T$\beta$R-V is identical to LRP, $^{125}$I-IGFBP-3-affinity labeled T$\beta$R-V should be immunoprecipitated by antisera to either LRP or T$\beta$R-V. To test this, T$\beta$R-V in Mv1Lu cells was 125I-IGFBP-3-affinity labeled; then the $^{125}$I-IGFBP-3-affinity labeled T$\beta$R-V was immunoprecipitated by antibodies to LRP or T$\beta$R-V. As shown in FIG. 3, T$\beta$R-V was affinity-labeled with $^{125}$I-IGFBP-3 in the presence of DSS (prior to immunoprecipitation) (lane 1). The $^{125}$I-IGFBP-3 affinity labeling of T$\beta$R-V was blocked in the presence of 100-fold excess of unlabeled IGFBP-3 (lane 2). The $^{125}$I-IGFBP-3-affinity labeled T$\beta$R-V was immunoprecipitated by anti-LRP IgG, anti-LRP serum and anti-T$\beta$R-V serum (lanes 3, 6 and 4, respectively) but not by non-immune serum (lane 5). Anti-LRP IgG and anti-LRP sera were kindly provided by Drs. Guojan Bu, Joachim Herz and Dudley Strickland. Together with the results described above, these results suggest that T$\beta$R-V is identical with LRP.

It was demonstrated in the following experiments that cells lacking or expressing low levels of T$\beta$R-V also express no to low levels of LRP.

Figure 4:
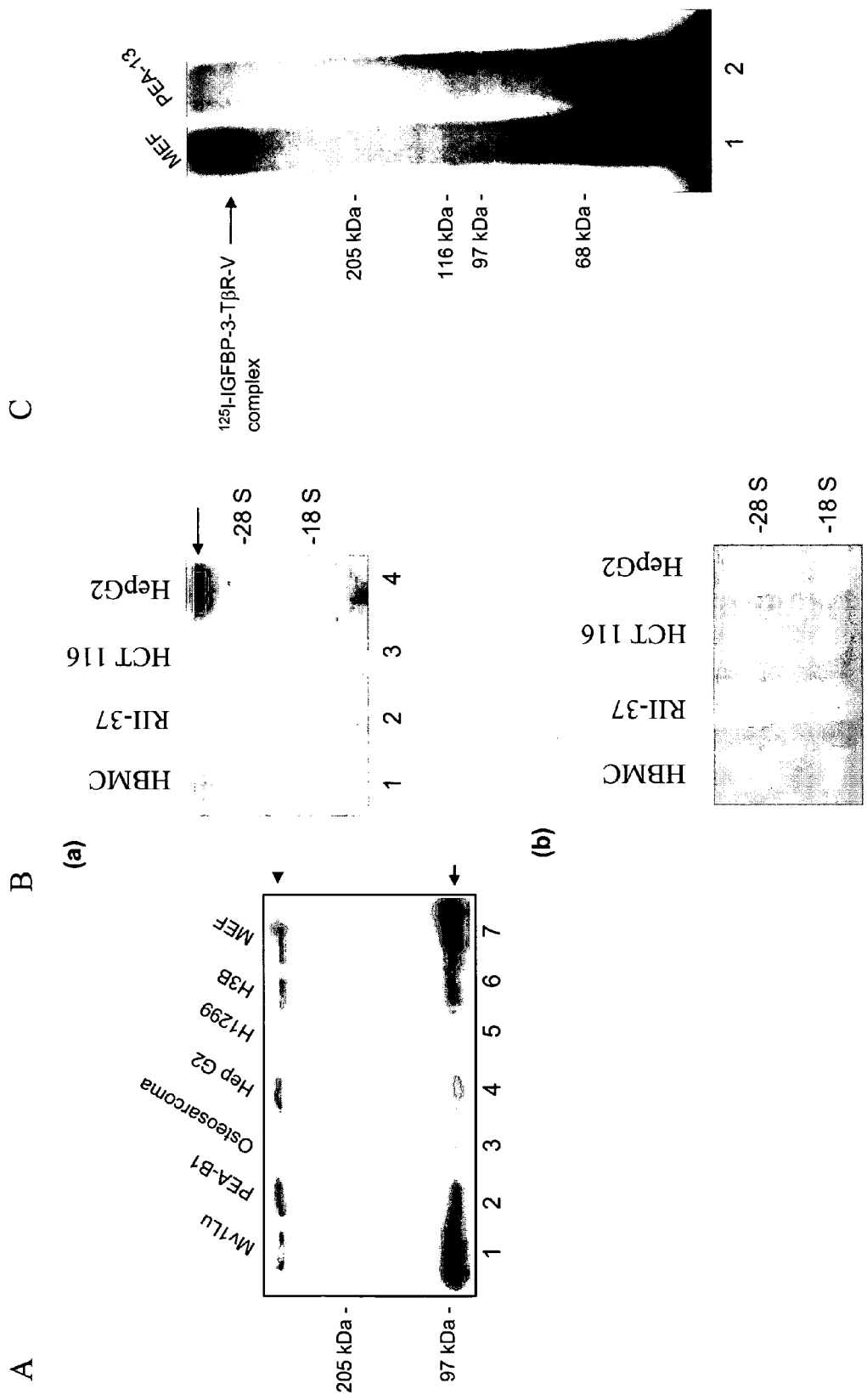
FIG. 4 depicts a Western blot analysis (A), Northern blot analysis (B) and $^{125}$I-IGFBP-3 affinity labeling (C) of LRP/T$\beta$R-V in carcinoma cells and other cell types. (A) Protein from MEF, PEA-B1, Mv1Lu cells, osteosarcoma, HepG2, H1299, and H3B cells were subjected to 5% SDS-PAGE under reducing conditions, electrotransfer and Western blot analysis using anti-LRP light chain antiserum. PEA-B1 cells were Mv1Lu mutant cells, which expressed LRP at levels comparable to those in wild type cells. The arrow and arrowhead indicate the locations of the LRP light chain (85 kDa) and intact LRP (600 kDa), respectively. (B) Northern blot analysis of LRP in human colorectal carcinoma cells (HCT116 and RII37 cells), HepG2 cells and human bone marrow-derived mesenchymal stem cells (HBMC cells) was performed (a). Ribosomal RNAs in each sample were shown in (b). The arrow indicates the location of the LRP transcript (~15 kb). The bar indicates the locations of ribosomal RNAs (28 S and 18 S). (C) MEF and PEA-13 cells were affinity-labeled with $^{125}$I-IGFBP-3 using the cross-linking agent DSS and analyzed by 5% SDS-PAGE under reducing conditions and autoradiography. The arrow indicates the location of the 125I-IGFBP-3-affinity labeled T$\beta$R-V.

T$\beta$R-V coexpresses with T$\beta$R-I, T$\beta$R-II and T$\beta$R-III in all normal cell types examined. Many carcinoma cells (e.g., HCT116, H1299, HepG2, MCF-7 and H3B cells) do not express detectable T$\beta$R-V, or express very low levels of T$\beta$R-V (13,14). If T$\beta$R-V is LRP, one should see correspondingly non-detectable or very low levels of expression of LRP in these carcinoma cells. To test this, Western blot analysis was performed using antiserum to the LRP light chain. The light chain of LRP contains the transmembrane domain, is stable and is therefore appropriate to use as an indicator for the measurement of LRP expression. The recovery of the LRP heavy chain varies depending on culture conditions because it non-covalently associates with the LRP light chain (25). As shown in FIG. 4A, carcinoma cells (HepG2, H1299 and H3B cells) and osteosarcoma cells expressed low levels of LRP (lanes 3-6) whereas normal or non-transformed cells such as mouse embyronic fibroblasts (MEF), Mv1Lu cells and Mv1Lu mutant cells (PEA-B1 cells, which have acceleration of degradation of internalized LRP ligands) exhibited high levels of LRP (lanes 1, 2 and 7). On the other hand, human colorectal carcinoma cells (HCT116 and RII37 cells), which were originally identified as T$\beta$R-II-deficient cells but later also found to be deficient in T$\beta$R-V (14,18), did not express LRP as demonstrated by Northern blot analysis (FIG. 4Ba, lanes 2 and 3). PEA-13 cells (which were derived from an LRP null embryo) also showed no expression of T$\beta$R-V as determined by $^{125}$I-IGFBP-3-affinity labeling (FIG. 4C, lane 2). These results support the fact that LRP is identical to T$\beta$R-V.

It was demonstrated in the following experiments that reduced expression of LRP attenuates the growth inhibitory response to IGFBP-3 and TGF-$\beta_1$ in Mv1Lu cells.

Figure 5:
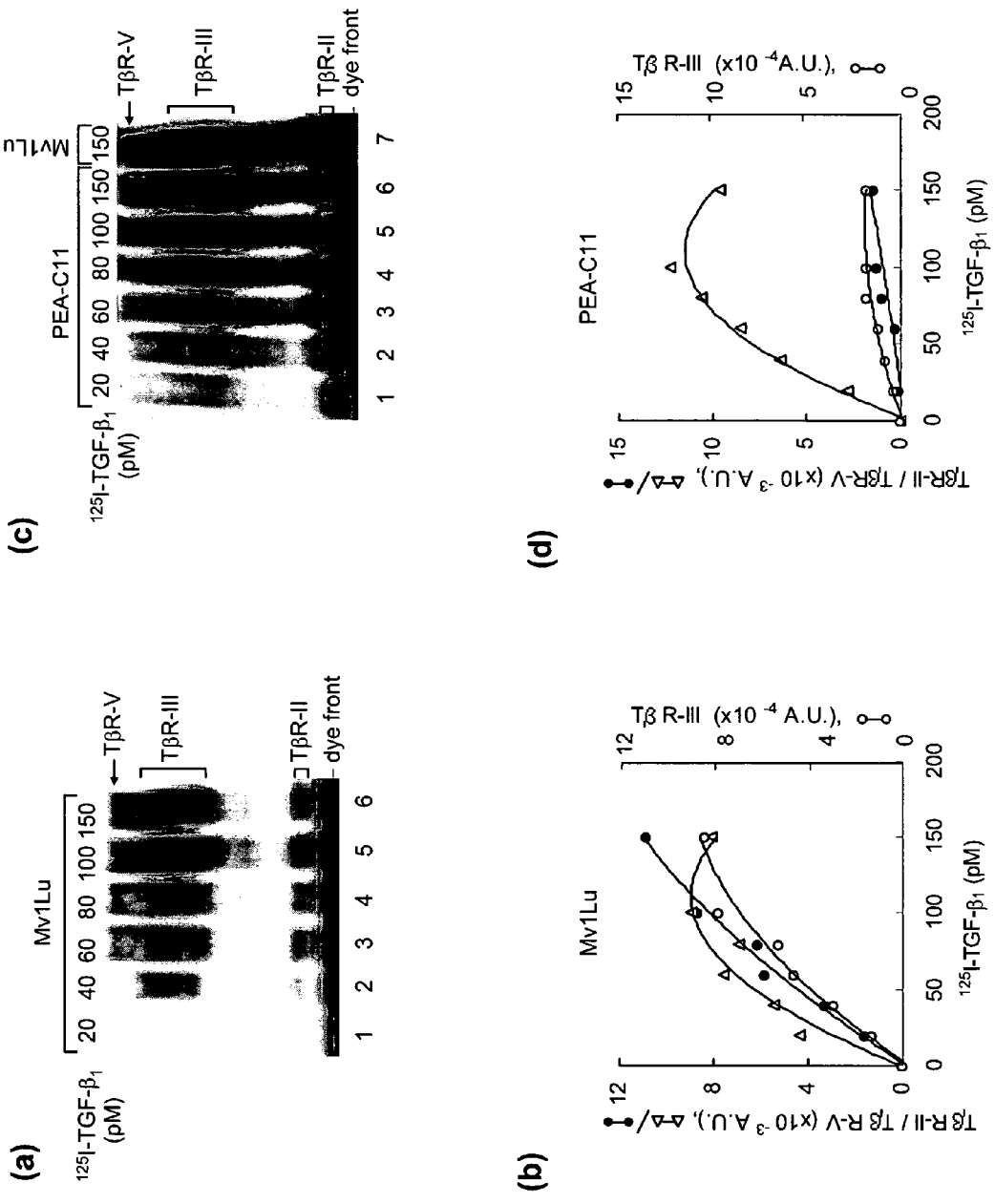
FIG. 5 depicts a Western blot analysis (A), $^{125}$I-cell surface labeling (B) and $^{125}$I-TGF-$\beta_1$-affinity labeling (C) of LRP-1/T$\beta$R-V in Mv1Lu and PEA-C11 cells. (A) Equal amounts (~200 μg) of protein from each type of cells (PEA-C11, Mv1Lu, PEA-13 and MEF) were subjected to Western blot analysis using antiserum to LRP-1 light chain following 4.5-7.5% gradient SDS-PAGE under reducing conditions and electrotransfer. The relative intensity of the LRP-1 light chain was quantitated by densitometry. The arrow and arrowhead indicate the locations of the LRP-1 light chain and the intact LRP-1, respectively. The antiserum to LRP-1 light chain reacts with the LRP-1 light chain and intact LRP-1. (B) Cell surface proteins in Mv1Lu and PEA-C11 cells were labeled with $^{125}$I by treating cells with Na$^{125}$I in the presence of $H_2O_2$ and lactoperoxidase. The $^{125}$I-labeled cell lysates were immunoprecipitated with antisera to LRP-1 light chain and heavy chain. The immunoprecipitates were analyzed by 5% SDS-PAGE under reducing conditions and autoradiography with two different exposure times, 4 hr (a) and overnight (b). The bracket indicates the locations of the intact LRP-1/LRP-1 heavy chain and the LRP-1 light chain. The relative intensities of the LRP-1 light and heavy chains (on the dried gel) were determined by a PhosphoImager. (C) The cell surface TGF-$\beta$ receptors in Mv1Lu (a,b) and PEA-C11 (c,d) cells were affinity-labeled with $^{125}$I-TGF-$\beta_1$ by cross-linking with DSS following binding of $^{125}$I-TGF-$\beta_1$ to cells. The cell lysates of $^{125}$I-TGF-$\beta_1$-affinity labeled cells were analyzed by 5% SDS-PAGE under reducing conditions and autoradiography (a,c). The arrow indicates the location of the $^{125}$I-TGF-$\beta_1$-T$\beta$R-V complex. The bracket indicates the locations of the $^{125}$I-TGF-$\beta_1$-T$\beta$R-II and $^{125}$I-TGF-$\beta_1$-T$\beta$R-III complexes. The intensities of the $^{125}$I-TGF-$\beta_1$-affinity labeled TGF-$\beta$ receptors (T$\beta$R-V, T$\beta$R-III and T$\beta$R-II) (on the dried gel) were quantified with a PhosphoImager (b,d).

Mv1Lu cells are a standard model system to investigate TGF-$\beta$ activity and functions of TGF-$\beta$ receptors, including T$\beta$R-V. To define the role of LRP in IGFBP-3-induced growth inhibition, Mv1Lu cell mutants were created using ethyl methane sulfonate mutagenesis (29). Those expressing low levels of LRP were selected by Pseudomonas exotoxin selection using published procedures (29). Pseudomonas exotoxin selection yields mutant cells with reduced expression of LRP. A representative clone was designated as PEA-C11 cells. Western blot analysis (FIG. 5A) revealed that the PEA-C11 cells produced <10% of the amount of LRP produced by the parent cells (lane 4 versus lane 3). Normally, ~90-95% of LRP is localized intracellularly. To evaluate the cellular distribution of LRP, the cell surface expression of LRP was examined in these mutant cells by $^{125}$I-cell surface labeling followed by immunoprecipitation. As shown in FIG. 5B, PEA-C11 cells expressed the LRP light chain (which contains the transmembrane domain of LRP) at levels comparable to that in Mv1Lu cells (FIG. 5Ba, lane 1 versus lane 3). However, the amount of the heavy chain of LRP, which non-covalently associates with the transmembrane light chain, in PEA-C11 cells was greatly reduced compared to that found in Mv1Lu cells (FIG. 5Bb, lane 2 versus lane 4). This suggests that the heavy chain of cell-surface LRP is less stable (or less stably associated with the light chain) in PEA-C11 cells. Approximately 15% of the heavy chain remained associated with the light chain of cell-surface LRP in these mutant cells under these experimental conditions as determined by $^{125}$I-cell-surface labeling and immunoprecipitation.

The cell-surface expression of T$\beta$R-V/LRP in Mv1Lu and PEA-C11 cells was also examined by cell-surface $^{125}$I-TGF-$\beta_1$ affinity labeling. As shown in FIG. 5C, the amount of $^{125}$I-TGF-$\beta_1$-affinity labeled T$\beta$R-V in PEA-C11 cells was less than that found in Mv1Lu cells (FIG. 5Cc, lanes 6 versus 7). PEA-C11 cells contained about 15% as much T$\beta$R-V as the parent Mv1Lu cells. It is of interest to note that concomitant attenuation of T$\beta$R-III expression was also observed in these mutant cells (FIG. 5Cd versus FIG. 5Cb). These results suggest that the PEA-C11 cells possess ~15% as much cell-surface T$\beta$R-V/LRP as the parent cells.

Figure 6:
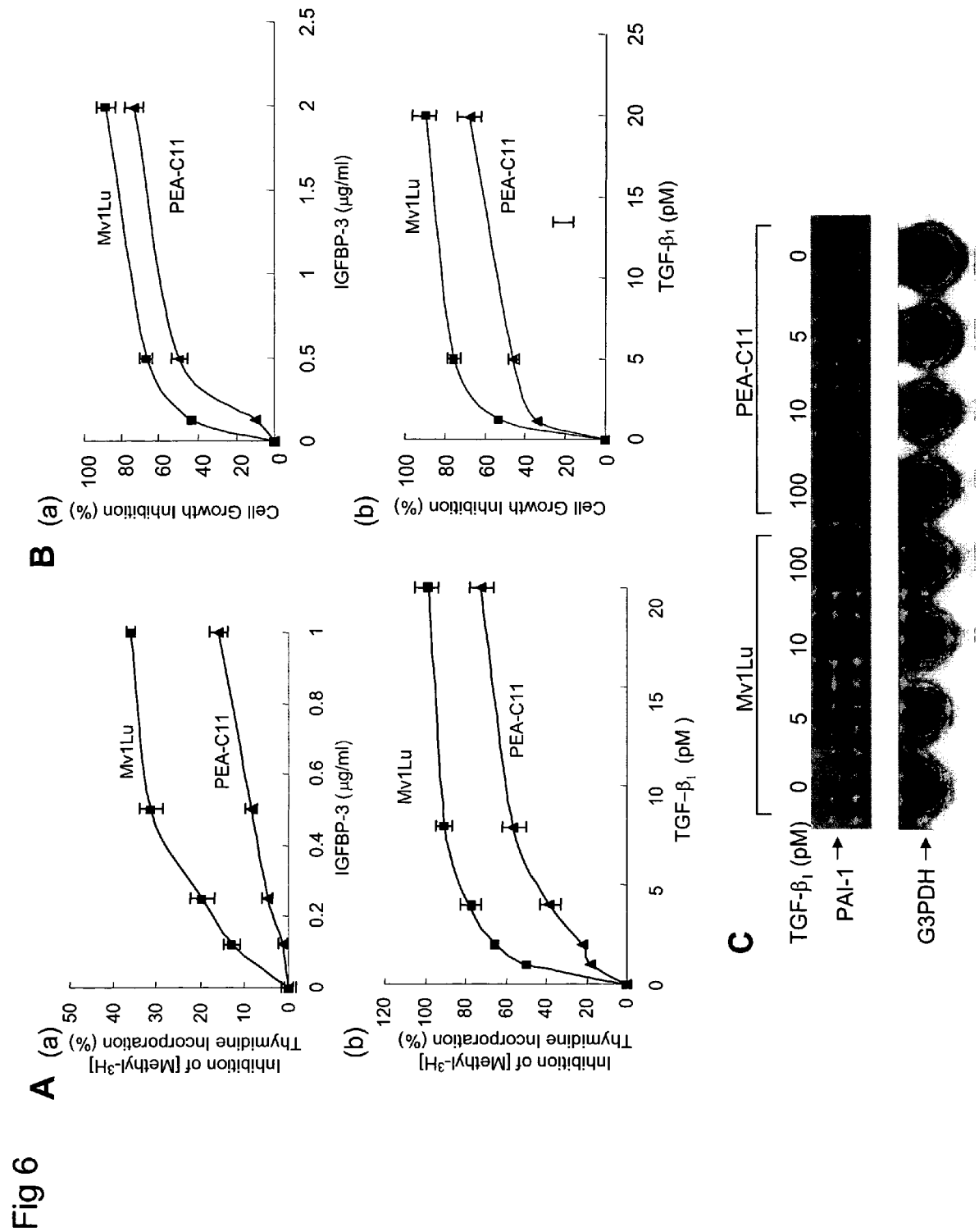
FIG. 6 depicts the effects of IGFBP-3 and TGF-$\beta_1$ on DNA synthesis (A), cell growth (B) and PAI-1 expression (C) in Mv1Lu and PEA-C11 cells. (A,B) Cells were incubated with various concentrations of IGFBP-3 (a) or TGF-$\beta_1$ (b) as indicated. DNA synthesis and cell growth were determined by measuring the [methyl-$^3$H] thymidine incorporation into cellular DNA after 18 hr incubation (A) and by counting cell number after a 4-day incubation (B), respectively. The [methyl-$^3$H] thymidine incorporation in cells treated without IGFBP-3 and TGF-$\beta_1$ (29,170±1,657 and 59,947±7,692 cpm/well for Mv1Lu and PEA-C11 cells, respectively) were taken as 0% inhibition. The cell numbers (33±2 and 38±3×10$^4$ cells for Mv1Lu and PEA-C11 cells, respectively) in cells treated without IGFBP-3 or TGF-$\beta_1$ were taken as 0% inhibition. Each data point is the mean±S.D. of quadruplicate determinations. The DNA synthesis or cell growth inhibition in PEA-C11 cells was significantly less at all data points (except 0 concentration of IGFBP-3 or TGF-$\beta_1$) when compared with Mv1Lu cells (Student's t test, p<0.05). Data are representative of eight similar experiments. (C) Cells were incubated with various concentrations of TGF-$\beta_1$ as indicated. After 2 hr at 37° C., the PAI-1 expression was determined by Northern blot analysis. The expression of glyceraldehyde-3-phosphate dehydrogenase (G3PDH) was used as control. The relative levels of the transcripts were quantified by a PhosphoImager. Data are representative of four similar experiments.

The growth inhibitory response to TGF-$\beta_1$ and IGFBP-3 in Mv1Lu and PEA-C11 cells was examined. PEA-C11 cells showed a diminished response to TGF-$\beta_1$- and IGFBP-3-induced growth inhibition as determined by measuring [methyl-$^3$H] thymidine incorporation into cellular DNA (FIG. 6A) and by counting cell number (FIG. 6B). At 0.5 µg/ml, IGFBP-3 inhibited DNA synthesis and cell growth in PEA-C11 cells by ~10% and ~45%, respectively, as compared to ~30% and ~70% in Mv1Lu cells (FIG. 6Aa and FIG. 6Ba). TGF-$\beta_1$ (20 pM) blocked DNA synthesis and cell growth in PEA-C11 cells by ~70% as compared with ~90-100% inhibition in Mv1Lu cells (FIG. 6Ab and FIG. 6Bb). By contrast, PEA-C11 cells exhibited a level of TGF-$\beta_1$-induced transcriptional activation of plasminogen activator inhibitor-1 (PAI-1) comparable to that observed in Mv1Lu cells (FIG. 6C). PEA-C11 cells also exhibited a growth response to basic fibroblast growth factor (bFGF) and epidermal growth factor (EGF) equally well as observed in Mv1Lu cells (data not shown). These results indicate that decreased expression of LRP induced by mutagenesis of Mv1Lu cells leads to attenuation of their growth inhibitory response (to IGFBP-3 and TGF-$\beta_1$) without significant effect on the TGF-$\beta_1$-induced transcriptional activation of PAI-1 or growth regulation by other growth factors such as bFGF and EGF.

It was demonstrated in the following experiments that LRP-null mouse embryonic fibroblasts lack the growth inhibitory response to TGF-$\beta_1$.

The effects of IGFBP-3 and TGF-$\beta_1$ on DNA synthesis and cell growth in MEF cells and fibroblasts from a LRP-null embryo (PEA-13 cells) were determined (39). As shown in FIG. 7, TGF-$\beta_1$ (1.25 to 20 pM) inhibited DNA synthesis (FIG. 7A) and cell growth (FIG. 7B) in MEF cells but not in PEA-13 cells. TGF-$\beta_1$ (20 pM) exhibited ~30-40% inhibition of DNA synthesis and cell growth in MEF cells. In contrast, TGF-$\beta_1$ (20 pM) stimulated DNA synthesis and cell growth by up to only 20% in PEA-13 cells. IGFBP-3 did not appear to have a significant effect on DNA synthesis and cell growth in either MEF cells or PEA-13 cells at concentrations up to 1 µg/ml (data not shown). On the other hand, TGF-$\beta_1$ was capable of transcriptional activation of PAI-1 equally well in both MEF and PEA-13 cells (FIG. 7C). These results support the fact that LRP/T$\beta$R-V is important for TGF-$\beta_1$-induced growth suppression. They also suggest that, in PEA-13 cells, the absence of LRP/T$\beta$R-V does not affect TGF-$\beta_1$-induced PAI-1 expression, which is known to be primarily mediated by the T$\beta$R-I/T$\beta$R-II complex signaling in the cell systems studied so far.

It was demonstrated in the following experiments that LRP expression by stable transfection with LRP cDNA restores the growth inhibitory response to IGFBP-3 and TGF-$\beta_1$ in a human lung carcinoma cell line.

To prove that growth suppression is mediated by LRP/T$\beta$R-V, the growth inhibitory response to IGFBP-3 and TGF-$\beta_1$ was restored in H1299 cells (human lung carcinoma cells) by transfecting those cells with a polynucleotide encoding LRP. H1299 cells were chosen for two reasons: 1) H1299 cells are derived from lung epithelial cells which, in general, express ≦30% as much LRP as fibroblasts, (e.g., MEF cells). H1299 cells express very low levels of endogenous LRP. 2) IGFBP-3 and TGF-$\beta_1$ do not inhibit DNA synthesis or cell growth in H1299 cells.

H1299 cells were stably transfected with LRP cDNA or vector only, cloned under G418 selection and named H1299/LRP and H1299/vector cells, respectively. The expression of LRP was determined by Western blot analysis using antisera to LRP light chain (FIG. 8A[a]) and heavy chain (FIG. 8A[b]). The effects of IGFBP-3 and TGF-$\beta_1$ on DNA synthesis and cell growth in these cells were then examined. As shown in FIGS. 8B,C, both IGFBP-3 and TGF-$\beta_1$ inhibited DNA synthesis (FIG. 8B) and cell growth (FIG. 8C) of H1299/LRP cells whereas they acted as mitogens or growth stimulators for H1299/vector cells. On the other hand, TGF-$\beta_1$ induced transcriptional activation of PAI-1 in both H1299/LRP cells and H1299/vector cells. These results indicate that stable transfection of H1299 cells with LRP cDNA can restore the growth inhibitory response to IGFBP-3 and TGF-$\beta_1$ without significantly altering TGF-$\beta_1$-induced transcriptional activation of PAI-1 in these cells.

Discussion

Several lines of evidence presented in this example suggest that T$\beta$R-V is identical with LRP. These include: 1) The molecular masses of 23 tryptic peptides of T$\beta$R-V are identical with those of the corresponding tryptic peptides of human LRP. 2) The LRP antagonist RAP inhibits binding of $^{125}$I-IGFBP-3 and $^{125}$I-TGF-$\beta_1$ to T$\beta$R-V purified from bovine liver plasma membranes and in Mv1Lu cells as determined by affinity labeling. 3) $^{125}$I-IGFBP-3-affinity labeled T$\beta$R-V in Mv1Lu cells is immunoprecipitated by antisera to either LRP or T$\beta$R-V. 4) RAP blocks IGFBP-3-induced inhibition of DNA synthesis in Mv1Lu cells. 5) Mutagenized Mv1Lu cells selected for reduced expression of LRP show attenuated expression of T$\beta$R-V as determined by $^{125}$I-TGF-$\beta_1$-affinity labeling. 6) Cells lacking T$\beta$R-V or expressing low levels of T$\beta$R-V also lack or express little LRP, as demonstrated by Western blot analysis and by $^{125}$I-IGFBP-3 affinity labeling. 7) Stable transfection of H1299 cells with LRP cDNA confers sensitivity to growth inhibition by TGF-$\beta_1$ and IGFBP-3.

LRP is known to be an endocytic receptor, which mediates uptake and degradation of many structurally unrelated molecules and is responsible for their plasma clearance (31,32, 34). The embryonic lethality of the LRP null mutation strongly suggests that LRP may have important biological functions other than its involvement in catabolism of ligand molecules (32,39). The LRP ligand, $\alpha_2$M*, has recently been shown to induce signaling in several cell types (32). The finding that T$\beta$R-V is identical to LRP, presented here for the first time, has disclosed a novel growth regulatory function of LRP, which may be important, even necessary, during embryonic development. This novel and surprising discovery also raises the question of how LRP, a well-known endocytotic receptor, mediates IGFBP-3-induced growth inhibition and why it is required for TGF-$\beta_1$-induced growth inhibition. LRP binds many structurally unrelated ligand molecules. A few of them have been reported to regulate cell growth, but the mechanisms underlying the regulation remain unknown (32, 36). It is possible that IGFBP-3 or TGF-$\beta_1$ bind to T$\beta$R-V/LRP at a specific site which is distinct from those for binding other ligands and cause LRP activation (specific conformational change) resulting in cellular signaling which leads to growth inhibition. This is supported by the observation that the LRP ligands lactoferrin and $\alpha_2$M* did not inhibit binding of $^{125}$I-IGFBP-3 and $^{125}$I-TGF-$\beta_1$ to the purified T$\beta$R-V. It is also possible that IGFBP-3 and TGF-$\beta_1$, both dimeric proteins (noncovalently and covalently bound, respectively), may be capable of activating LRP by inducing dimerization or oligomerization.

Unlike the case in wild-type cells (Mv1Lu cells), high concentrations of TGF-$\beta_1$ (~50-100 pM) inhibit DNA synthesis only weakly in Mv1Lu mutants DR26 and R1B cells which lack functional T$\beta$R-II and T$\beta$R-I, respectively (24, 40). In fact, TGF-$\beta_1$ at <10 pM is ineffective in inhibiting growth of these mutant cells. This suggests that TβR-I and TβR-II are obligatory for the growth inhibitory response to TGF-$β_1$, especially at low concentrations. The moderate effect of high concentrations of TGF-$β_1$ on DNA synthesis in DR26 and R1B cells is presumably mediated by TβR-V/LRP, which is known to be present in these cells (24). In contrast to TGF-$β_1$, IGFBP-3 is a potent growth inhibitor in both DR26 and R1B cells (14). It inhibits DNA synthesis in DR26 cells more strongly than in wild-type Mv1Lu cells. The ability of IGFBP-3 to induce growth inhibition in DR26 and R1B cells suggests that the TβR-V/LRP/IGFBP-3 receptor can mediate growth inhibition in the absence of TβR-I and TβR-II.

It was also demonstrated in this example that the Mv1Lu mutant cells (PEA-C11 cells) express only 15% as much cell surface LRP as Mv1Lu cells and exhibit an attenuated growth inhibitory response to IGFBP-3 and TGF-$β_1$. This is consistent with the fact that LRP/TβR-V mediates the IGFBP-3- and TGF-$β_1$-induced growth inhibitory response in responsive cells. The requirement of LRP/TβR-V for both IGFBP-3- and TGF-$β_1$-induced growth inhibition is further evidenced by the observation that LRP-null mouse embryonic fibroblasts (PEA-13 cells) fail to respond to growth inhibition induced by TGF-$β_1$ as wild-type MEF cells do. Furthermore, stable transfection with LRP cDNA of H1299 cells, a human lung carcinoma cell line which expresses very low levels of LRP and is insensitive to IGFBP-3 and TGF-$β_1$ growth inhibition, restores the sensitivity to both IGFBP-3 and TGF-$β_1$.

The molecular basis for the requirement of LRP for growth inhibition induced by TGF-$β_1$ is herein further described. Nonetheless, the skilled artisan might reasonably expect that, in addition to its potential signaling functions (41,42), the endocytic function of LRP might also be indirectly involved in signaling mediated by the TβR-I/TβR-II heterocomplex. It has recently been reported that the endosomal localization of the TβR-I/TβR-II heterocomplex-mediated signaling complex assembly is important for signaling which leads to cellular responses (43). TβR-V has been shown to physically associate with TβR-I (24). It might influence endocytosis of the TβR-I/TβR-II heterocomplex following stimulation by low concentrations of TGF-$β_1$. However, the inventor did not observe any significant differences in the endocytosis and degradation rates of cell surface receptor-bound $^{125}$I-TGF-$β_1$ and TGF-$β_1$-stimulated phosphorylation of Smad2/3 between MEF and PEA-13 cells or between H1299/LRP and H1299/vector cells. Nevertheless, the similarity in TGF-$β_1$-stimulated transcriptional activation of PAI-1 between PEA-13 and MEF cells and between H1299/LRP and H1299/vector cells suggests that TβR-I/TβR-II-mediated signaling (which leads to expression of PAI-1 and other genes) is still functional in all these cells.

TGF-β is the most potent known growth inhibitor for epithelial cells. Loss of the growth inhibitory response to TGF-β is believed to contribute to malignancy of many human carcinoma cells and other cancer cell types (45,46). Lack of TβR-I or TβR-II can explain, in part, why these carcinoma cells do not exhibit the growth inhibitory response to TGF-β. However, stable transfection by TβR-I or TβR-II cDNA of some of these carcinoma cells failed to restore the growth inhibitory response (14,18), suggesting that other alterations including concomitant loss or attenuation of expression of other receptor types (e.g., TβR-V) and post-receptor signaling defects might have occurred in these carcinoma cells. Recently, by introducing a dominant negative mutant TβR-II into a series of cell lines derived from a "normal" human breast epithelial line (MCF10A), which represents different stages of the carcinogenesis (47), Tang et al., (48) demonstrated that loss of the TβR-I/TβR-II signaling (or TGF-β response) did not cause transformation of the parent MCF10A cells but increased malignancy of a premalignant cell line MCF10AT1k and decreased metastatic efficiency of the malignant cell line MCF10ACalh. Interestingly, they also showed that there was an apparent inverse correlation between the expression of high molecular weight TGF-β receptors (including TβR-III and possibly TβR-V as determined by 125I-TGF-β affinity labeling) and progression of carcinogenesis represented by these cell lines, especially in early-stage cell lines which expressed TβR-I and TβR-II at levels comparable to those in the parent cell line, MCF10A.

The inventor hypothesizes that the loss of TβR-V/LRP may precede the loss of TβR-I or TβR-II during carcinogenesis. The inventor also hypothesizes that like in H1299 cells (human lung carcinoma cells), which express low levels of TβR-V/LRP, TGF-$β_1$ may be a mitogen or a growth factor for malignant breast cancer cells and loss of LRP/TβR-V or TβR-I/TβR-II may diminish the mitogenic or growth stimulatory response to TGF-$β_1$ and IGFBP-3 and thus metastatic efficiency. These hypotheses are supported by the observations: 1) Cancer cells have greatly decreased or undetectable expression of LRP in comparison with their normal counterparts (49-51). 2) Mv1Lu mutants R1B and DR26 cells, which express TβR-V and lack functional TβR-I and TβR-II, respectively, respond to IGFBP-3-induced growth inhibition and exhibit normal cell properties but do not respond to TGF-β-induced growth inhibition (at low concentrations) (14,24,40). 3) No normal cells have been found to lack LRP/TβPR-V as determined by $^{125}$I-TGF-$β_1$ (or $^{125}$I-IGFBP-3) affinity labeling and Western blot analysis (13,14,24). 4) Certain carcinoma cells lack LRP/TβR-V or express low levels of LRP/TβR-V but do express TβR-I and TβR-II (13,14,51). 5) Carcinoma cells (e.g., H1299 cells), which express low levels of LRP/TβR-V, exhibit mitogenic or growth stimulatory response to TGF-$β_1$ and IGFBP-3 rather than growth inhibition. Stable transfection of these cells (H1299 cells) with LRP cDNA restores the sensitivity to growth inhibition by TGF-$β_1$ and IGFBP-3.

Thus, accumulating evidence indicates that LRP/TβR-V expression inversely correlates with malignancy and invasiveness of carcinoma cells and other cancer cell types, supporting the importance of LRP/TβR-V in the tumor biology of carcinoma cells and possibly other cancer cells (13,50,51). On the other hand, LRP overexpression has been found in glioma and other cancer cells (52). These mesenchymal cell-derived cancer cells and their normal counterparts generally have a growth stimulatory response to IGFBP-3 and TGF-β. The association of increased expression of LRP with malignancy of these cancer cells is consistent with the notion that LRP can play a stimulatory or inhibitory role in determining the malignant behavior of different cancer cells (46). Together with angiogenesis factors (FGF-3 and VEGF), LRP and IGFBP-3 have recently been identified as a group of hypoxia-induced genes of tumor cells (53). The autocrine cell growth suppression mediated by LRP and IGFBP-3 and the angiogenesis stimulated by FGF-3 and VEGF may enable tumor cells to survive under hypoxic conditions. Investigations of the complex mechanisms by which LRP/TβR-V regulates cell growth promise to increase our understanding of tumor biology of carcinoma cells and possibly other cancer cell types.

EXAMPLE 2

Insulin Receptor Substrate (IRS) Proteins are Important for Cellular Growth Inhibition by IGFBP-3 and TGF-$\beta_1$.

Summary

Four lines of evidence are presented, which suggest that insulin receptor substrate proteins (IRS-1 and IRS-2) are important molecules for growth inhibition mediated by IGFBP-3 and TGF-$\beta_1$. The evidence includes: 1) Insulin and ($Q^3A^4Y^{15}L^{16}$) IGF-I block growth inhibition by either IGFBP-3 or TGF-$\beta_1$ (in the presence of a cyclic RGD peptide) in Mv1Lu cells. 2) IGFBP-3 induces serine-specific dephosphorylation of IRS-1 and IRS-2 in Mv1Lu cells and such dephosphorylation correlates with growth inhibition due to IGFBP-3 in Mv1Lu cells and mutant cells derived from the Mv1Lu cell line. 3) Both insulin and ($Q^3A^4Y^{15}L^{16}$) IGF-I block IGFBP-3-induced serine-specific dephosphorylation of IRS-2 in Mv1Lu cells. 4) Stable transfection of 32D myeloid cells (which lack endogenous IRS proteins and are insensitive to the growth inhibitory effects of IGFBP-3 and TGF-$\beta_1$) with IRS-1 or IRS-2 cDNA confers sensitivity to growth inhibition by both TGF-$\beta_1$ and IGFBP-3; this IRS-mediated growth inhibition can be completely or partially reversed by insulin in 32D cells stably expressing IRS-2 and the insulin receptor.

The finding that T$\beta$R-V/IGFBP-3 receptor is identical to LRP (supra) has unraveled a novel growth regulatory function of LRP. Understanding the growth inhibitory signaling cascade mediated by the LRP/T$\beta$R-V/IGFBP-3 receptor would help those skilled in the art, to which the invention is directed, to understand the molecular mechanisms by which TGF-$\beta$ and IGFBP-3 induce growth inhibition and how alteration of the LRP/T$\beta$R-V/IGFBP-3 receptor contributes to the malignant phenotype of human carcinoma cells. In this example, the inventor demonstrates that insulin receptor substrate proteins (IRSs) are important signaling molecules in the growth inhibitory response to IGFBP-3 and TGF-$\beta_1$.

Experimental Procedure-Materials

[$^{32}$P] Orthophosphate (500 mCi/ml) and [methyl-$^3$H] thymidine (67 Ci/mmole) were purchased from ICN Biochemicals (Irvine, Calif.). Molecular mass protein standards (myosin, 205 kDa, $\beta$-galactosidase, 116 kDa; phosphorylase b, 97 kDa; bovine serum albumin, 66 kDa; ovalbumin, 43 kDa; carbonic anhydrase, 29 kDa; $\beta$-lactoglobulin, 18 kDa), okadaic acid, E-64d, aFGF, FGFb, EGF, cantharidic acid, calyculin A, cyclosporin, chloramine T and Triton X-100 were obtained from Sigma (St. Louis, Mo.). Anti-IRS-1 IgG and anti-IRS-2 IgG and anti-phosphotyrosine IgG were obtained from Santa Cruz Biotech (Santa Cruz, Calif.). The proteasome inhibitor MG-132, mycrocystin-LW and calpain inhibitor II, were purchased from Calbiochem (La Jolla, Calif.). Protein A-sepharose was obtained from Pharmacia LKB Biotech (Piscataway, N.J.). $\beta_1{}^{25}$(41-65), a specific TGF-$\beta$ peptide antagonist, was prepared as described previously (85). ($A^3Q^4Y^{15}L^{16}$) IGF-I was provided by Dr. Margaret A. Cascieri, Merck Res. Labs, Rahway, N.J. Human TGF-$\beta_1$, IGFBP-1, IGFBP-1, IGF-I and TNF-$\alpha$ were purchased from Austral Biologicals (Santa Clara, Calif.) and R & D Systems (Minneapolis, Minn.). Human IGFBP-3 (expressed in *E. Coli*, M.W. ~35,000), anti-IRS-1 and anti-IRS-2 IgG were obtained from Upstate (Charlottesville, Va.). 32D cells expressing vector only and 32D/IRS-1 and 32D/IR/IRS-2 cells, which were stably transfected with human IRS-1 cDNA and the insulin receptor (IR)/IRS-2 cDNAs, respectively, were provided by Dr. Martin G. Myers, Joslin Diabetes Center, Harvard University. MB102-16 and MB102-9 cells were provided by Dr. Edward B. Loef, Mayo Clinic, Minnesota.

Experimental Procedure—$^{32}$P Metabolic labeling and Immunoprecipitation

Mv1Lu cells were grown in Dulbecco's modified Eagle medium (DMEM), changed to phosphophate-free DMEM medium containing 0.2% of dialyzed fetal calf serum for 1 hr and labeled with $^{32}$P-orthophosphate (200 µC/ml) for 2 hr. They were then treated with IGFBP-3 (1 µg/ml) for 2.5 hr and then with or without other growth factors [10 nM EGF, 10 nM aFGF, 10 nM bFGF, 10 nM TNF-$\alpha$, 10 nM insulin or 10 nM ($Q^3A^4Y^{15}L^{16}$) IGF-I] for a further 0.5 hr incubation. The cells were lysed in RIPA buffer and immunoprecipitated with anti-IRS-1 or anti-IRS-2 IgG. The immunoprecipitates were analyzed by 7.5% SDS-polyacrylamide gel electrophoresis (SDS-PAGE) under reducing conditions and autoradiography. The $^{32}$P-labeled IRS-1 or IRS-2 was excised from the dried gel and subjected to phosphoamino acid analysis as described previously (79).

Experimental Procedures—[methyl-3H] Thymidine Incorporation Assay

Mv1Lu cells were plated on 24-well clustered dishes and incubated with various concentrations of TGF-$\beta_1$ or IGFBP-3 in DMEM containing 0.1% fetal calf serum. After incubation at 37° C. for 18 hr, the cells were pulse-labeled with 1 µCi of [methyl-$^3$H]thymidine at 37° C. for 2 hr and the [methyl-$^3$H] thymidine incorporation into cellular DNA was determined as described previously (59). 32D cells were grown in RPMI 1640 medium containing 10% fetal bovine serum and 5% WEHI conditioned media according to the published procedure provided by Dr. Martin Myers, Harvard University. These cells were plated in 24-well clustered dishes at a cell density of ~$10^5$ cells/well and then treated with various concentrations of IGFBP-3 or TGF-$\beta_1$ with or without insulin (10 nM) in RPMI 1640 medium containing 0.1% fetal calf serum and 0.05% WEHI conditioned media. After incubation at 37° C. for 8 hr, the cells were pulse-labeled with 1 µCi of [methyl-$^3$H] thymidine. Following the 2-hr pulse, the cells were centrifuged to remove free [methyl-$^3$H] thymidine, washed with serum-free medium once, 1 ml of 10% trichloroacetic acid once, and 0.5 ml of ethanol:ether (2:1, v/v) once and dissolved in 0.2 M NaOH for scintillation counting. The assays were performed in quadruplicate.

Experimental Procedures—Determination of Tryosine Phosphorylation

Mv1Lu cells were plated on 30-mm dishes at a cell density of 4x$10^4$/cm$^2$ in DMEM containing 10% fetal calf serum. The cells in serum-free DMEM were pre-treated with IGFBP-3 (1 µg/ml) for 1 or 2 hr and then treated with insulin (10 nM) for 10 min or treated with insulin (10 nM) for 10 min and then treated with IGFBP-3 (1 µg/ml) for a further 2 hr, or treated simultaneously with insulin (10 nM) and IGFBP-3 (1 µg/ml) for 2 hr. The experiments were carried out at 37° C. The cell lysates were subjected to immunoprecipitation using anti- IRS-2 IgG followed by 7.5% SDS-PAGE and Western blot analysis using anti-phosphotryosine IgG and the ECL system (Santa Cruz).

Results

The following experiments show that insulin and IGF-I antagonize growth inhibition by IGFBP-3 and TGF-$\beta_1$.

IGFBP-3 inhibits cell growth in both IGF-dependent and IGF-independent manner (59,86-88). One mechanism involves inhibition of cell growth by scavenging IGFs from the IGF-I receptor; another, by directly interacting with the TβR-V/IGFBP-3 receptor. Mink lung epithelial cells (Mv1Lu cells) are a standard model cell system for studying TGF-$\beta_1$ and IGFBP-3-induced (IGF-independent) growth inhibition (59,65,80,81). They express the LRP/TβR-V/IGFBP-3 receptor which is required for TGF-$62_1$- and IGFBP-3-regulated growth inhibition and do not produce detectable endogenous IGFs, ruling out potential involvement of the IGF scavenging effect of IGFBP-3 in the system. To test the possibility that epithelial cell growth factors (insulin, IGF-I, aFGF, bFGF and EGF) may modulate the IGFBP-3-induced growth inhibition in Mv1Lu cells, the effects of these growth factors were examined on IGFBP-3- and TGF-$\beta_1$-induced growth inhibition in these epithelial cells. Among EGF, a FGF, and bFGF, insulin and ($Q^3A^4Y^{15}L^{16}$) IGF-I (an IGF-I analog which has a low affinity for IGFBP-3) (89), only insulin and ($Q^3A^4Y^{15}L^{16}$) IGF-I were capable of blocking IGFBP-3-regulated growth inhibition. As shown in FIG. 9, increasing concentrations of insulin quantitatively blocked the IGFBP-3-induced inhibition of DNA synthesis in Mv1Lu cells (FIG. 9A). However, it did not block TGF-$\beta_1$-induced inhibition of DNA synthesis in these cells (FIG. 9A). Insulin completely blocked IGFBP-3-induced inhibition with an $ED_{50}$ of ~1.0 nM (FIG. 9A). Like insulin, ($Q^3A^4Y^{15}L^{16}$) IGF-I completely blocked IGFBP-3-induced growth inhibition with an $ED_{50}$ of ~0.3 nM (FIG. 9B). These results suggest that insulin and ($Q^3A^4Y^{15}L^{16}$) IGF-I block IGFBP-3-induced growth inhibition through interaction with their cognate receptors. A 100-fold higher concentration (~100 nM) is known to be required for insulin to bind to the IGF-I receptor (74).

As demonstrated in the preceding example (supra), the TβR-V/IGFBP-3 receptor is required for IGFBP-3 and TGF-$\beta_1$-induced growth inhibition in responsive cells. Why insulin is incapable of blocking TGF-$\beta_1$-induced inhibition of DNA synthesis when it effectively blocks IGFBP-3-induced growth inhibition needs to be explained. Gagnon et al. (90) reported that the expression of extracellular matrix fibronectin induced by TGF-$\beta_1$ impairs insulin-induced signal transduction. Thus, the ability of insulin to block the TβR-V-mediated growth inhibitory response to TGF-$\beta_1$ may be impaired by the extracellular matrix expression induced by TGF-$\beta_1$ (which is mediated by the TβR-I/TβR-II heterocomplex). To test this possibility, the effect of insulin on TGF-$\beta_1$-regulated growth inhibition was determined by measuring DNA synthesis in the presence and absence of a cyclic RGD peptide (cyclo GRGDSPA) (91), which blocks the binding of extracellular matrix proteins (e.g., fibronectin) to integrins (91). As shown in FIG. 9C, TGF-$\beta_1$ (0.5 pM) inhibited ~75% of DNA synthesis in Mv1Lu cells. Neither insulin (10 nM) nor the cyclic RGD peptide (0.01 µg/ml) alone affected the TGF-$\beta_1$-induced inhibition of DNA synthesis. However, insulin was able to partially reverse the TGF-$\beta_1$-induced inhibition in the presence of a cyclic RGD peptide. The combination of insulin and the cyclic RGD peptide decreased the TGF-$\beta_1$-induced DNA synthesis inhibition from ~75% to ~39%. This suggests that insulin not only is capable of blocking IGFBP-3 growth inhibition, but also can block growth inhibition by TGF-$\beta_1$ under certain conditions, such as when a cyclic RGD peptide blocks binding of extracellular matrix proteins to integrins.

The following experiments show that IGFBP-3 induces specific dephosphorylation of IRS-1 or IRS-2 in Mv1Lu cells.

In view of the novel and surprising discovery made by the inventor that both insulin and ($Q^3A^4Y^{15}L^{16}$) IGF-I are capable of reversing IGFBP-3- and TGF-$\beta_1$-induced growth inhibition, the skilled artisan may reasonably expect that the signaling molecules shared by the insulin receptor and IGF-I receptor signaling cascades are involved in the reversal of IGFBP-3-induced growth inhibition by insulin or IGF-I. Because insulin receptor substrate proteins IRS-1 and IRS-2 are two major signaling and molecule-docking proteins shared by both the insulin receptor and IGF-I receptor signaling cascades (92,93), both appear to be the candidates for playing this role. To test this hypothesis, the effect of IGFBP-3 on the phosphorylation of IRS-1 or IRS-2 in Mv1Lu cells was examined. Mv1Lu cells were metabolically labeled with $^{32}$P-orthophosphate and then treated with or without IGFBP-3 (1 µg/ml) for 3 hrs. The $^{32}$P-labeled cell lysates were immunoprecipitated with antibodies to IRS-1 or IRS-2. The immunoprecipitates were analyzed by 7.5% SDS-PAGE under reducing conditions. As shown in FIGS. 10A and B, in Mv1Lu cells treated without IGFBP-3, IRS-1 and IRS-2 appeared as $^{32}$P-labeled bands with molecular masses of ~160 kDa and ~170 kDa, respectively, on SDS-PAGE (FIG. 10A, lane 1 and FIG. 10B, lane 1, respectively). Following treatment with IGFBP-3, the $^{32}$P-labeled IRS-1 and IRS-2 exhibited slightly increased electrophoretic mobility (FIG. 10A, lane 2 and FIG. 10B, lane 2, respectively). The $^{32}$P-phosphorylation of the IRS proteins in cells treated with and without IGFBP-3 appeared to occur at serine residues as determined by phosphoamino acid analysis (FIG. 10C). Since the IGFBP-3-induced increased mobility of $^{32}$P-labeled IRS-2 was more easily detected than that of $^{32}$P-labeled IRS-1, the inventor focused on the effect of IGFBP-3 on the phosphorylation status of IRS-2 in all subsequent experiments. It is understood that the skilled artisan would reasonably expect that the results observed for IRS-2 are equally applicable to IRS-1.

As shown in FIGS. 11A and B, IGFBP-3 induced increased electrophoretic mobility (on SDS-PAGE) of $^{32}$P-labeled IRS-2 in a time-and concentration-dependent manner. The electrophoretic mobility change of $^{32}$P-labeled IRS-2 occurred after a 0.5 hr incubation of cells with IGFBP-3. The half-optimal concentration ($ED_{50}$) for IGFBP-3 to induce this mobility change was estimated to be ~0.1 to 0.3 µg/ml. This $ED_{50}$ is very close to the Kd (6 nM) of IGFBP-3 binding to its receptor (TβR-V/IGFBP-3 receptor) in Mv1Lu cells (59). Since hypophosphorylated proteins migrate faster than hyperphosphorylated proteins on SDS-PAGE, and since proteins phosphorylated at certain serine residues migrate more slowly than proteins without such phosphorylation on SDS-PAGE (94,95), the IGFBP-3-induced increased electrophoretic mobility on SDS-PAGE of IRS proteins suggests that IGFBP-3 treatment of cells may lead to dephosphorylation of IRS proteins. To exclude the possibility that the faster-migrating $^{32}$P-labeled IRSs are proteolytic products, Mv1Lu cells were treated with MG-132 (a proteosome inhibitor), calpain inhibitor II, or E-64d (an irreversible thiol protease-specific inhibitor) for 1 hr prior to IGFBP-3 treatment and during IGFBP-3 treatment (for 14 hr). A protease inhibitor cocktail was also included in cell lysis and immunoprecipitation buffers. These proteolysis inhibitors did not affect the IGFBP-3-induced mobility change of $^{32}$P-labeled IRS-2 in Mv1Lu cells (96).

To prove that the electrophoretic mobility change of $^{32}$P-labeled IRS-2 is due to dephosphorylation induced by IGFBP-3, pulse and chase experiments were performed. Mv1Lu cells were pulse-labeled with $^{32}$P-orthophosphate for 2 hr and chased with unlabeled orthophosphate in the presence or absence of IGFBP-3 (1 µg/ml) for various time periods. At each time period, $^{32}$P-labeled IRS-2 was immunoprecipitated and analyzed by SDS-PAGE and autoradiography. As shown in 12A, the $^{32}$P-labeled IRS-2 exhibited increased electrophoretic mobility after 0.5 hr treatment of IGFBP-3 (lane 6 versus lane 5). In contrast, the $^{32}$P-labeled IRS-2 remained at the same position (lane 4 versus lane 1) even after a 1.5 hr incubation in cells treated without IGFBP-3. The radioactivity of $^{32}$P-labeled IRS-2 diminished with time during the chase period in cells treated with or without IGFBP-3, suggesting that the dephosphorylation (which does not alter the electrophoretic mobility of IRS-2) occurs in both IGFBP-3-dependent and independent manner. The mobility change of $^{32}$P-labeled IRS-2 suggests that IGFBP-3 induces specific dephosphorylation (at certain serine residues or sites, which results in increased electrophoretic mobility) of IRS-2 in Mv1Lu cells. This is referred to as specific dephosphorylation of IRS-2. This suggestion is supported by the observation that okadaic acid at 100 nM, a known phosphatase inhibitor (97), effectively blocked the IGFBP-3-induced specific dephosphorylation (with an electrophoretic mobility change of $^{32}$P-labeled IRS-2) but did not greatly affect the stimulated dephosphorylation (without an electrophoretic mobility change) of $^{32}$P-labeled IRS-2 in Mv1Lu cells (FIG. 12B, lane 8 versus lane 7). Other phosphatase inhibitors (cantharidic acid, microcystin, cyclosporin A, calyculin A and vanadale) (97) did not appear to affect the IGFBP-3-induced mobility change of $^{32}$P-labeled IRS-2 in Mv1Lu cells (data not shown).

To characterize the specificity of the IGFBP-3-induced specific dephosphorylation of $^{32}$P-labeled IRS-2, the effects on IRS-2 dephosphorylation of other IGFBPs (e.g., IGFBP-1 and IGFBP-2), which are known not to bind to the IGFBP-3 receptor (TβR-V) in Mv1Lu cells (81), were examined. Also examined were the effects of insulin, $(Q^3A^4Y^{15}L^{16})$ IGF-I and other growth factors and cytokines on IGFBP-3-induced specific dephosphorylation of $^{32}$P-labeled IRS-2 in these cells. As shown in FIG. 13A, IGFBP-1 and IGFBP-2 did not induce specific dephosphorylation (which resulted in electrophoretic electrophoretic mobility change) of $^{32}$P-labeled IRS-2 in these cells (lanes 3 and 4 versus lane 1), supporting the specificity of IGFBP-3-induced specific dephosphorylation (or electrophoretic mobility change) of $^{32}$P-labeled IRS-2. The IGFBP-3-induced specific dephosphorylation of $^{32}$P-labeled IRS-2 was blocked in the presence of $(Q^3A^4Y^{15}L^{16})$ IGF-I (FIG. 10B, lane 8 versus lane 7) and insulin (FIG. 10C, lane 6 versus lane 2) but not other growth factors/cytokines (EGF, bFGF, TGF-$β_1$, TNF-α) (FIGS. 13B and C). These results suggest that insulin and $(Q^3A^4Y^{15}L^{16})$ IGF-I are capable of blocking IGFBP-3-induced specific dephosphorylation of $^{32}$P-labeled IRS-2 in Mv1Lu cells. This appears to be analogous to the situation in which insulin and $(Q^3A^4Y^{15}L^{16})$ IGF-I are capable of blocking IGFBP-3-induced growth inhibition in these cells. The inability of TGF-$β_1$ to induce specific dephosphorylation of IRS-2 suggests that the molecular mechanism by which TGF-$β_1$ induces growth inhibition is different from that for IGFBP-3-induced growth inhibition (which is mainly mediated by the TβR-V/IGFBP-3 receptor). This is supported by the requirement that all three TGF-β receptor types (TβR-V/IGFBP-3 receptor, TβR-I and TβR-II) be present during cellular growth inhibition induced by TGF-$β_1$ (80).

The following experiments demonstrate that IGFBP-3 induces specific dephosphorylation of IRS-2 in Mv1Lu cell mutants and transfectants.

Mv1Lu cells are a standard model cell system for investigating growth inhibition by TGF-β and IGFBP-3 (70,71). It would be important to see the effect of IGFBP-3 on the phosphorylation status of IRS-2 in Mv1Lu mutants DR26 and R1B cells, which lack functional TβR-II and TβR-I, respectively. TGF-$β_1$ is ineffective in inhibiting growth of these mutant cells (98). By contrast, IGFBP-3 is a potent growth inhibitor in DR26 cells (59). It inhibits DNA synthesis more strongly in DR26 cells than in wild-type Mv1Lu cells and R1B cells. IGFBP-3 at 0.5 µg/ml exhibited ~80% inhibition of DNA synthesis in DR26 cells (FIG. 14A) whereas it inhibited 30-50% DNA synthesis in Mv1Lu (FIGS. 9A and 9B) and R1B cells (59). This potent inhibition of cell growth by IGFBP-3 in DR26 cells, as determined by measurement of DNA synthesis, was completely reversed in the presence of insulin (FIG. 14B). If IGFBP-3 inhibits cell growth by inducing specific dephosphorylation of IRS-2, one could predict that IGFBP-3 may induce specific dephosphorylation of IRS-2 more strongly in DR26 cells than in Mv1Lu cells and R1B cells. To test this possibility, the effect of IGFBP-3 on specific dephosphorylation of IRS-2 was examined in Mv1Lu, DR26 and R1B cells. As shown in FIG. 14C, IGFBP-3 indeed induced a greater increase in electrophoretic mobility in DR26 cells than in Mv1Lu and R1B cells.

By contrast, TGF-$β_1$ did not induce dephosphorylation of IRS-2 in DR26 cells up to 400 pM (FIG. 14D, lanes 8 and 9). In fact, TGF-$β_1$ alone was capable of stimulating $^{32}$P-labeled phosphorylation of IRS-2 in these cells (DR26 cells) lacking TβR-II (FIG. 14D, lanes 14, 5, 8, 10 versus lane 1). The phosphoamino acid analysis of $^{32}$P-labeled IRS-2 revealed that the TGF-$β_1$-stimulated phosphorylation occurred at serine residues (data not shown). Interestingly, IGFBP-3-induced dephosphorylation appeared to override TGF-$β_1$-induced phosphorylation of IRS-2 in these cells (FIG. 14D, lanes 4, 6, 7, 9 versus lanes 3, 5, 10, 8, respectively).

These results indicate that the IGFBP-3-induced specific dephosphorylation of IRS-2 correlates with IGFBP-3-induced growth inhibition in Mv1Lu cells and mutant cells (DR26 and R1B cells) derived from Mv1Lu cells. The results also suggest that the mechanism by which TGF-$β_1$ induces growth inhibition is different from that utilized by IGFBP-3. They further suggest that the TGF-$β_1$-stimulated serine-specific phosphorylation is mediated by the TβR-V/IGFBP-3 receptor in DR26 cells (which lack functional TβR-II but express the TβR-V/IGFBP-3 receptor).

Dore et al. (99) generated chimeric receptor constructs consisting of the extracellular domain of the granulocyte/macrophage colony-stimulating factor (GM-CSF) α or β receptor fused to the transmembrane and cytoplasmic domain of TβR-I or TβR-II and expressed them in Mv1Lu cells by stable transfection. They demonstrated that GM-CSF induces growth inhibition in Mv1Lu cells, which stably express the chimeric heterodimeric αIβII receptor, but not in Mv1Lu cells, which stably express the chimeric homodimeric αIβI receptor. In the control experiments, TGF-$β_1$ is capable of inducing growth inhibition in these cells. These results strongly support the importance of TβR-I/TβR-II heterocomplex formation in mediating signaling which leads to cellular responses. The effect of IGFBP-3 or GM-CSF on the phosphorylation status of IRS2 in Mv1Lu cells stably expressing αIβI (MB102-16 cells) or αIβII (MB102-9 cells) was examined. As shown in FIG. 14E, IGFBP-3 induced specific dephosphorylation (as demonstrated by an electrophoretic mobility change) of IRS-2 in both MB102-16 and MB102-9 cells (lane 4 versus lane 1 and lane 9 versus lane 6, respectively). However, GM-CSF only induced specific dephosphorylation (electrophoretic mobility change) of IRS-2 in MB102-9 cells, which expressed the chimeric heteromeric receptors ($\alpha I \beta II$) (lane 10 versus lane 6). GM-CSF appeared to induce moderate specific dephosphorylation (electrophoretic mobility change) of IRS-2 when compared with the IRS-2 specific dephosphorylation (electrophoretic mobility change) induced by IGFBP-3 in these cells (lane 10 versus lane 9). The mechanism by which GM-CSF induces specific dephosphorylation (electrophoretic mobility change) of IRS-2 is unknown. It is possible that GM-CSF may also induce the IRS-2-dephosphorylation (electrophoretic mobility change) by binding to the T$\beta$R-V/IGFBP-3 receptor which has a great potential for binding various ligands (80). These results are consistent with the notion that the specific dephosphorylation (at certain serine residues or sites) of IRS-2 is involved in the growth inhibitory response to IGFBP-3 and TGF-$\beta_1$.

The following experiments demonstrate that IGFBP-3 influences insulin-stimulated tyrosine phosphorylation of IRS-2.

Recently, Ricort and Binox, (100) reported that IGFBP-3 activated a tyrosine phosphatase capable of blocking the IGF-I signaling cascade (but not the insulin signaling cascade) in a cell-type-specific manner. This prompted the inventor to examine the effect of IGFBP-3 on insulin-stimulated tyrosine phosphorylation of IRS-2 in Mv1Lu cells. Mv1Lu cells were pre-stimulated with or without 10 nM insulin for 10 min and then treated with or without 1 µg/ml of IGFBP-3 for 1 hr. The $^{32}$P-labeled cell lysates were immunoprecipitated with anti-IRS-2 IgG. The immunoprecipitates were analyzed by 7.5% SDS-PAGE under reducing conditions and Western blot analysis using anti-phosphotyrosine IgG. As shown in FIG. 15A, IGFBP-3 treatment failed to affect the insulin-stimulated tyrosine phosphorylation of IRS-2 in Mv1Lu cells (lane 4 versus lane 14). This result appears to agree with their report that IGFBP-3 treatment does not affect insulin receptor-mediated signaling. However, the inventor was unable to detect the purported tyrosine phosphatase activity stimulated by IGFBP-3 in Mv1Lu cells using the methods of Ricort and Binox (100). One skilled in the art may hypothesize that IGFBP-3-induced specific dephosphorylation may affect the insulin-stimulated tyrosine phosphorylation of IRSs depending on the manner in which cells are exposed to IGFBP-3 and insulin. The IRS protein molecules contain many serine phosphorylation sites. The phosphorylation of some of these sites (positive sites) (in the presence of 0.1% fetal calf serum) may be required for tyrosine phosphorylation of IRSs or cell growth. The phosphorylation of the other sites (negative sites) (e.g., stimulated by TNF-$\alpha$) may confer resistance to tyrosine phosphorylation stimulated by insulin (101-105). The IGFBP-3-induced serine dephosphorylation may involve both types (positive and negative) of the serine phosphorylation sites.

Since serine and tyrosine phosphorylation/dephosphorylation of IRSs occurs dynamically in cells, the effects of pretreatment and simultaneous treatment with IGFBP-3 on insulin-stimulated tyrosine phosphorylation of IRS-2 were examined. In the experiment involving simultaneous treatment with IGFBP-3 and insulin, the cells were treated with IGFBP-3 (1 µg/ml) and insulin (10 nM) or with insulin (10 nM) alone at 37° C. for 2 hr. The tyrosine phosphorylation of IRS-2 in these cells was then determined by immunoprecipitation using anti-IRS-2 IgG followed by Western blot analysis using anti-phosphotyrosine IgG. As shown in FIG. 15B, pretreatment of Mv1Lu cells with IGFBP-3 for 2 hr diminished the tyrosine phosphorylation of IRS-2 stimulated by insulin (lane 1 versus lane 2), whereas simultaneous treatment of these cells with insulin and IGFBP-3 resulted in enhancement of insulin-stimulated tyrosine phosphorylation of IRS-2 when compared with cells stimulated with insulin alone (lane 3 versus lane 4). These results appear to be similar to those obtained in the $^{32}$P-metabolic labeling experiments. Although insulin still retarded the electrophoretic mobility of IRS-2 after IGFBP-3 pretreatment of Mv1Lu cells, the pretreatment of these cells with IGFBP-3 decreased the $^{32}$P-labeling of IRS-2 stimulated by insulin (FIG. 13C, lane 6 versus lane 5). The results support the notion that the effect (negative or positive) of IGFBP-3 on tyrosine phosphorylation of IRS-2 is dependent on how cells are exposed to insulin and IGFBP-3. They are also compatible with the observation that insulin reversed IGFBP-3 growth inhibition of Mv1Lu cells, which was assayed after cells were treated with insulin and IGFBP-3 for 18 hr.

The following experiments demonstrate that IRS proteins are important for TGF-$\beta_1$ and IGFBP-3-mediated growth inhibition.

As described above, insulin and ($Q^3A^4Y^{15}L^{16}$) IGF-I, but not other growth factors and cytokines, block either the IGFBP-3-induced growth inhibition or IGFBP-3-induced specific dephosphorylation of IRS proteins. This suggests that IRS proteins may be involved in insulin-or IGF-I-induced reversal of growth inhibition by IGFBP-3. The inability of TGF-$\beta_1$ to induce dephosphorylation of IRS-2 implies some complexity of the mechanism of TGF-$\beta_1$ growth inhibition. Since insulin is capable of partially blocking TGF-$\beta_1$-induced growth inhibition in the presence of a cyclic RGD peptide, the inventor hypothesized that IRS proteins are also involved. To test this hypothesis, the inventor examined the effects of IGFBP-3 and TGF-$\beta_1$ on cell growth (as determined by measurement of DNA synthesis) of 32D cells stably transfected with IRS cDNAs, insulin receptor cDNA, or vector only. 32D cells are murine myeloid cells, which do not express endogenous IRS proteins (106). They express very low levels of the insulin receptor and high levels of the T$\beta$R-V/IGFBP-3 receptor (106,107). In addition, wild type 32D cells do not exhibit a growth inhibitory response to IGFBP-3. They respond weakly to growth inhibition by TGF-$\beta$ but have a functional T$\beta$R-I/T$\beta$R-II heterocomplex-mediated signaling as determined by measurement of TGF-$\beta_1$-induced transcriptional activation of plasminogen activator inhibitor-1 (data not shown). For these reasons, the 32D cell system should be appropriate for defining the roles of IRS proteins in TGF-$\beta_1$ and IGFBP-3 growth inhibition. As shown in FIG. 16, IGFBP-3 and TGF-$\beta_1$ inhibited DNA synthesis of 32D cells transfected with vector only minimally or not at all (FIGS. 16A and B). However, 32D cells expressing either IRS-1 or IRS-2 exhibited a potent growth inhibitory response to TGF-$\beta_1$ and IGFBP-3 (FIGS. 16A and B). Importantly, insulin was capable of blocking IGFBP-3-induced growth inhibition and of partially reversing TGF-$\beta_1$-induced growth inhibition (FIGS. 16C and D). These results are very similar to those obtained using Mv1Lu cells as an assay cell system (FIGS. 9A and 9C) and suggest that IRS proteins are important for TGF-$\beta_1$- and IGFBP-3-induced growth inhibition.

Discussion

TGF-$\beta$ and IGFBP-3 both have growth regulatory activity. TGF-$\beta$ has been implicated in many pathophysiological processes including carcinogenesis (108). IGFBP-3 is the most abundant IGFBP in the circulation (109-111). It has been implicated as a mediator of the actions of TGF-β, retinoic acid, and the tumor suppressor gene p53. It may contribute to the malignancy of certain human cancers (111-113). Many carcinoma cells lack or express little of the LRP/TβR-V/IGFBP-3 receptor. The growth of these cells, unlike their normal counterparts, is not inhibited by TGF-$β_1$ and IGFBP-3 (59,107). These observations suggest that the LRP/TβR-V/IGFBP-3 receptor is required for TGF-$β_1$ and IGFBP-3 growth inhibition and may play a role in the malignant phenotype of these carcinoma cells. It was disclosed herein that the LRP/TβR-V/IGFBP-3 receptor is identical to low-density lipoprotein receptor-related protein (LRP). This unexpected discovery has disclosed a novel growth regulatory function of LRP. Moreover, this finding has provided clues for defining the molecular mechanisms by which TGF-$β_1$ and IGFBP-3 induce growth inhibition.

In this example, it was demonstrated that insulin and ($Q^3A^4Y^{15}L^{16}$) IGF-I block IGFBP-3-induced growth inhibition and partially reverse TGF-$β_1$-induced growth inhibition in the presence of a cyclic RGD peptide in Mv1Lu cells. These results imply that the insulin receptor and IGF-I receptor signaling pathways cross-talk with the LRP/TβR-V/IGFBP-3 receptor signaling, TβR-I/TβR-II signaling pathways and possibly others such as the integrin signaling pathway (90). Several lines of evidence presented herein indicate that IRS proteins are important for TGF-$β_1$ and IGFBP-3 growth inhibition. These include: 1) Insulin and ($Q^3A^4Y^{15}L^{16}$) IGF-I, but not EGF, aFGF and bFGF, block IGFBP-3-induced growth inhibition and partially reverse TGF-$β_1$-mediated growth inhibition in the presence of a cyclic RGD peptide in Mv1Lu cells. 2) IGFBP-3 induced a specific dephosphorylation of IRS-2 in Mv1Lu cells. Such dephosphorylation appears to correlate with the IGFBP-3-induced growth inhibition in Mv1Lu cells and their mutant cells. 14) Insulin and IGF-I, but not other growth factors, block the IGFBP-3-induced specific dephosphorylation of IRSs in Mv1Lu cells. 4) TGF-$β_1$ and IGFBP-3 induce DNA synthesis inhibition of 32D cells expressing either IRS-1 or IRS-2 but not 32D cells stably expressing vector control. 5) Insulin blocks IGFBP-3-induced DNA synthesis inhibition in 32D cells expressing IRS-2 and the insulin receptor and partially reverses TGF-$β_1$ inhibition of DNA synthesis in these cells.

Tyrosine phosphorylation of IRS proteins, which serve as on/off switches to recruit and regulate various down-stream signaling proteins in PI3-kinase and MAP-kinase pathways, has been studied extensively (92). On the other hand, the biochemical functions of serine phosphorylation are not well defined but have recently been implicated in attenuating the abilities of IRS proteins to be phosphorylated on tyrosine and in impairment of insulin-mediated signaling (101-105). Several serine residues involved have been identified (105,114, 115). However, the role of the serine-specific phosphorylation of IRS proteins in cell growth (in the presence of 0.1% fetal calf serum) is unknown. It is herein demonstrated that IGFBP-3 induces specific dephosphorylation on serine residues of IRS proteins, which may contribute to IGFBP-3-induced growth inhibition. This raises the possibility that serine phosphorylation of IRSs, which is sensitive to IGFBP-3, is involved in signaling leading to cell growth (in the presence of 0.1% fetal calf serum). IGFBP-3 appears to induce specific dephosphorylation of IRSs by activating an okadaic acid-sensitive phosphatase via interaction with the LRP/TβR-V/IGFBP-3 receptor. By contrast, TGF-$β_1$ induces serine-specific phosphorylation of IRSs, suggesting that the molecular mechanism by which TGF-$β_1$ induces growth inhibition is different from that utilized by IGFBP-3.

Based on the unexpected results described herein, and in considering some of the teachings known in the art at the time of this discovery (59,60,64,65,90,92,93,116), the inventor proposes a simplified model for the insulin/($A^4Q^5Y^{15}L^{16}$) IGF-I blocking of growth inhibition by IGFBP-3 and TGF-β and cross talk of the TβR-I/TβR-II, TβR-V (or TβR-V/TβR-I), insulin receptor, IGF-I receptor, integrin and c-Met signaling cascades (FIG. 17). In this model, IGFBP-3 induces specific dephosphorylation of IRS-1 and IRS-2 via interaction with the TβR-V/IGFBP-3 receptor. This leads to growth inhibition. Insulin and ($A^4Q^5Y^{15}L^{16}$) IGF-I antagonize the IGFBP-3-induced growth inhibition by stimulating tyrosine-specific phosphorylation of IRS proteins through interaction with their cognate receptors; which overrides the serine-specific dephosphorylation induced by IGFBP-3.

By contrast, TGF-β stimulates serine-specific phosphorylation of IRS proteins, presumably via interaction with the TβR-V/TβR-I heterocomplex (as demonstrated in DR26 cells which lack functional TβR-II) (116). This, in concert with the TβR-I/TβR-II heterocomplex/Smad2/3/4 signaling cascade, leads to growth inhibition. The integrin signaling cascade initiated by extracellular matrix protein (e.g., fibronectin and collagen) expression induced by TGF-β impairs the ability of insulin to block TGF-β-stimulated TβR-V/TβR-I-mediated signaling cascade by down-regulating insulin-stimulated tyrosine phosphorylation of IRS proteins (90). This impairment can be partially reversed by blocking the interaction of extracellular matrix proteins with their receptors (integrins) with a cyclic RGD peptide (cyclo GRGSDPA). The c-Met signaling cascade induced by c-Met ligand hepatocyte growth factor (HGF) blocks the TβR-V and TβR-I/TβR-II-mediated growth inhibitory signaling at the sites of cell cycle regulation (60,96). The finding of cross talk (via IRS proteins) between the insulin signaling and TβR-V-mediated growth inhibitory signaling cascade has practical clinical implications. Insulin or insulin signaling defects may up-regulate the TGF-β activity generated in wounds, resulting in the attenuation of wound re-epithelialization and healing, which is a common clinical problem observed particularly often in diabetic patients.

EXAMPLE 3

Overexpression of LRP-1 minireceptors containing individual domains (mLRP-I, mLRP-II, mLRP-III and mLRP-IV) diminishes the growth inhibitory response to TGF-$β_1$ in CHO-K1 cells.

To further define the role of LRP-1 in the growth inhibitory response to TGF-β1 in CHO-K1 cells, we determined the effect of overexpression of LRP minireceptors containing individual domains. We hypothesized that LRP-1 not only binds TGF-β1 but also mediates signaling leading to the growth inhibitory response to TGF-β1 (in concert with other TGF-P receptor types). If this hypothesis is correct, the LRP-1 minireceptors containing individual domains have potential to function as dominant negative mutants if they are overexpressed in cells. To test this hypothesis, CHO-K1 cells were stably transfected with HA-tagged LRP-1 minireceptors I, II, III and IV cDNAs and vector only. The clones selected were named CHO-K1/mLRP-I, CHO-K1/mLRP-II, CHO-K1/mLRP-III and CHO-K1/mLRP-IV, respectively. These cells expressed the products of these LRP minireceptors cDNA constructs with molecular masses of the heavy chain (ligand binding domain); 120 kDa, ~160-kDa, ~200 kDa and ~160 kDa for mLRP-I, mLRPIT, mLRP-Ill and mLRP-IV.

The expression levels for these minireceptors were comparable based on the Western blot analysis using antiserum to HA. It was observed that overexpression of these LRP-1 minireceptors all diminished the growth inhibitory response (as determined by measurement of DNA synthesis) to TGF-β1 in CHO-K1 cells. By contrast, CHO-K1 cells stably transfected with vector only still responded to growth inhibition as untransfected CHO-K1 cells did. These LRP-1 minireceptors did not have detectable ability to mediate growth inhibition by TGF-β1. It was observed that overexpression of mLRP-IV did not alter the mitogenic response to TGF-β in CHO-LRP-1⁻ (LRP "minus") cells. Similar results were also obtained in CHO-LRP-1⁻ cells stably expressing mLRP-I, II and III. These results suggest these LRP-1 minireceptors are capable of functioning as dominant negative mutants for endogenous LRP activity.

It was observed that the overexpression of LRP minireceptors does not affect expression of endogenous LRP-1 and TGF-β1-induced PA1-expression. The finding that different LRP minireceptors containing individual domains all affect the growth inhibitory response to TGF-β1 was unexpected. Although the binding site(s) for TGF-β1 in the LRP-1 molecule has not been identified, while not wishing to be bound by theory, it is possible but unlikely that all of these minireceptors are capable of binding TGF-β1 and compete with endogenous LRP-1 for binding TGF-β1. To define the molecular basis of the dominant negative function of these LRP minireceptors, we examined the expression of endogenous LRP-1 in these CHO-K1 cells expressing these LRP minireceptors, using Western blot analysis, $^{125}$I-α$_2$M* binding analysis and $^{125}$I-IGFBP-3 affinity labeling. It was observed that all of these cells expressed comparable levels of endogenous LRP-1. It is of importance to note that in addition to endogenous LRP-1, mLRP-II and mLRP-IV in cells stably expressing these minireceptors addition to exhibited 1z5I-IGFBP-3 binding as determined by Iz5I-IGFBP-3 affinity labeling. The molecular size of the lii3-mLRP-II or lii3-mLRP-IV complex was estimated to be ~160 kDa. TGF-β1-induced transcriptional activation of PAI-I was also functional in these cells.

EXAMPLE 4

Identification and Characterization of the Acidic pH Binding Sites for Growth Regulatory Ligands of Low Density Lipoprotein Receptor-related Protein-1.

Summary

The type V TGF-β receptor (TβR-V) plays an important role in growth inhibition by TGF-β in responsive cells. Unexpectedly, the TβR-V was found (supra) to be identical to LRP-1/α2M receptor; this has disclosed novel growth regulatory functions of LRP-1. Here we demonstrate that, in addition to expressing LRP-1, all cells examined exhibit low-affinity but high-density acidic pH binding sites for LRP-1 growth regulatory ligands (TGF-β1 and α2M*). These sites, like LRP-1, are sensitive to receptor-associated protein and calcium depletion but, unlike LRP-1, are also sensitive to chondroitin sulfate and heparin sulfate and capable of binding ligands which do not bind to LRP-1. Annexin VI has been identified as a major membrane-associated protein capable of binding α2M* at acidic pH. This is evidenced by structural and Western blot analyses of the protein purified from bovine liver plasma membranes by α2M*-affinity column chromatography at acidic pH. Cell surface annexin VI is involved in 125I-TGF-β1 and 125I-α2M* binding to the acidic pH binding sites and 125I-α2M* binding to LRP-1 at neutral pH as demonstrated by the sensitivity of cells to treatment with anti-annexin VI IgG. Cell surface annexin VI is also capable of mediating internalization and degradation of cell surface-bound 125I-TGF-β1 and 125I-α2M* at acidic pH and of forming ternary complexes with 125I-α2M* and LRP-1 at neutral pH as demonstrated by co-immunoprecipitation. Trifluoperazine and fluphenazine, which inhibit ligand binding to the acidic pH binding sites, block degradation after internalization of cell surface-bound 125I-TGF-β1 or 125I-α2M*. These results suggest that the acidic pH binding sites are novel in their acidic pH optimum and high density, and that cell surface annexin VI may function as an acidic pH binding site or receptor and may also function as a co-receptor with LRP-1 at neutral pH.

Experimental Procedures

Materials—Na125I (17.4 Ci/mg), Zn2+ chelate-Sepharose FF and Sephacryl S-300 HR were purchased from Amersham Pharmacia Biotech (UK). TGF-β1 was obtained from Austral Biologicals (San Ramon, Calif.) and R & D Systems, Inc. (Minneapolis, Minn.). Human IGFBP-3 (expressed in *E. coli*, M.W. ⓜ35,000) was obtained from Upstate (Charlottesville, Va.). Molecular mass protein standards (myosin, 205 kDa; β-galactosidase, 116 kDa; phosphorylase b, 97 kDa; bovine serum albumin, 66 kDa; ovalbumin, 43 kDa; carbonic anhydrase, 29 kDa; β-lactoglobulin, 18 kDa), chloramine T, Triton X-100, BAPTA [ethylenedioxybis (o-phenylenenitrilo) tetra acetic acid], EGTA (tetrasodium salt), EDTA (disodium salt), Pseudomonas exotoxin A, human transferrin, human low density lipoprotein (LDL), bovine lactoferrin, human apoE, trifluoperazine, fluphenazine, promethazine, W-5, W-7, verapamil, monodansylcadaverine, and bovine serum albumin (BSA) were purchased from Sigma Chemical Co. (St. Louis, Mo.). GST-RAP (a fusion protein of glutathione S-transferase and receptor-associated protein) was expressed in *E. coli* using pGEX-KG-RAP (6.4 kb) plasmid and purified according to the procedure of Herz et al. J. Biol Chem 266: 21232-21238 (1991). Anti-annexin VI IgG and control IgG were obtained from BioDesign (Saco, Me.) and Santa Cruz (Santa Cruz, Calif.). Protein A-Sepharose and activated Sepharose 4B were obtained from Pharmacia CKB Biotech (Piscataway, N.J.). α$_2$M*-Sepharose 4B was prepared according to the protocol of the activated Sepharose 4B manufacturer. Mink lung epithelial cells (Mv1Lu), mouse embryonic fibroblasts (MEF cells), homozygous LRP-1-deficient mouse embryonic fibroblasts (PEA-13 cells) (Willnow and Hertz, J. Cell Sci 107:719-727) and human hepatocarcinoma cells (HepG2 and H3B cells) were grown and maintained in Dulbeccos modified Eagles medium (DMEM) containing 10% fetal calf serum (FCS).

Preparation of Human α2M and α2M*—Human α2M was purified from pooled citrate-treated human plasma using Zn2+ chelate-Sepharose FF affinity chromatography followed by gel-filtration on Sephacryl S-300 HR as described previously (Salvesen, G. and Enghild, J. J. (1993) Meth. Enzymol. 223, 121-141; Kurecki, T., et al. (1979) Anal. Biochem. 99, 415-420). α2M activated by methylamine (α2M*) was prepared as described previously (Huang, S. S., et al. (1988) J. Biol. Chem. 263, 1535-1541; Liu, Y., et al. (2000) Nature Med. 6, 1380-1387).

Iodination of IGFBP-3, TGF-β1 and α2M*—IGFBP-3 or TGF-β1 (5 ⓜg) was iodinated with 2 mCi Na125I using chloramine T according to the procedure of Leal et al. (1997, J. Biol. Chem. 272, 20572-20576; 1999, J. Biol. Chem. 274, 6711-6717) and O'Grady et al. (1991, J. Biol. Chem. 266, 8583-8589), respectively. The specific radioactivities of 125I-labeled IGFBP-3 (125I-IGFBP-3) and 125I-labeled TGF-β1 (125I-TGF-β1), were 1-4×10⁵ cpm/ng and 1-5×10⁵ cpm/ng, respectively. Iodination of α2M* (100 μg) was done as described previously (23-25). The specific radioactivity of 125I-labeled α2M* (125I-α2M*) was 2×10⁴ cpm/ng. 125I-TGF-β1 or 125I-α2M* was mixed with unlabeled TGF-β1 or α2M* to yield a specific radioactivity of 2-5×10³ cpm/ng in some experiments.

Specific binding of 125I-IGFBP-3, 125I-TGF-β1 and 125I-α2M* to cells—Mv1Lu, MEF and PEA-13 cells were plated at a cell density of 8×10⁴ cells/well in 48-well clustered dishes and grown at 37° C. overnight in DMEM/50 mM HEPES, pH 7.4 containing 10% fetal calf serum (FCS). The cells were then washed and incubated with 6 nM 125I-IGFBP-3, 1 nM 125I-TGF-β1 or 10 nM 125I-α2M* in the presence and absence of EGTA tetrasodium salt or BAPTA (5 mM), GST-RAP (15 μg/ml) or 200-fold excess of unlabeled TGF-β1 or α2M* in DMEM/50 mM HEPES/acetate at pH 4.0, 5.0, 6.0, 7.4 (or 7.0) and 8.0, all containing BSA (1 mg/ml). GST-RAP or 200-fold excess of unlabeled TGF-β1 or α2M* was used to estimate non-specific binding. After 2.5 hr at 0° C., the specific binding of 125I-IGFBP-3, 125I-TGF-β1 or 125I-α2M* was determined. BAPTA and the tetrasodium salt (but not the free acid form) of EGTA appeared to function well as chelators of Ca2+ at acidic pH (Bers, D. M., et al., Meth. Cell Biol. 40, 3-29, 1994). The experiments were performed in quadruplicate.

Internalization and degradation of cell surface-bound (specific binding) 125I-TGF-β1 or 125I-α2M* - Cells (8×10⁴ cells/well) in 48-well clustered dishes were incubated with 125I-TGF-β1 (100 pM) or 125I-α2M* (2 nM) with or without 10 μM trifluoperazine, fluphenazine or promethazine in the presence and absence of 200-fold excess of unlabeled TGF-β1 or α2M* (to estimate non-specific binding) in DMEM/25 mM HEPES, pH 7.4 containing BSA (1 mg/ml). After 2 hr at 0° C, the cells were washed and incubated with DMEM/25 mM HEPES, pH 7.4 containing BSA (1 mg/ml) with or without 10 μM trifluoperazine, fluphenazine or promethazine. After 1 hr at 37° C., the medium was collected and precipitated with 10% trichloroacetic acid (TCA). The TCA-soluble radioactive material in the medium represented the cellular degradation products of 125I-TGF-β1 or 125I-α2M*. The cells were then treated with trypsin (5 mg/ml), maintained for 20 min at 0° C. and centrifuged. The radioactivity in the supernate and cell pellets represented cell surface-bound and internalized 125I-TGF-β1 or 125I-α2M*, respectively. The experiments were performed in quadruplicate.

Immunoprecipitation of cell surface-bound 125I-α2M*— MEF and PEA-13 cells (1×10⁵ cells/well) grown in 24-well clustered dishes were incubated with 1 nM 125I-α2M* in the presence and absence of 200-fold excess of unlabeled α2M* in DMEM/25 mM HEPES, pH 7.4 containing BSA (1 mg/ml). After 2 hr at 0° C., the cells were lysed with 50 mM HEPES/HCl buffer containing 0.1% Triton X-100, 0.15 M NaCl and 2 mM Ca2+ and the cell lysates were immunoprecipitated with anti-annexin VI IgG or control IgG in the same HEPES/HCl buffer. The immunoprecipitates were analyzed by 7.5% SDS-polyacrylamide gel electrophoresis (SDS-PAGE) under reducing conditions. 125I-α2M* appeared as a 180-kDa (monomer) band on the autoradiogram.

Cell surface localization of annexin VI—Cells grown on coverslips in DMEM/25 mM HEPES, pH 7.4 containing 10% FCS were fixed with 3.7% formaldehyde in DMEM/25 mM HEPES, pH 7.4 (ice cold). After 1 hr, the fixed cells were washed with DMEM/25 mM HEPES, pH 7.4 (ice cold). The coverslips were then blocked with BSA (5 mg/ml) in DMEM/ 25 mM HEPES, pH 7.4 on ice overnight. After washing with DMEM/25 mM HEPES, pH 7.4, the fixed cells were treated with anti-annexin VI IgG or control IgG (1:75 dilution) in DMEM/25 mM HEPES, pH 7.4 containing BSA (5 mg/ml) at room temperature for 2 hr. After washing, fixed cells were incubated with anti-rabbit IgG-FITC conjugate (1:50 dilution) at room temperature for 1.5 hr and then washed twice with ice cold phosphate buffered saline prior to visualization with a confocal fluorescent microscope.

Affinity column chromatography on α2M*-Sepharose 4B—Bovine liver plasma membranes were subjected to Triton X-100 extraction according to the published procedures of O'Grady, et al., (1991) J. Biol. Chem. 266, 8583-8589, except that 50 mM HEPES/acetate buffer, pH 6 (or pH 5), containing 0.15 M NaCl and 4 mM CaCl2 was used. The Triton X-100 extracts were applied onto a column of α2M*-Sepharose 4B (1.6×20 cm) in 50 mM HEPES/acetate buffer, pH 6.0 (or pH 5.0), 0.15 M NaCl, and 0.1% Triton X-100 (HEPES/acetate buffer) containing 4 mM Ca2+. After washing with HEPES/acetate buffer containing 4 mM CaCl2 extensively, the column was eluted with 10 mM EDTA in HEPES/acetate buffer. The fractional volume of the eluents was 1 ml. An aliquot of fractions (EDTA eluents) was subjected to 7.5% SDS-PAGE under non-reducing and reducing conditions and silver staining. The concentrated flow-through fractions and peak fraction were analyzed by Western blot analysis using anti-annexin VI IgG.

MALDI-TOF analysis—A 68-kDa protein purified from α2M*-Sepharose 4B affinity column chromatography was subjected to 7.5% SDS-PAGE under reducing conditions, stained with Coomassie blue and digested with trypsin. MALDI-TOF analysis of the tryptic digests was carried out at Applied Biosystems, CA.

Effect of anti-annexin VI IgG treatment of cells on specific binding of 125I-TGF-β1 or 125I-α2M*—Mv1Lu, MEF and PEA-13 cells (8×10⁴ cells/well) grown, on 48-well clustered dishes were treated with various concentrations (0, 7.5, 15 and 30 μg/ml) of anti-annexin VI IgG or control IgG in DMEM/25 mM HEPES/acetate buffer at pH 6.4 or 7.4 containing BSA (1 mg/ml) at 37° C. for 2 hr. The treated cells were then kept on ice and additional anti-annexin VI IgG or control IgG in the same DMEM/HEPES/acetate buffer was added to wells (0, 7.5, 15 and 30 μg/ml). The binding assay at pH 6.4 or 7.4 (at 0° C.) was started by adding 125I-TGF-β1 (100 pM) or 125I-α2M* (1 nM) with or without 200-fold excess of unlabeled TGF-β1 or α2M* (to estimate non-specific binding) to wells. After 2 hr at 0° C, the cell-associated 125I-TGF-β1 or 125I-α2M* was determined. The specific binding of 125I-TGF-β1 or 125I-α2M* was estimated by subtracting non-specific binding from total binding. The experiments were performed in duplicate.

Results

LRP-1 ligands exhibit high capacity binding to cells at acidic pH.—Ca²⁺ is known to be required for the ligand binding activity of LRP-1 (9,10,13). The finding that the TβR-V/IGFBP-3 receptor is identical to LRP-1 prompted us to investigate the effect of EGTA (tetrasodium salt) on $^{125}$I-labeled IGFBP-3 ($^{125}$I-IGFBP-3) binding to mink lung epithelial cells (Mv1Lu cells). Mv1Lu cells were incubated with 6 nM $^{125}$I-IGFBP-3 with or without 200-fold excess of unlabeled IGFBP-3 in the presence or absence of 5 mM EGTA (tetrasodium salt) at varying pH (pH 4, 5, 6, 7 and 8). After 2.5 hr at 0EC, the specific binding of $^{125}$I-IGFBP-3 was determined. As shown in FIG. 1A, $^{125}$I-IGFBP-3 bound to Mv1Lu cells in a pH-dependent manner. Interestingly, the EGTA-sensitive $^{125}$I-IGFBP-3 binding (estimated by subtracting $^{125}$I-IGFBP-3 binding in the presence of 5 mM EGTA from total binding) was optimal at pH 5. This was unexpected and led us to investigate whether binding of TGF-$\beta_1$ and $\alpha_2$M*, which are other ligands for LRP-1, was also optimal at acidic pH. Mv1Lu cells were incubated with 1 nM $^{125}$I-labeled TGF-$\beta_1$ ($^{125}$I-TGF-$\beta_1$) or 10 nM $^{125}$I-labeled $\alpha$2M* ($^{125}$I-$\alpha_2$M*) in the presence or absence of GST-RAP (15 μg/ml), EGTA or BAPTA (5 mM), or 200-fold excess of unlabeled TGF-$\beta_1$ or $\alpha_2$M* at pH 4, 5, 6 and 7.4. GST-RAP is a fusion protein of glutathione-S-transferase and receptor-associated protein (RAP) which inhibits binding of all known ligands to LRP-1. The tetrasodium salt (but not the free acid form) of EGTA and BAPTA function well as chelators of $Ca^{2+}$ at acidic pH (26). It was observed that $^{125}$I-TGF-$\beta_1$ or $^{125}$I-$\alpha_2$M* bound to Mv1Lu cells in a pH-dependent manner. Both the EGTA- or BAPTA-sensitive and GST-RAP-sensitive binding of both $^{125}$I-TGF-$\beta_1$ and $^{125}$I-$\alpha_2$M* were maximal at pH 5. The pH 7.4 (high-affinity) binding of $^{125}$I-TGF-$\beta_1$ and $^{125}$I-$\alpha_2$M* were less as compared with their binding at pH 5 in these cells. The Kds for binding of $^{125}$I-TGF-$\beta_1$ and $^{125}$I-$\alpha_2$M* (high affinity) to LRP-1/TβR-V at pH 7.4 are known to be ~50-400 and ~75 pM, respectively. These results suggest that Mv1Lu cells may possess low-affinity, high-density binding sites for $^{125}$I-IGFBP-3, $^{125}$I-TGF-$\beta_1$ and $^{125}$I-$\alpha_2$M* with acidic pH optima. This suggestion is supported by Scatchard plot analysis of 125I-$\alpha_2$M* binding to Mv1Lu cells at pH 5. It was observed that $^{125}$I-$\alpha_2$M* bound to Mv1Lu cells in a concentration-dependent manner with a saturating concentration of ~120 nM. Scatchard plot analysis of the binding data revealed a single class of low-affinity binding sites with an apparent Kd of ~51 nM and ~1×10$^6$ sites/cell.

Since binding of LRP-1 ligands ($^{125}$I-IGFBP-3, $^{125}$I-TGF-$\beta_1$ and $^{125}$I-$\alpha_2$M*) requires the presence of $Ca^{2+}$, has an acidic pH optimum, and is sensitive to GST-RAP, we suspected that LRP-1 itself might mediate binding. This has not previously been described but, to exclude this possibility, we performed $^{125}$I-TGF-$\beta_1$ or $^{125}$I-$\alpha_2$M* binding at a varying pH using mouse embryonic fibroblasts (MEF) and LRP-1-deficient mouse embryonic fibroblasts (PEA-13 cells). We observed that binding in both MEF and PEA-13 cells was maximal at pH 5, suggesting that such binding is mediated by a protein(s) other than LRP-1.

The acidic pH binding has broad ligand specificity—To characterize the specificity of the acidic pH binding of $^{125}$I-$\alpha_2$M*, we determined the effects of various concentrations of unlabeled $\alpha_2$M* and native $\alpha_2$M on $^{125}$I-$\alpha_2$M* binding at pH 5.5 in MEF cells. $\alpha_2$M* is known to bind to LRP-1 at neutral pH with higher affinity as compared with native a$_2$M. We observed that the IC$_{50S}$ of unlabeled $\alpha_2$M* and native $\alpha_2$M were estimated to be ~50 nM and ~150 nM, respectively, at acidic pH (pH 5.5). The IC$_{50}$ of unlabeled $\alpha_2$M* appeared to be similar to the Kd of $^{125}$I-$\alpha_2$M* binding to Mv1Lu, MEF and PEA-13 cells at pH 5 as determined by Scatchard plot analysis. It is possible that the relatively low IC$_{50}$ of native $\alpha_2$M (compared with that of $\alpha_2$M*) might be due to endogenous LRP-1 in these cells. To test this possibility, we determined the effects of various concentrations of unlabeled $\alpha_2$M* and native $\alpha_2$M on $^{125}$I-$\alpha_2$M* binding to PEA-13 cells which are known to be deficient in LRP-1. We observed that unlabeled $\alpha_2$M* and native $\alpha_2$M exhibited IC$_{50S}$ of ~120 nM and >400 nM, respectively. This suggests that in PEA-13 cells, the absence of LRP-1 may decrease the ability of native $\alpha_2$M or $\alpha_2$M* to bind to the acidic pH binding sites. Alternatively, LRP-1 may collaborate with the acidic pH binding sites for ligand interactions at acidic pH.

The ligands of endocytic receptors such as transferrin, lactoferrin (a LRP-1 ligand) and LDL have also been shown to exhibit acidic pH binding in various cell types, but they have not been well characterized. To determine whether the acidic pH binding site(s) for $\alpha_2$M* is also responsible for binding of transferrin, lactoferrin (an LRP ligand) and apoE, we first examined the effects of these proteins on $^{125}$I-$\alpha_2$M* binding to Mv1Lu cells, MEF cells and PEA-13 cells. Cells were incubated with 2 nM $^{125}$I-$\alpha_2$M* in the presence and absence of 10 μM of transferrin, lactoferrin or apoE at pH 5.5 or pH 7.4 (for comparison). After 2.5 hr at 0° C., the specific binding of $^{125}$I-$\alpha_2$M* to cells was determined. At 10 μM, all of these proteins completely blocked the specific binding (at pH 5.5) of $^{125}$I-$\alpha_2$M* in Mv1Lu, MEF and PEA-13 cells (data not shown). In contrast, these proteins did not have a significant effect on $^{125}$I-$\alpha_2$M* binding (at pH 7.4) to Mv1Lu and MEF cells, which is mediated by LRP-1 (data not shown). Lactoferrin and $\alpha_2$M* bind to distinct sites of LRP-1 and do not compete with each other for binding to LRP-1. These results suggest that transferrin, lactoferrin and apoE may bind to the same acidic pH binding sites as $\alpha_2$M* does. Alternatively, the acidic pH binding sites for these molecules may be different but overlapping. To further define the ligand specificity of the acidic pH binding sites, the effects of various concentrations of transferrin, lactoferrin, γ-globulin, Pseudomonas exotoxin A (a ligand of LRP-1) or LDL on $^{125}$I-$\alpha_2$M* binding (at pH 5 or 6) to Mv1Lu cells were determined. We observed that increasing concentrations of lactoferrin, transferrin and LDL correspondingly inhibited $^{125}$I-$\alpha_2$M* binding to cells with IC$_{50S}$ of ~0.05 μM, ~0.5 μM and ~5 μg/ml (pH 6), respectively. In contrast, γ-globulin and Pseudomonas exotoxin at 0.5 μM did not effectively inhibit $^{125}$I-$\alpha_2$M* binding to cells (data not shown). These results indicate that the acidic binding sites are capable of binding ligands which do not bind to LRP-1.

Cell surface annexin VI is involved in the acidic pH binding of $^{125}$I-TGF-$\beta_1$ and $^{125}$I-$\alpha_2$M*. The acidic pH binding sites may play a role in the process of ligand endocytosis and degradation. They may be co-internalized with LRP-1/$\alpha_2$M receptor (which is mainly responsible for neutral pH binding). They may also be present in endosomes where it functions as an intracellular cargo transporter which has ligand binding activity with an optimum acidic pH and targets ligands for lysosomal degradation. To identify the protein(s) responsible for mediating the acidic pH binding, we decided to purify this protein(s) from Triton X-100 extracts of bovine plasma membranes by $\alpha_2$M*-Sepharose affinity column chromatography at pH 6 or 5. Bovine liver plasma membranes were used as the starting material because they are rich in endocytic receptors such as LRP-1. If these acidic binding sites have collaborative interactions with the endocytic receptors in vivo, they should be abundant in tissues (e.g., liver) and cells which are rich in endocytic receptors. The Triton X-100 extracts (pH 6 or 5) containing 4 mM $CaCl_2$ of bovine liver plasma membranes were subjected to $\alpha_2$M*-Sepharose 4B affinity column chromatography at pH 6 (or pH 5). After extensive washing with HEPES/acetate buffer at pH 6 (or pH 5) containing 0.1% Triton X-100 and 4 mM $CaCl_2$, the column was eluted with HEPES/acetate buffer at pH 6 (or pH 5) containing 10 mM EDTA and 0.1% Triton X-100 and the eluted fractions analyzed by silver blue staining. We observed that a ~68 kDa protein was found in the EDTA eluent fractions (from pH 6 affinity column chromatography), as demonstrated by 7.5% SDS-PAGE under non-reducing conditions and silver staining. MALDI-TOF analysis of the tryptic digests of this ~68-kDa protein revealed that the protein was bovine annexin VI (data not shown). Western blot analysis of the 68-kDa protein also supported the conclusion that it was annexin VI. Under the experimental conditions (affinity column chromatography at pH 6), a very small amount of LRP-1 was found in the EDTA eluent fractions. The heavy chain (M.W. ~515 kDa) of LRP-1 was detected by 5% SDS-PAGE, followed by Western blot analysis (data not shown). However, annexin VI appeared to be the major protein in the EDTA eluents of $\alpha_2 M^*$-Sepharose 4B affinity column chromatography at pH 6 or pH 5 (data not shown). As reported previously (Strickland, D. K., et al. (1990) J. Biol. Chem. 265, 17401-17404), LRP-1 was identified as the major protein in the EDTA eluents of $\alpha_2 M^*$-Sepharose affinity colums chromatography at pH 7.4.

Annexin VI has recently been shown to be a putative cell surface receptor for chondroitin sulfate (Takagi, H. A., et al. (2002) J. Cell Sci. 115, 3309-3318). It was also reported to be capable of binding heparin sulfate (Gerke, V., and Moss, S. E. (2002) Physiol. Rev. 82, 331-371; Ishitsuka, R., et al.. (1998) J. Biol. Chem. 273, 9935-9941). We, therefore, examined the effects of chondroitin sulfate and heparin sulfate on $^{125}$I-$\alpha_2 M^*$ binding to Mv1Lu cells at pH 5. As shown in FIG. 6A, chondroitin sulfate A, B and C were potent inhibitors of $^{125}$I-$\alpha_2 M^*$ binding to these cells at pH 5. Interestingly, chondroitin sulfate B and C were more potent than chondroitin sulfate A in inhibiting $^{125}$I-$\alpha_2 M^*$ binding to the cells. In contrast, heparin sulfate at 1 µg/ml enhanced $^{125}$I-$\alpha_2 M^*$ binding to Mv1Lu cells by ~400%. At 10 µg/ml, heparin sulfate inhibited $^{125}$I-$\alpha_2 M^*$ binding to these cells by >80%. Since annexin VI is known to bind chondroitin sulfate and heparin sulfate, these results are consistent with the contention that cell surface annexin VI is involved in the acidic pH binding of $^{125}$I-$\alpha_2 M^*$. At 10 µg/ml, chondroitin sulfate A, B and C and heparin sulfate did not significantly affect $^{125}$I-$\alpha_2 M^*$ binding to LRP-1 at neutral pH in Mv1Lu cells (data not shown).

To determine whether cell surface annexin VI is necessary for the acidic pH binding of LRP-1 ligands, we examined the effect of anti-annexin VI IgG treatment at pH 6.4 and 7.4 (for subsequent binding assays at pH 6.4 and 7.4, respectively) on $^{125}$I-TGF-$\beta_1$ binding to Mv1Lu cells or $^{125}$I-$\alpha_2 M^*$ binding to MEF and PEA-13 cells. Cells were treated with various concentrations of anti-annexin VI IgG or control IgG at pH 6.4 and 7.4 at 37EC for 2 hr. The specific binding (at pH 6.4 and 7.4) of $^{125}$I-TGF-$\beta_1$ or $^{125}$I-$\alpha_2 M^*$ was then determined. We observed that increasing concentrations of anti-annexin VI IgG quantitatively blocked $^{125}$I-TGF-$\beta_1$ binding at pH 6.4 in Mv1Lu cells, $^{125}$I-$\alpha_2 M^*$ binding at pH 6.4 in Mv1Lu, MEF and PEA-13 cells and $^{125}$I-$\alpha_2 M^*$ binding at pH 7.4 in Mv1Lu and MEF cells. Anti-annexin VI IgG at 25 µg/ml blocked binding of $^{125}$I-TGF-$\beta_1$ to Mv1Lu cells by ~50% and at 30 µg/ml completely blocked $^{125}$I-$\alpha_2 M^*$ binding at pH 6.4 in Mv1Lu, MEF and PEA-13 cells, respectively. Anti-annexin VI IgG (30 µg/ml) also blocked 50-60% of $^{125}$I-$\alpha_2 M^*$ binding to Mv1Lu and MEF cells at pH 7.4; this was mainly mediated by LRP-1. Anti-annexin VI IgG (30 µg/ml) exhibited only a slight inhibitory effect (~15%) on $^{125}$I-TGF-$\beta_1$ binding to Mv1Lu cells at pH 7.4; while not wishing to be bound by theory, we presume this is due to the fact that $^{125}$I-TGF-$\beta_1$ binding at pH 7.4 is mainly mediated by TGF-$\beta$ type I, II and III receptors in Mv1Lu cells. In PEA-13 cells, which are deficient in LRP-1, anti-annexin VI IgG also completely inhibited $^{125}$I-$\alpha_2 M^*$ binding to cells at pH 6.4. These results indicate that treatment of cells with anti-annexin VI IgG is capable of blocking $^{125}$I-TGF-$\beta_1$ binding to the acidic pH binding sites (annexin VI) and also capable of inhibiting $^{125}$I-$\alpha_2 M^*$ binding to either the acidic binding site (annexin VI) or LRP-1 (at pH 7.4). These results also suggest that cell surface annexin VI is involved in the acidic pH binding of $^{125}$I-TGF-$\beta_1$ and $^{125}$I-$\alpha_2 M^*$ and in the neutral pH binding (to LRP-1) of $^{125}$I-$\alpha_2 M^*$. The inhibition of $^{125}$I-$\alpha_2 M^*$ binding (at neutral pH) to LRP-1 by treatment of cells with anti-annexin VI IgG suggests that cell surface annexin VI may associate with LRP-1 and function as a co-receptor with LRP-1 at neutral pH. Alternatively, annexin VI may be located very close to LRP-1 at the cell surface. The cell surface localization of annexin VI was also shown by immunofluorescent staining of annexin VI at the cell surface of Mv1Lu, MEF, PEA-13 and Hep3B cells. Annexin VI has also been localized at the cell surface of other cell types (Takagi, H. A., et al. (2002) J. Cell Sci. 115, 3309-3318; Gerke, V., and Moss, S. E. (2002) Physiol. Rev. 82, 331-371). To test the above possibilities, we performed co-immunoprecipitation of cell surface-bound $^{125}$I-$\alpha_2 M^*$ (at pH 7.4) in MEF cells and PEA-13 cells using anti-annexin VI IgG. We observed that anti-annexin VI IgG was capable of co-immunoprecipitating $^{125}$I-$\alpha_2 M^*$ (~40% of LRP-1-bound $^{125}$I-$\alpha_2 M^*$) in MEF cells but not in PEA-13 cells. Since MEF and PEA-13 cells express comparable levels of annexin VI as determined by Western blot analysis (data not shown), this result indicates that LRP-1-bound $^{125}$I-$\alpha_2 M^*$ in MEF cells can be co-immunoprecipitated by anti-annexin VI IgG. It also suggests that cell surface annexin VI may form ternary complexes with $^{125}$-$\alpha_2 M^*$ and LRP-1 and function as a co-receptor of LRP-1.

Cell surface annexin VI is involved in mediating ligand binding, internalization and degradation at acidic pH—Because PEA-13 cells are deficient in LRP-1 (supra) and the density of acidic pH binding sites in PEA-13 cells is as great as in wild-type MEF cells, they should be a good system for testing whether cell surface annexin VI is capable of mediating ligand (e.g., $\alpha_2 M^*$) binding and internalization/degradation at acidic pH. PEA-13 and MEF cells were incubated with $^{125}$I-$\alpha_2 M^*$ at pH 6 or 7.4 (for MEF cells only) at 0° C. for 2.5 hr. PEA-13 cells did not exhibit specific binding of $^{125}$I-$\alpha_2 M^*$ at pH 7.4. This is consistent with the fact that they are deficient in LRP-1. These cells were then washed and warmed to 37° C. After 1 hr at 37° C., the cell surface-bound, internalized and degraded (TCA soluble) $^{125}$I-$\alpha_2 M^*$ were determined. We observed that MEF and PEA-13 cells were able to internalize and degrade $^{125}$I-$\alpha_2 M^*$ bound to the cell surface (~70%) at pH 6.0. This cell surface binding (specific binding), internalization and degradation of $^{125}$I-$\alpha_2 M^*$ could be blocked by preincubation of cells with anti-annexin VI IgG. At pH 7.4, more than 90% of cell surface bound $^{125}$I-$\alpha_2 M^*$, which was mediated by LRP-1, underwent internalization and degradation in MEF cells after an incubation time of 1 hr. These results suggest that although it is less efficient than LRP-1 (which mediates internalization and degradation of $^{125}$I-$\alpha_2 M^*$ at pH 7.4), cell surface annexin VI is capable of mediating internalization and degradation of $^{125}$I-$\alpha_2 M^*$ at pH 6.

Specific inhibitors block acidic pH ligand binding—Fluphenazine was previously shown to be an annexin VI binding compound as demonstrated by affinity column chromatography (Moore, P. B. (1986) Biochem. J. 238, 49-54). Since fluphenazine and other phenothiazine-related compounds, which are weak bases, are capable of entering cells and accumulating at high concentration in intracellular acidic compartments (e.g., endosomes), it seemed possible that fluphenazine and similar compounds (e.g., trifluoperazine) may affect LRP ligand binding to annexin VI in the lumen of endosomes and prelysosomal compartments. To test this possibility, we examined the effects of several weak bases including trifluoperazine, fluphenazine, monodansylcadaverine (a transglutaminase inhibitor), promethazine (a phenothazine compound), W-5 (a weak calmodulin antagonist), W-7 (a potent calmodulin antagonist) and verapamil (a calcium channel blocker) on $^{125}$I-$\alpha_2$M* binding to MEF cells and PEA-13 cells at pH 5.5 and pH 7.4. Among these compounds, trifluoperazine and fluphenazine were found to be the most potent inhibitors of $^{125}$I-$\alpha_2$M* binding to MEF cells at pH 5.5. Monodansylcadaverine and W-7 were less effective inhibitors. Promethazine, whose structure is homologous to trifluoperazine and fluphenazine, was not effective in blocking $^{125}$I-$\alpha_2$M* binding to cells at pH 5.5. Verapamil and W-5 (100 μM) were inactive in blocking $^{125}$I-$\alpha_2$M* binding to cells at pH 5.5. Trifluoperazine and fluphenazine inhibited $^{125}$I-$\alpha_2$M* binding in a concentration-dependent manner with IC50S of ~65-75 μM at pH 5.5. Trifluoperazine and fluphenazine also appeared to be effective in inhibiting $^{125}$I-$\alpha_2$M* binding to LRP-1 at pH 7.4. The IC$_{50S}$ of the trifluoperazine and fluphenazine were estimated to be ~25-30 μM. Interestingly, promethazine was almost as effective as trifluoperazine and fluphenazine for inhibiting $^{125}$I-$\alpha_2$M* binding (at pH 7.4) to MEF cells. These results suggest that trifluoperazine and fluphenazine are capable of blocking binding of LRP ligands (e.g., $\alpha_2$M*) to the acidic pH binding sites or annexin VI and may be useful agents for defining the biological functions of the acidic pH binding site—or annexin VI-mediated binding in intracellular (endosomal) trafficking and degradation of LRP ligands.

To determine the effect of trifluoperazine on $^{125}$I-TGF-$\beta_1$ binding to the acidic pH binding sites, Mv1Lu cells were incubated with 100 pM $^{125}$I-TGF-$\beta$ in the presence of various concentrations of trifluoperazine. After 2.5 hr at 0° C., the specific binding of $^{125}$I-TGF-$\beta_1$ was determined. We observed that trifluoperazine inhibited the specific binding at pH 5 of $^{125}$I-TGF-$\beta$ in a concentration-dependent manner with an IC$_{50}$ of ~150 μM. This result suggests that trifluoperazine also blocks $^{125}$I-TGF-$\beta_1$ binding to the acidic pH binding sites (e.g., annexin VI) effectively.

Trifluoperazine and fluphenazine inhibit cellular degradation of $^{125}$I-TGF-$\beta_1$ and $^{125}$I-$\alpha_2$M* in Mv1Lu and MEF cells—Annexin VI has been implicated in the transport of LDL from early endosomes to later endosomes or prelysosomal compartments after internalization of LDL (Grewal, T., et al. (2000) *J. Biol. Chem.* 275, 33806-33813). We hypothesized that cell surface annexin VI (as an LRP-1 co-receptor or a component in the LRP-1 complex) and LRP-1-ligand complexes are co-internalized and enter early endosomes which have an acidic luminal pH, facilitating the strong interaction between annexin VI and LRP-1 ligands (e.g., $\alpha_2$M*) and the dissociation of LRP-1 ligands from the LRP-1 complexes. Moreover, annexin VI, which is internalized or is already present in endosomes, may function as a cargo transporter which carries the cargo (ligand) from early endosomes to late endosomes or the prelysosomal compartment. In the prelysosomal compartment (in which the Ca$^{2+}$ concentration is low), the cargo (LRP-1 ligands or other proteins) is unloaded from the annexin VI complex and then targeted to lysosomes for degradation. While not wishing to be bound by theory, if this hypothesis is correct, trifluoperazine and fluphenazine, which are weak bases (like acridine orange) capable of entering cells and accumulating in the lumen of acidic endosomes (concentration >100-fold that in medium), should be able to block degradation of LRP-1 ligands by impairing their movement from early endosomes to late endosomes. We therefore examined the effect of 10 μM trifluoperazine, fluphenazine or promethazine on the internalization and degradation of cell surface-bound (specific binding) $^{125}$I-TGF-$\beta_1$ or $^{125}$I-$\alpha_2$M* in Mv1Lu cells. At this concentration, these compounds had no effect on $^{125}$I-TGF-$\beta_1$ or $^{125}$I-$\alpha_2$M* binding (at pH 7.4) to cells. Cells were incubated with $^{125}$I-TGF-$\beta_1$ (100 pM) or $^{125}$I-$\alpha_2$M* (2 nM) in DMEM (pH 7.4) in the presence or absence of 200-fold molar excess of unlabeled TGF-$\beta_1$ or $\alpha_2$M* (for estimating non-specific binding) with or without 10 μM trifluoperazine, fluphenazine or promethazine at 0° C. After 2.5 hr, cells were washed, then warmed to 37° C. After incubation at 37° C. for 1 hr in DMEM (pH 7.4) in the presence or absence of 10 μM trifluoperazine, fluphenazine or promethazine, the cell surface-bound, internalized and degraded $^{125}$I-TGF-$\beta_1$ or $^{125}$I-$\alpha_2$M* were determined. We observed that trifluoperazine at 10 μM completely blocked the degradation and correspondingly increased the amount of internalized $^{125}$I-TGF-$\beta_1$ or $^{125}$I-$\alpha_2$M* without altering the amount of cell surface-bound $^{125}$I-TGF-$\beta_1$ or $^{125}$I-$\alpha_2$M* in Mv1Lu cells. Like trifluoperazine, fluphenazine (10 μM) also completely inhibited the degradation of cell surface-bound $^{125}$I-TGF-$\beta_1$ or $^{125}$I-$\alpha_2$M* in these cells (data not shown). By contrast, promethazine (10 μM) did not exhibit any significant effect on the degradation and internalization of cell surface-bound $^{125}$I-TGF-$\beta_1$ or $^{125}$I-$\alpha_2$M* (data not shown). In PEA-13 cells, which are LRP-1-deficient mouse embryonic fibroblasts and used as a negative control, no internalization, degradation or even cell surface binding of $^{125}$I-$\alpha_2$M* was observed when experiments were carried out under the same conditions (at pH 7.4). Wild-type mouse embryonic fibroblasts (MEF cells) exhibited trifluoperazine-inhibitable degradation of cell surface-bound $^{125}$I-$a_2$M* or $^{125}$I-TGF-$\beta_1$ as Mv1Lu cells did (data not shown). These results support the hypothesis that annexin VI is involved in the intracellular trafficking events leading to lysosomal degradation.

Discussion

The acidic pH binding sites have been demonstrated in many cell types using different ligands, including IGFBP-3, vascular endothelial cell growth factor, transferrin, ApoE, and many others. However, they have not been well characterized. Here we demonstrate that LRP ligands IGFBP-3, TGF-$\beta_1$ and $\alpha_2$M* exhibit high-capacity and low-affinity acidic pH binding in MEF, PEA-13 and Mv1Lu cells. Unlike LRP-1, the acidic pH binding sites are sensitive to heparin sulfate and chondroitin sulfate. We also provide evidence to suggest that cell surface annexin VI is involved in the acidic pH binding of LRP-1 ligands (e.g., IGFBP-3, TGF-$\beta_1$ and $\alpha_2$M*) and other proteins. The evidence includes 1) annexin VI is a major protein identified in Triton X-100 extracts of bovine liver plasma membranes, which binds to the $\alpha_2$M*-Sepharose affinity column at acidic pH (pH 6 and 5) in a Ca$^{2+}$-dependent manner. 2) Annexin VI is known to bind Ca$^{2+}$, heparin sulfate and chondroitin sulfate. The acidic pH binding of $^{125}$I-TGF-$\beta_1$ or $^{125}$I-$\alpha_2$M* is sensitive to calcium depletion, heparin sulfate and chondroitin sulfate. 3) The acidic pH binding of $^{125}$I-TGF-$\beta_1$ in Mv1Lu cells or $^{125}$I-$\alpha_2$M* in MEF, PEA-13 and Mv1Lu cells can be blocked by preincubation of cells with anti-annexin VI IgG but not control IgG. 4) The acidic pH binding of $^{125}$I-$\alpha_2$M* is effectively blocked by lactoferrin as well as non-LRP-1 ligands such as transferrin, but not γ-globulin and Pseudomonas exotoxin (an LRP-1 ligand), and 5) A431 cells (a human endometrial carcinoma cell line), which do not express annexin VI (57), do not exhibit anti-annexin VI IgG-sensitive acidic pH binding of $^{125}$I-$\alpha_2$M* (unpublished results).

Annexin VI is a member of a family of structurally homologous Ca$^{2+}$-dependent phospholipid-binding proteins. It is enriched in rat liver endosomes, localized in the apical endosomes in rat hepatocytes and colocalized with Igp120, a prelysosomal marker in normal rat kidney cells. It has been implicated in the budding of clathrin-coated pits from plasma membranes and is involved in the trafficking of low density lipoprotein from endosomes to the prelysosomal compartment. It has also been shown to be able to form $Ca^{2+}$ channels and insert into membranes at acidic pH or in the presence of a 4 mM concentration of GTP. Although annexin VI (like other types of annexins) lacks a signal sequence for secretion, it has been identified extracellularly where it can act as a receptor for chondroitin sulfate. The cell surface location of annexin VI may be due to its ability to insert into phospholipid bilayers. Here, using immunofluorescent staining, we demonstrate that annexin VI is localized at the cell surface of MEF, PEA-13 and Mv1Lu cells and other cell types. We also show that pretreatment of cells with anti-annexin VI IgG partially or completely blocks $^{125}$I-TGF-$\beta_1$ binding to cells at pH 6.4 or $^{125}$I-$\alpha_2$M* binding to cells at pH 6.4 and pH 7.4. Since LRP-1 is known to be responsible for $\alpha_2$M* binding at pH 7.4, these results suggest that cell surface annexin VI may function as a receptor (at acidic pH) and a co-receptor (at pH 7.4) for LRP-1 ligands (e.g., $\alpha_2$M*). This suggestion is supported by several observations: 1) The complete inhibition of $^{125}$I-$\alpha_2$M* binding to the acidic pH binding sites by treatment of cells with anti-annexin VI IgG in Mv1Lu, MEF and PEA-13 cells indicates that cell surface annexin VI mediates the acidic pH binding of $^{125}$I-$\alpha_2$M*. 2) Cell surface annexin VI is involved in mediating ligand binding, internalization and degradation at acidic pH. 3) The partial inhibition of $^{125}$I-$\alpha_2$M* binding (at pH 7.4) to LRP-1 by treatment of cells with anti-annexin VI IgG suggests that cell surface annexin VI may function as a co-receptor for only a fraction of LRP-1 on the cell surface. This suggestion is supported by the observation that ~40% of LRP-1-bound $^{125}$I-$\alpha_2$M* was immunoprecipitated by anti-annexin VI IgG. 4) Cellular heparan sulfate and chondroitin sulfate are known in the art to be co-receptors for certain LRP-1 ligands. Removal of heparan sulfate or chondroitin sulfate from cells by enzymic digestion appears to diminish the ability of the cells to internalize and degrade these LRP-1 ligands. Since annexin VI has been shown to bind heparin sulfate and chondroitin sulfate at the cell surface, we hypothesize that the heparan sulfate or chondroitin sulfate complex of cell surface annexin VI may serve as a co-receptor for these LRP-1 ligands. 5) The corresponding expression, as determined by Western blot analysis of both LRP-1 and annexin VI, occurs in all cell types examined. For example, fibroblasts (MEF and NIH 3T3 cells) exhibit 3-5 fold higher amounts of both LRP-1 and annexin VI than epithelial cells (mink lung epithelial cells). Carcinoma cells (e.g., A431 and HCT116 cells) that lack or express very low levels of LRP-1 also produce no or very little annexin VI. Both annexin VI and LRP-1/T$\beta$R-V have been hypothesized to be candidates for tumor suppression gene products. 6) Cell surface annexin VI forms ternary complexes with $^{125}$I-$\alpha_2$M* and LRP-1, as shown by co-immunoprecipitation (at pH 7.4) of annexin VI and $^{125}$I-$\alpha_2$M* in MEF cells but not in PEA-13 cells. 7) $\alpha_2$M* has been shown to regulate N-methyl-D-aspartate receptor-mediated calcium influx in primary culture neurons. Since annexin VI and other annexin family members are known to form calcium channels in membranes, they (as co-receptors) may play a role in depletion of calcium ions from endosomes (possibly resulting in calcium influx) during endocytosis and in endosomal trafficking of ligands and their receptors. The calcium concentrations in extracellular compartments and late endosomes are in the range of ~mM and ~$\mu$M, respectively. Depletion of calcium and acidification of endosomes are required for endosomal trafficking of internalized ligands and receptors, and 8) Co-receptors (Grp 78 and midkine) for LRP-1 have recently been reported. However, we have no evidence to indicate the presence of either co-receptor in Mv1Lu and MEF cells.

The ligand binding activity of the acidic pH binding sites or cell surface annexin VI may play a role in tumor biology. Cumulative acquisition of genetic alteration via activation of proto-oncogenes to oncogenes and loss of tumor suppressor genes selects tumor cell clones with either proliferation or survival potential. The increase of nutrient and oxygen consumption in tumor cells leads to a microenvironment in tumors characterized by low oxygen and glucose levels and acidic pH. The acidic microenvironment within solid tumors may contribute to changes in cellular physiology and responses of tumor cells. We hypothesize that the acidic pH binding sites or cell surface annexin VI in tumor cells may potentially functionally (partially) substitute for the receptors (e.g., LRP-1, transferrin receptor and LDL receptor, which have optimal activity at the physiological neutral pH) under such acidic conditions. Although the acidic pH binding sites or cell surface annexin VI is less efficient than LRP-1 (at pH 7.4) in mediating ligand internalization and degradation, its high density in cells may enable it to function as a significant receptor (at acidic pH) comparable to LRP-1 or other receptors at pH 7.4 (Table II). If this hypothesis is correct, annexin VI should be important in animal pathophysiology. However, annexin VI null mutant mice have been shown to exhibit normal phenotypes, suggesting that other annexin family members or other unidentified proteins may also be involved in the acidic pH ligand binding activity of cells. This possibility is supported by the observation that A431 cells, which lack annexin VI, exhibit anti-annexin VI IgG-insensitive acidic pH ligand ($\alpha_2$M*) binding and internalization activity.

Trifluoperazine and fluphenazine, which are weak bases and have calmodulin antagonist activity, have been used as antipsychotic drugs. Their antipsychotic actions are believed to be mediated by their activity as dopamine receptor antagonists. Trifluoperazine was shown to reversably deplete ~50% of cell surface $\alpha_2$M* receptors at 30 $\mu$M (DiPaola, M., et al. (1984) *J. Cell. Physiol.* 118, 193-202). Thioridazine, a phenothiazine derivative, was reported to inhibit cellular degradation of $^{125}$I-labeled EGF (Kuratomi, Y., et al. (1986) *Exp. Cell Res.* 162, 436-448). The mechanisms by which these phenothiazine derivatives affect these cellular processes are unknown. However, the potential involvement of the weak base properties (raising the pH of endocytic vesicles or lysosomes) and calmodulin antagonist activity of these compounds at the concentrations generally used in these effects has been ruled out. Here we demonstrate that trifluoperazine and fluphenazine are effective inhibitors of $^{125}$I-$\alpha_2$M* binding to the acidic pH binding sites (e.g., annexin VI) and to LRP-1 (at pH 7.4) with IC$_{50S}$ of ~65-75 and ~25-30 $\mu$M, respectively. Since weak base compounds (e.g., acridine orange) are capable of entering cells and accumulating in the intracellular acidic compartments such as endosomes at a few-hundred fold higher concentration than that in medium, the acidic pH ligand binding inhibitory activity of trifluoperazine and fluphenazine may be pharmacologically significant. In our studies, treatment of cells with 10 $\mu$M trifluoperazine or fluphenazine completely inhibits cellular degradation of cell surface-bound $^{125}$I-TGF-$\beta_1$ or $^{125}$I-$\alpha_2$M* following internalization. At 10 $\mu$M in the medium, trifluoperazine or fluphenazine, a weak base, should be able to accumulate in the lumen of endosomes at concentrations that are effective in inhibiting $^{125}$I-TGF-$\beta_1$- or $^{125}$I-$\alpha_2$M*-annexin VI (or acidic pH binding site) complex formation in endosomes and subsequent lysosomal targeting. Promethazine, which shares weak base properties with trifluoperazine and fluphenazine, appears to be ineffective in blocking cellular degradation of $^{125}$I-TGF-$\beta_1$ or $^{125}$I-$\alpha_2$M* under the same experimental conditions, suggesting that the inhibition of the $^{125}$I-TGF-$\beta_1$ or $^{125}$I-$\alpha_2$M* degradation by trifluoperazine or fluphenazine is specific and is likely due to its newly identified annexin VI or acidic pH ligand binding inhibitory activity.

Endosomal signaling is known in the art to play a pivotal role in several ligand receptor-mediated signaling cascade systems. Inhibition of lysosomal targeting for degradation of ligands should logically enhance or prolong endosomal signaling mediated by the ligand receptor complex. Trifluoperazine or related compounds may be useful agents for enhancing pharmacological actions of ligands, which are sensitive to these compounds and utilize endosomal signaling.

What is claimed is:

1. A method of inhibiting cell proliferation comprising (a) contacting a cell with a receptor ligand wherein the receptor ligand is a TGF-β or an IGFBP-3 wherein the receptor ligand engages an LRP that is expressed at the surface of the cell, and (b) contacting the cell with an IRS protein such that the IRS protein is administered to the cell and the IRS protein undergoes a change in phosphorylation status, wherein said change in phosphorylation status results in the inhibition of cell proliferation.

2. The method of claim 1 wherein the receptor ligand is TGF-β.

3. The method of claim 1 wherein the receptor ligand is IGFBP-3.

4. The method of claim 1 wherein the cell is a cancer cell.

5. The method of claim 1 wherein the cell is in a patient.

* * * * *

SEQUENCE LISTING

```
<160> NUMBER OF SEQ ID NOS: 23

<210> SEQ ID NO 1
<211> LENGTH: 7
<212> TYPE: PRT
<213> ORGANISM: Homo sapiens

<400> SEQUENCE: 1

Ile Leu Trp Ile Asp Ala Arg
1               5

<210> SEQ ID NO 2
<211> LENGTH: 7
<212> TYPE: PRT
<213> ORGANISM: Homo sapiens

<400> SEQUENCE: 2

Val Tyr Trp Ser Asp Val Arg
1               5

<210> SEQ ID NO 3
<211> LENGTH: 10
<212> TYPE: PRT
<213> ORGANISM: Homo sapiens

<400> SEQUENCE: 3

Asn Val Ile Ala Leu Ala Phe Asp Tyr Arg
1               5                   10

<210> SEQ ID NO 4
<211> LENGTH: 10
<212> TYPE: PRT
<213> ORGANISM: Homo sapiens

<400> SEQUENCE: 4

Ser Glu Arg Pro Pro Ile Phe Glu Ile Arg
1               5                   10

<210> SEQ ID NO 5
<211> LENGTH: 13
<212> TYPE: PRT
<213> ORGANISM: Homo sapiens

<400> SEQUENCE: 5

Ser Leu Pro Pro Ala Ala Pro Thr Thr Ser Asn Arg
1               5                   10

<210> SEQ ID NO 6
<211> LENGTH: 12
<212> TYPE: PRT
<213> ORGANISM: Homo sapiens

<400> SEQUENCE: 6
```

```
Thr Val Leu Val Ser Ser Gly Leu Arg Glu Pro Arg
1               5                   10
```

<210> SEQ ID NO 7
<211> LENGTH: 12
<212> TYPE: PRT
<213> ORGANISM: Homo sapiens

<400> SEQUENCE: 7

```
Thr Thr Leu Leu Ala Gly Asp Ile Glu His Pro Arg
1               5                   10
```

<210> SEQ ID NO 8
<211> LENGTH: 11
<212> TYPE: PRT
<213> ORGANISM: Homo sapiens

<400> SEQUENCE: 8

```
Glu Tyr Ala Gly Tyr Leu Leu Tyr Ser Glu Arg
1               5                   10
```

<210> SEQ ID NO 9
<211> LENGTH: 12
<212> TYPE: PRT
<213> ORGANISM: Homo sapiens

<400> SEQUENCE: 9

```
Tyr Val Val Ile Ser Gln Gly Leu Asp Lys Pro Arg
1               5                   10
```

<210> SEQ ID NO 10
<211> LENGTH: 13
<212> TYPE: PRT
<213> ORGANISM: Homo sapiens

<400> SEQUENCE: 10

```
Glu Thr Val Ile Thr Met Ser Gly Asp Asp His Pro Arg
1               5                   10
```

<210> SEQ ID NO 11
<211> LENGTH: 12
<212> TYPE: PRT
<213> ORGANISM: Homo sapiens

<400> SEQUENCE: 11

```
Lys Pro Glu His Glu Leu Phe Leu Val Tyr Gly Lys
1               5                   10
```

<210> SEQ ID NO 12
<211> LENGTH: 13
<212> TYPE: PRT
<213> ORGANISM: Homo sapiens

<400> SEQUENCE: 12

```
Asp Val Ile Glu Val Ala Gln Met Lys Gly Glu Asn Arg
1               5                   10
```

<210> SEQ ID NO 13
<211> LENGTH: 13
<212> TYPE: PRT
<213> ORGANISM: Homo sapiens

<400> SEQUENCE: 13

```
Val Asp Lys Gly Gly Ala Leu His Ile Tyr His Gln Arg
1               5                   10
```

<210> SEQ ID NO 14
<211> LENGTH: 14
<212> TYPE: PRT
<213> ORGANISM: Homo sapiens

<400> SEQUENCE: 14

Ile Val Phe Pro His Gly Ile Thr Leu Asp Leu Val Ser Arg
1               5                   10

<210> SEQ ID NO 15
<211> LENGTH: 14
<212> TYPE: PRT
<213> ORGANISM: Homo sapiens

<400> SEQUENCE: 15

Ala Val Thr Asp Glu Glu Pro Phe Leu Ile Phe Ala Asn Arg
1               5                   10

<210> SEQ ID NO 16
<211> LENGTH: 14
<212> TYPE: PRT
<213> ORGANISM: Homo sapiens

<400> SEQUENCE: 16

Ser Leu Asp Pro Phe Lys Pro Phe Ile Ile Phe Ser Asn Arg
1               5                   10

<210> SEQ ID NO 17
<211> LENGTH: 13
<212> TYPE: PRT
<213> ORGANISM: Homo sapiens

<400> SEQUENCE: 17

Gly Tyr Leu Phe Trp Thr Glu Trp Gly Gln Tyr Pro Arg
1               5                   10

<210> SEQ ID NO 18
<211> LENGTH: 16
<212> TYPE: PRT
<213> ORGANISM: Homo sapiens

<400> SEQUENCE: 18

Thr Val Leu Trp Pro Asn Gly Leu Ser Leu Asp Ile Pro Ala Gly Arg
1               5                   10                  15

<210> SEQ ID NO 19
<211> LENGTH: 15
<212> TYPE: PRT
<213> ORGANISM: Homo sapiens

<400> SEQUENCE: 19

Ile Leu Trp Ile Asp Ala Arg Ser Asp Ala Ile Tyr Ser Ala Arg
1               5                   10                  15

<210> SEQ ID NO 20
<211> LENGTH: 19
<212> TYPE: PRT
<213> ORGANISM: Homo sapiens

<400> SEQUENCE: 20

Ser Asp Ala Ile Tyr Ser Ala Arg Tyr Asp Gly Ser Gly His Met Glu
1               5                   10                  15

Val Leu Arg

```
<210> SEQ ID NO 21
<211> LENGTH: 21
<212> TYPE: PRT
<213> ORGANISM: Homo sapiens

<400> SEQUENCE: 21

Asn Ser Thr Thr Leu Val Met His Met Lys Val Tyr Asp Glu Ser Ile
1               5                   10                  15

Gln Leu Asp His Lys
            20

<210> SEQ ID NO 22
<211> LENGTH: 21
<212> TYPE: PRT
<213> ORGANISM: Homo sapiens

<400> SEQUENCE: 22

Ile Tyr Trp Ala Asp Ala Arg Glu Asp Tyr Ile Glu Phe Ala Ser Leu
1               5                   10                  15

Asp Gly Ser Asn Arg
            20

<210> SEQ ID NO 23
<211> LENGTH: 22
<212> TYPE: PRT
<213> ORGANISM: Homo sapiens

<400> SEQUENCE: 23

Gly Phe Gln His Gln Arg Met Thr Asn Gly Ala Met Asn Val Glu Ile
1               5                   10                  15

Gly Asn Pro Thr Tyr Lys
            20
```